(12) United States Patent
Burke et al.

(10) Patent No.: US 11,198,705 B2
(45) Date of Patent: Dec. 14, 2021

(54) HYBRID AMPHOTERICIN B DERIVATIVES WITH REDUCED TOXICITY

(71) Applicant: The Board of Trustees of the University of Illinois, Urbana, IL (US)

(72) Inventors: Martin D. Burke, Champaign, IL (US); Anuj Khandelwal, Salt Lake City, UT (US); Jiabao Zhang, Urbana, IL (US); Anna SantaMaria, Rockville, MD (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 16/563,243

(22) Filed: Sep. 6, 2019

(65) Prior Publication Data

US 2020/0079811 A1    Mar. 12, 2020

Related U.S. Application Data

(60) Provisional application No. 62/728,203, filed on Sep. 7, 2018.

(51) Int. Cl.
*C07H 17/08* (2006.01)
*C07H 17/00* (2006.01)
*A61K 9/00* (2006.01)

(52) U.S. Cl.
CPC ........... *C07H 17/00* (2013.01); *A61K 9/0019* (2013.01); *A61K 9/0053* (2013.01); *C07H 17/08* (2013.01)

(58) Field of Classification Search
None
See application file for complete search history.

(56) References Cited

U.S. PATENT DOCUMENTS

| | | | |
|---|---|---|---|
| 9,957,290 B2 * | 5/2018 | Burke | A61K 31/7048 |
| 10,246,478 B2 | 4/2019 | Miyazaki et al. | |
| 10,597,420 B2 * | 3/2020 | Burke | A61K 31/7008 |
| 10,882,883 B2 * | 1/2021 | Burke | A61P 31/04 |
| 2016/0215012 A1 | 7/2016 | Burke et al. | |
| 2017/0088572 A1 | 3/2017 | Burke et al. | |
| 2017/0190729 A1 | 7/2017 | Miyazaki et al. | |
| 2020/0079811 A1 | 3/2020 | Burke et al. | |

FOREIGN PATENT DOCUMENTS

WO    WO-2020/051465 A1    3/2020

OTHER PUBLICATIONS

International Search Report for International Application No. PCT/US2019/049971 dated Nov. 15, 2019.

* cited by examiner

*Primary Examiner* — Traviss C McIntosh, III
(74) *Attorney, Agent, or Firm* — Foley Hoag LLP

(57) ABSTRACT

Disclosed are derivatives of amphotericin B (AmB) characterized by improved clinical efficacy with reduced toxicity compared to AmB. Also disclosed are pharmaceutical compositions comprising the AmB derivatives, therapeutic methods of using the AmB derivatives and methods of making the AmB derivatives.

17 Claims, 32 Drawing Sheets

FIG. 2A

| | AmB | AmdeB | C2'deOAmB | C2'epiAmB |
|---|---|---|---|---|
| binds ergosterol (by ITC) | YES | NO | YES | YES |
| binds cholesterol (by ITC) | YES | NO | NO | NO |
| toxic concentrations (µM) | | | | |
| ergosterol-containing yeast cells — S. cerevisiae | 0.5 | >500 | 1 | 2 |
| ergosterol-containing yeast cells — C. albicans | 0.25 | >500 | 1 | 2 |
| cholesterol-containing yeast cells — red blood cells | 8.5 | >500 | >500 | >500 |
| cholesterol-containing yeast cells — renal epithelial cells | 2.4 | >80 | >80 | >80 |

FIG. 8A

Panel of Candida and Aspergillus isolates performed at Evotec

MIC (μg/mL) 100 % Inhibition of Growth

| Organism | AmB | C2'epiAmB |
|---|---|---|
| C. tropicalis FA1572 | 2 | 1 |
| C. tropicalis ATCC750 | 1 | 1 |
| C. albicans A226 | 1 | 1 |
| C. albicans SC5314 | 1 | 1 |
| C. albicans FA8555 | 1 | 1 |
| C. albicans FA6862 | 1 | 1 |
| C. krusei ATCC6528 | 2 | 1 |
| C. glabrata NCPF3240 | 1 | 1 |
| C. glabrata ATCC2001 | 1 | 1 |
| A. fumigatus 293 | 0.5 | 2 |
| A. fumigatus 91 | 1 | >32 |
| A. terreus AT49 | 2 | 2 |
| A. fumigatus 1163 | 0.5 | 2 |
| A. terreus NIH2624 | 1 | 1 |
| A. fumigatus ATCC204305 | 0.5 | 2 |

FIG. 8B

Extended panel of *Aspergillus* isolates performed at UT San Antonio

| | | WAF-1 | WAF-2 | WAF-3 | WAF-4 | WAF-5 | WAF-6 | WAF-7 | WAF-8 | WAF-9 | WAF-10 |
|---|---|---|---|---|---|---|---|---|---|---|---|
| Wild-type *A. fumigatus* | AmB | 2 | 1 | 2 | 1 | 2 | 1 | 2 | 1 | 2 | 2 |
| | C2'epiAmB | 16 | 8 | >16 | 8 | 16 | 4 | 16 | 8 | 8 | >16 |

| | | AF-1 | AF-2 | AF-3 | AF-4 | AF-5 | AF-6 | AF-7 | AF-8 | AF-9 | AF-10 |
|---|---|---|---|---|---|---|---|---|---|---|---|
| Azole-resistant *A. fumigatus* | AmB | 1 | 1 | 1 | 1 | 1 | 1 | 2 | 1 | 1 | 1 |
| | C2'epiAmB | 16 | 16 | 8 | 4 | 8 | 8 | >16 | 8 | 8 | 8 |

| | | AFL-1 | AFL-2 | AFL-3 | AFL-4 | AFL-5 | AFL-6 | AFL-7 | AFL-8 | AFL-9 | AFL-10 |
|---|---|---|---|---|---|---|---|---|---|---|---|
| *A. flavus* | AmB | 2 | 1 | 2 | 2 | 2 | 2 | 2 | 2 | 2 | 2 |
| | C2'epiAmB | 4 | 4 | 4 | 4 | 4 | 4 | 4 | 4 | 4 | 4 |

| | | AT-1 | AT-2 | AT-3 | AT-4 | AT-5 | AT-6 | AT-7 | AT-8 | AT-9 | AT-10 |
|---|---|---|---|---|---|---|---|---|---|---|---|
| *A. terreus* | AmB | 2 | 1 | 2 | 2 | 1 | 2 | 2 | 1 | 1 | 2 |
| | C2'epiAmB | >16 | 8 | 16 | 8 | 8 | 8 | 8 | 8 | 8 | 8 |

FIG. 8C

| | A. fumigatus (CEA10) | A. fumigatus (ATTC#3626) | A. fumigatus (S678P) | A. fumigatus (F14196) | Scedosporium apiospermum (ATCC#MYA3634) | Scedosporium prolificans | Fusarium solani (ATCC#MYA3636) | Mucor circinelloides (ATCC#42257) | Rhizomucor pusillus (ATCC#46342) | Rhizopus oryzae | Paecilomyces variotii |
|---|---|---|---|---|---|---|---|---|---|---|---|
| AmB | 0.5 | 0.5 | 0.5 | 0.25 | >4 | >4 | 0.25 | 0.25 | 0.25 | 0.5 | 0.5 |
| | 0.5 | 0.5 | 0.5 | 0.25 | >4 | >4 | 0.25 | 0.125 | 0.125 | 0.25 | 0.5 |
| Caspofungin | 0.5 | 0.25 | >8 | >8 | 0.125 | 2 | 1 | >8 | >8 | >8 | 0.125 |
| Voriconazole | 0.5 | 0.5 | 0.25 | 0.25 | 0.125 | 0.25 | | >8 | >8 | >8 | 0.125 |
| C2-epAmB | 2 | 2 | 2 | 1 | >4 | >4 | 0.5 | 0.25 | 0.5 | 1 | 1 |

FIG. 11B

| | CP | CK | CA-1 | CA-2 | CG-1 | CG-2 | CG-3 | CN | PAEC | AF-1 | AF-2 | Average MIC |
|---|---|---|---|---|---|---|---|---|---|---|---|---|
| AmB | 1 | 1 | 2 | 1 | 1 | 0.5 | 1 | 1 | 2 | 2 | 1 | 1.23 |
| AmBAU | 1 | 2 | 1 | 2 | 1 | 1 | 1 | 1 | 2 | 2 | 2 | 1.45 |
| AmBMU | 1 | 2 | 1 | 2 | 1 | 1 | 1 | 1 | 2 | 2 | 2 | 1.45 |
| AmBBCBU | 2 | 4 | 2 | 4 | 2 | 2 | 2 | 2 | 2 | 4 | 4 | 2.73 |
| AmBMEU | 2 | 4 | 2 | 2 | 2 | 2 | 2 | 2 | 2 | 4 | 2 | 2.36 |
| AmBTACBU | 0.5 | 1 | 0.5 | 1 | 1 | 0.5 | 1 | 1 | 1 | 2 | 1 | 0.95 |

FIG. 11C

| | A. fumigatus (ATTC#3626) | A. fumigatus (S678P) | A. fumigatus (F14196) | Scedosporium apiospermum (ATTC#MYA3634) | Scedosporium prolificans | Fusarium solani (ATCC#MYA3636) | Mucor circinelloides (ATCC#42257) | Rhizomucor pusillus (ATCC#46342) | Rhizopus oryzae | Paecilomyces variotii |
|---|---|---|---|---|---|---|---|---|---|---|
| AmB | 0.5 | 0.5 | 0.5 | 0.25 | >4 | 0.25 | 0.25 | 0.25 | 0.5 | 0.5 |
| Caspofungin | 2 | 2 | 2 | 1 | >4 | 0.5 | 0.25 | 0.5 | 1 | 1 |
| AmBisome | 0.5 | 0.25 | 0.5 | 0.25 | 2 | 0.125 | 0.5 | 0.25 | 0.5 | 0.25 |
| AmBidisk | 1 | 1 | 0.5 | 0.5 | 4 | 0.25 | 0.5 | 0.5 | 2 | 0.5 |
| AmBCD | 1 | 1 | 1 | 0.5 | >4 | 0.5 | 1 | 0.5 | >4 | 0.5 |

| | AmB | AmBAU | AmBTACBU |
|---|---|---|---|
| S. cerevisea | 0.5 | 0.25 | 0.25 |
| C. albicans | 1 | 0.5 | 0.5 |
| C. tropicalis CBS94 | 2 | 0.5 | 0.5 |
| C. glabrata CBS138 | 0.5 | 0.25 | 0.125 |
| C. krusei CBS573 | 2 | 1 | 1 |
| A. fumigatus 91 | 2 | 0.5 | 0.25 |
| A. fumigatus 93 | 2 | 0.25 | 0.25 |
| A. fumigatus 1163 | 1 | 0.25 | 0.25 |
| A. fumigatus MCVC#10 | 1 | 1 | 0.5 |
| Average MIC (µM) | 1.33 | 0.5 | 0.4 |

FIG. 11D

| Animal | Compound | $c_{max}$ (ng/mL) | AUC (ng*h/mL) |
|---|---|---|---|
| Mouse | AmB (1 mg/kg) | 5,133 | 35,461 |
| | AmBAU (1 mg/kg) | 2,163 | 32,028 |
| Rat | AmB (1 mg/kg) | 4,173 ± 448 | 11,359 ± 1,591 |
| | AmBAU (1 mg/kg) | 1,773 ± 422 | 26,880 ± 494 |
| Dog | AmB (1 mg/kg) | 505 ± 71 | 10,380 ± 3,390 |
| | AmBAU (1 mg/kg) | 1,120 ± 230 | 43,900 ± 4,300 |

FIG. 14

| | $K_D$ erg (nM) | $K_D$ chol (nM) |
|---|---|---|
| AmB | 120 | 840 |
| AmBAU | 196 | 590 |
| C2'epiAmB | 150 | >2000 |

FIG. 15

| | AmB | C2'epiAmB | AmBAU | C2'epiAmBAU |
|---|---|---|---|---|
| C. albicans | 0.5 | 4 | 0.5 | 0.25 |
| C. krusei | 1 | 4 | 1 | 1 |
| C. glabrata | 0.5 | 8 | 0.25 | 0.5 |
| C. tropicalis | 1 | 4 | 0.5 | 0.5 |
| A. fumigatus 91 | 2 | >64 | 1 | 1 |
| A. fumigatus 1163 | 2 | >64 | 0.5 | 0.125 |
| A. fumigatus 1100 | 1 | 32 | 1 | 0.25 |

FIG. 18

HYBRID AMPHOTERICIN B DERIVATIVES WITH REDUCED TOXICITY

GOVERNMENT SUPPORT

This invention was made with government support under Grant No. GM118185, awarded by the National Institutes of Health. The government has certain rights in the invention.

BACKGROUND OF THE INVENTION

Amphotericin B (AmB) has potent and dose-dependent fungicidal activity against a broad range of fungal pathogens and has evaded resistance for over half a century. The fungicidal, as opposed to fungistatic, activity of AmB is essential in immunocompromised patients which lack a robust immune system to help clear an infection. Broad antifungal activity is especially important in critically ill patients when the identity of the pathogen is unknown and immediate empirical therapy is required. Unfortunately, AmB is exceptionally toxic, which limits its use to low-dose protocols that often fail to eradicate disease. An AmB derivative that retains potent, broad spectrum, and resistance-evasive fungicidal activity but lacks dose-limiting toxicities would enable a new high-dose treatment paradigm with improved clinical efficacy.

SUMMARY OF THE INVENTION

An aspect of the invention is a compound represented by Formula (I) or a pharmaceutically acceptable salt thereof:

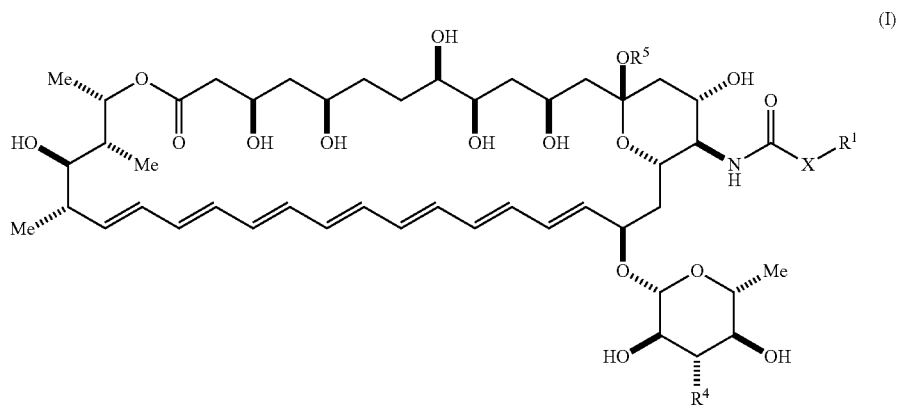

wherein, independently for each occurrence:

$X$ is $-N(R^2)-$;

$R^1$ is a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, acyl, amino, amido, aminoalkyl, and alkoxyl; or $R^1$ and $R^2$, together with the nitrogen to which they are attached, may form a substituted or unsubstituted 3- to 10-membered heterocyclic ring, wherein said ring is monocyclic, bicyclic, tricyclic, or spirocyclic;

$R^2$ is hydrogen or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, acyl, amino, amido, aminoalkyl, and alkoxyl;

$R^4$ is selected from the group consisting of secondary amino, tertiary amino, amido, azido, isonitrile, nitro, urea, isocyanate, carbamate, and guanidinyl; and $R^5$ is selected from the group consisting of hydrogen, alkyl, and haloalkyl.

An aspect of the invention is a compound represented by Formula (IV) or a pharmaceutically acceptable salt thereof:

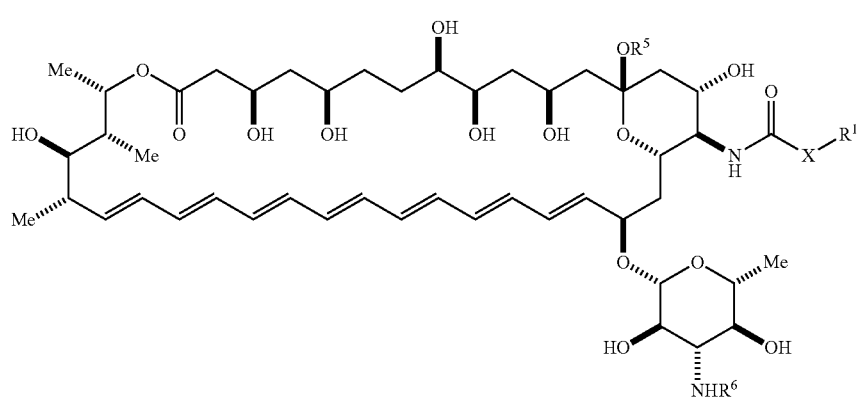

(IV)

wherein:
X is —N(R²)—;
R¹ is a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, acyl, amino, amido, aminoalkyl, and alkoxyl; or R¹ and R², together with the nitrogen to which they are attached, may form a substituted or unsubstituted 3- to 10-membered heterocyclic ring, wherein said ring is monocyclic, bicyclic, tricyclic, or spirocyclic;
R² is hydrogen or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, acyl, amino, amido, aminoalkyl, and alkoxyl;
R⁵ is selected from the group consisting of hydrogen, alkyl, and haloalkyl;
R⁶ is C(O)OR^f; and
R^f is selected from the group consisting of 2-alken-1-yl, tert-butyl, benzyl and fluorenylmethyl.

An aspect of the invention is a compound represented by Formula (V) or a pharmaceutically acceptable salt thereof:

wherein:
R⁵ is selected from the group consisting of hydrogen, alkyl, and haloalkyl;
—XR¹ is selected from the group consisting of

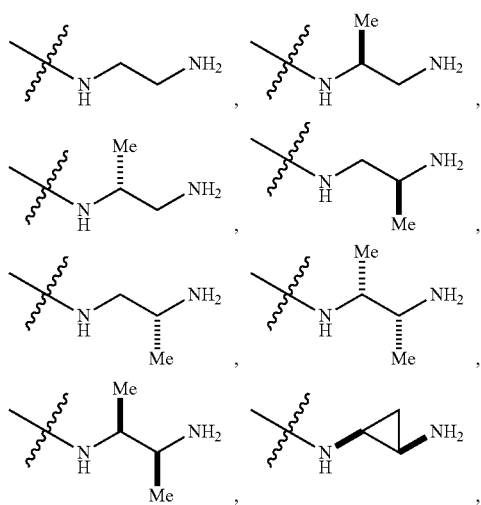

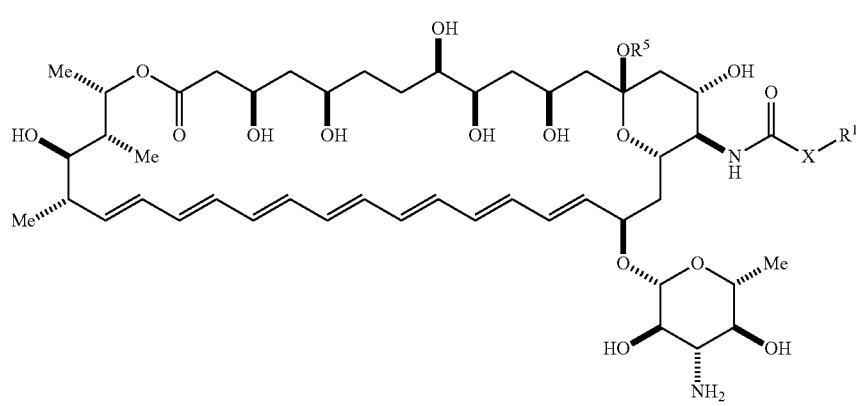

(V)

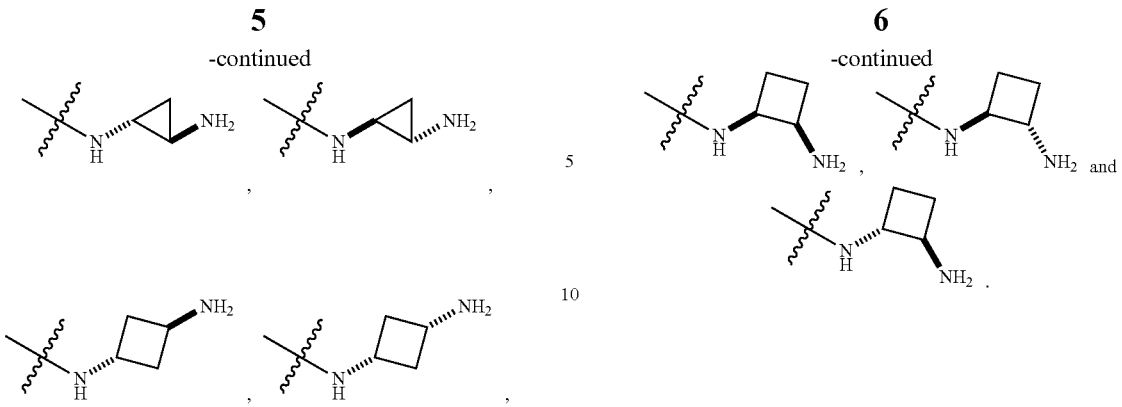

An aspect of the invention is a compound represented by Formula (II) or a pharmaceutically acceptable salt thereof:

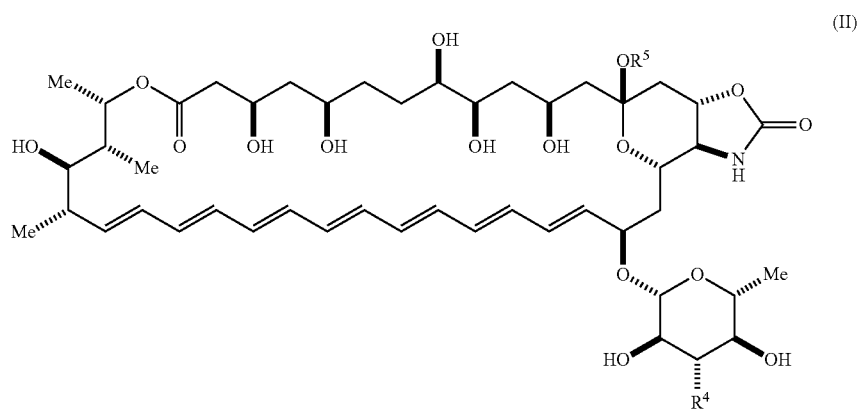

wherein, independently for each occurrence:
R$^4$ is selected from the group consisting of primary amino, secondary amino, tertiary amino, amido, azido, isonitrile, nitro, urea, isocyanate, carbamate, and guanidinyl; and
R$^5$ is selected from the group consisting of hydrogen, alkyl, and haloalkyl.

An aspect of the invention is a compound represented by Formula (III) or a pharmaceutically acceptable salt thereof:

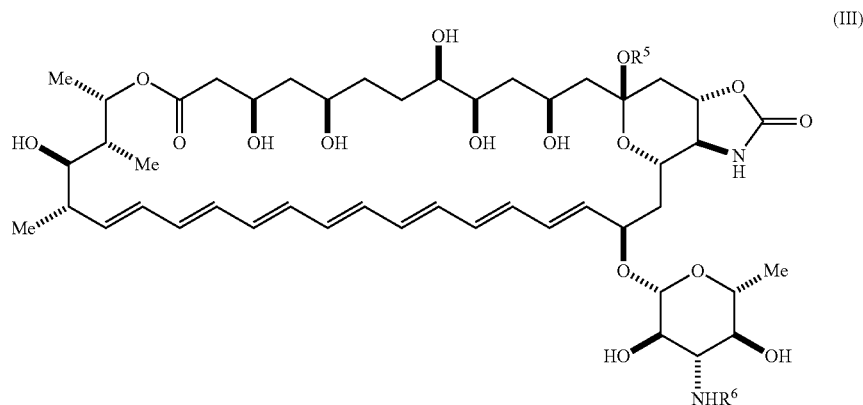

wherein:
R[5] is selected from the group consisting of hydrogen, alkyl, and haloalkyl;
R[6] is —C(O)OR[f]; and
R[f] is selected from the group consisting of 2-alken-1-yl, tert-butyl, benzyl and fluorenylmethyl.

An aspect of the invention is a pharmaceutical composition, comprising a compound of the invention and a pharmaceutically acceptable carrier.

An aspect of the invention is a method of treating a fungal infection, comprising administering to a subject in need thereof a therapeutically effective amount of a compound of the invention, thereby treating the fungal infection.

An aspect of the invention is a method of making a C16 urea derivative of C2'epi-Amphotericin B according to any one of the four transformations shown in Scheme 1:

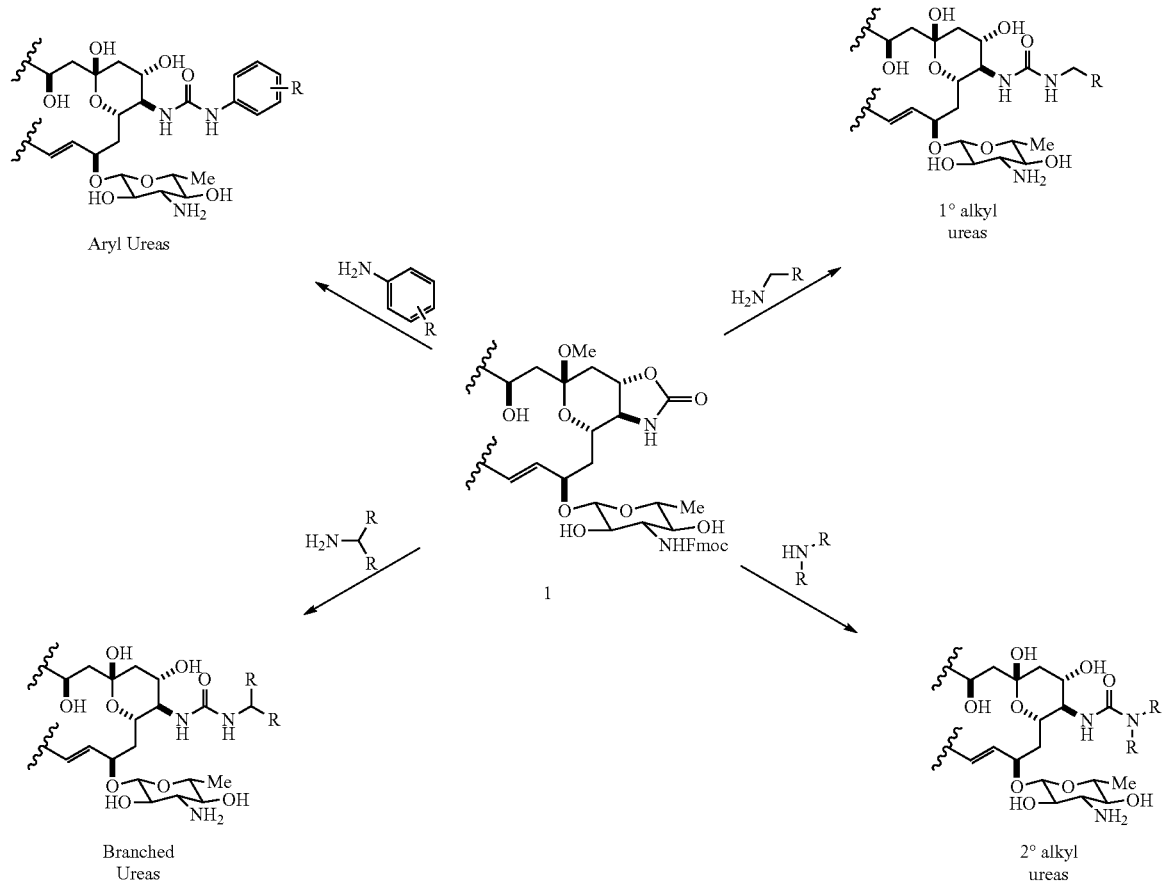

wherein 1 represents

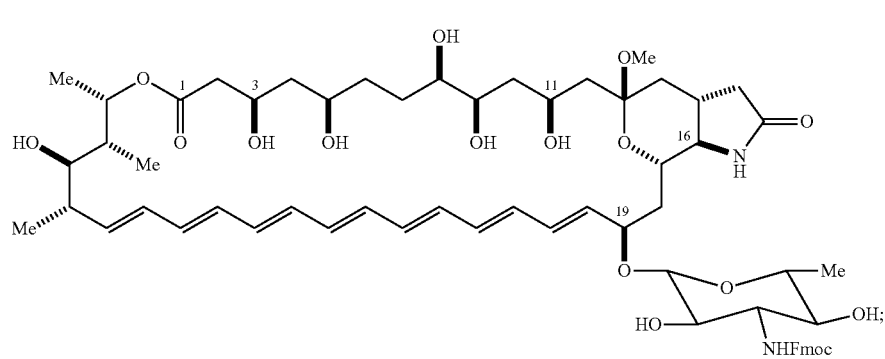

and each instance of R is independently selected from the group consisting of hydrogen, halogen, straight- and branched-chain alkyl, cycloalkyl, cycloalkylalkyl, heterocyclyl, aryl, heteroaryl, aralkyl, heteroaralkyl, hydroxyl, sulfhydryl, carboxyl, amino, amido, azido, nitro, cyano, aminoalkyl, and alkoxyl.

BRIEF DESCRIPTION OF THE FIGURES

FIG. 2A represents chemical structures and biophysical activities of AmB, AmdeB, C2'deOAmB, and C2'epiAmB.

FIG. 8A depicts in vitro antifungal activity of AmB and C2'epiAmB against a broad range of fungal pathogens in a panel of Candida and Aspergillus isolates.

FIG. 8B depicts in vitro antifungal activity of AmB and C2'epiAmB against a broad range of fungal pathogens in a panel of Aspergillus isolates.

FIG. 8C depicts in vitro antifungal activity of AmB and C2'epiAmB against a broad range of fungal pathogens in a panel of clinically relevant invasive molds.

FIG. 11B depicts in vitro antifungal activity of several derivatives against a panel of clinical isolates.

FIG. 11C depicts in vitro antifungal activity of several derivatives against a wide range of clinically relevant pathogens.

FIG. 11D depicts in vitro antifungal activity of AmB, AmBAU and AmBTACBU against clinically relevant Candida species and challenging strains of A. fumigatus.

FIG. 14 depicts the PK properties of AmB and AmBAU in mice, rats and dogs.

FIG. 15 depicts the binding of AmB or derivatives to ergosterol and cholesterol, and shows that AmBMU retains the capacity to bind cholesterol, which is consistent with the retained mammalian toxicity of AmBUreas.

FIG. 18 depicts the comparison of in vitro antifungal activity of C2'epiAmBAU hybrid to AmB, C2'epiAmB and AmBAU.

DETAILED DESCRIPTION OF THE INVENTION

Figure 1A:
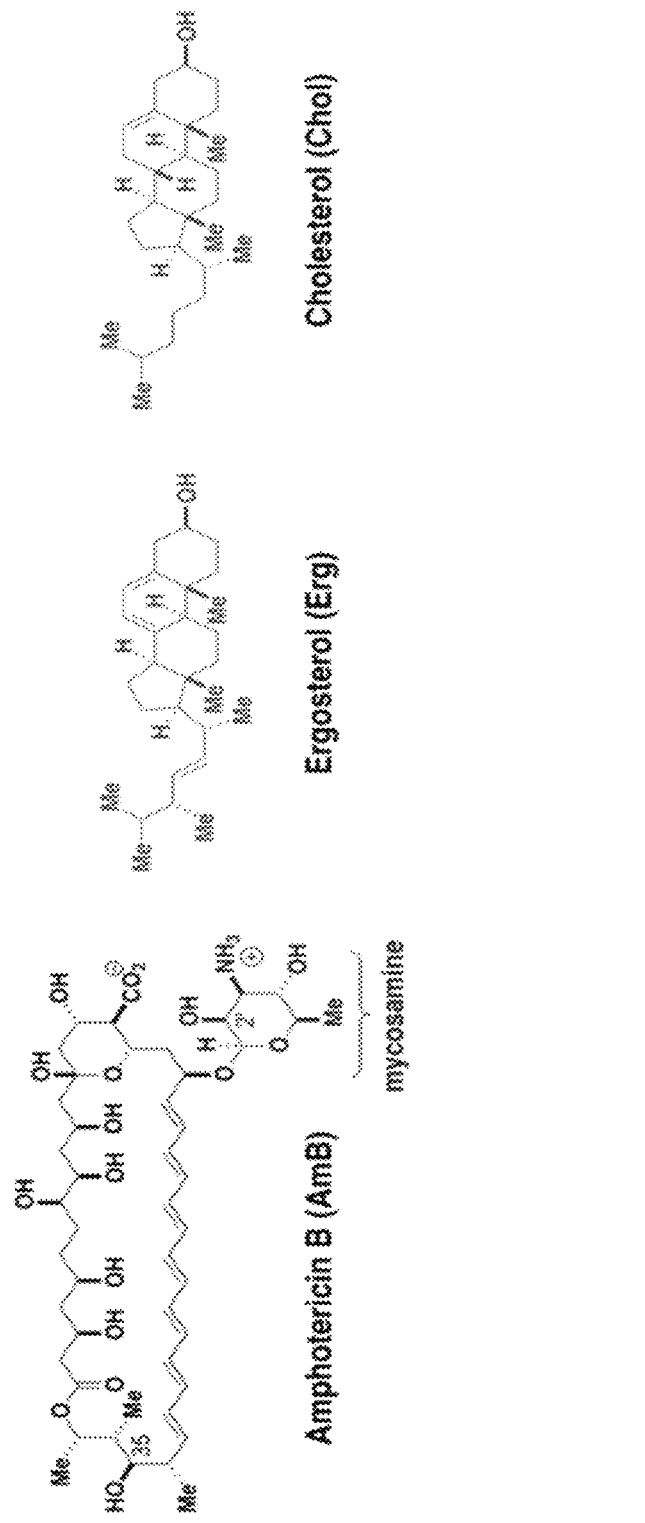
FIG. 1A represents chemical structures of amphotericin B, the primary fungal sterol—ergosterol, and the primary human sterol—cholesterol.

Amphotericin B (AmB) is a polyene macrolide with a mycosamine appendage, the complete compound having the following structure:

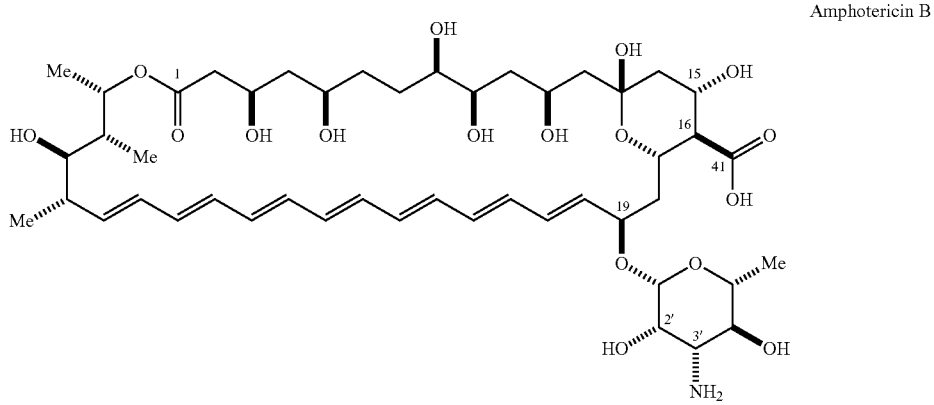

Amphotericin B

AmB is generally obtained from a strain of *Streptomyces nodosus*. It is currently approved for clinical use in the United States for the treatment of progressive, potentially life-threatening fungal infections, including such infections as systemic or deep tissue candidiasis, aspergillosis, cryptococcosis, blastomycosis, coccidioidomycosis, histoplasmosis, and mucormycosis, among others. It is generally formulated for intravenous injection. Amphotericin B is commercially available, for example, as Fungizone® (Squibb), Amphocin® (Pfizer), Abelcet® (Enzon), and Ambisome® (Astellas). Due to its undesirable toxic side effects, dosing is generally limited to a maximum of about 1.0 mg/kg/day and total cumulative doses not to exceed about 3 g in humans.

AmB kills both fungal and human cells by forming a cytocidal extramembranous sterol sponge. Anderson, T. M. et al., *Nat Chem Biol* 2014, 10 (5), 400-6. This large aggregate sits on the surface of lipid bilayers and rapidly extracts membrane sterols, which leads to cell death. Membrane permeabilization is not required. Based on this mechanism, a small molecule-based ligand-selective allosteric effect would enable selective binding of ergosterol over cholesterol and would eliminate the mammalian toxicity of AmB (in the form of C2'epiAmB). See Wilcock, B. C. et al., *J Am Chem Soc* 2013, 135 (23), 8488-91. The present invention discloses the $K_{DS}$ for the binding of both ergosterol and cholesterol to the AmB sterol sponge, which provides a quantitative and mechanistically-grounded biophysical parameter to guide rational optimization of the therapeutic index of this clinically significant natural product.

The present invention relates, at least in part, to the discovery by the inventors of further derivatives of AmB which also are characterized by improved therapeutic index compared to AmB. The various derivatives, i.e., compounds of the invention, can be semi-synthetic or fully synthetic. An aspect of the invention is the development of a new synthetic derivative of AmB that retains potent binding of ergosterol but shows no detectable binding of cholesterol. This derivative retains fungicidal potency against many yeasts and molds but shows zero detectable mammalian toxicity. This demonstrates that differential binding of ergosterol over cholesterol is possible and provides a non-toxic variant of AmB that preserves desirable antifungal properties. Compounds of the invention enable a new high-dose treatment strategy to eradicate life-threatening invasive fungal infections with a significantly improved safety profile.

Compounds of the invention and pharmaceutical compositions of the invention are useful for inhibiting the growth of a fungus. In one embodiment, an effective amount of a compound of the invention is contacted with a fungus, thereby inhibiting growth of the fungus. In one embodiment, a compound of the invention, or a pharmaceutically acceptable salt thereof, is added to or included in tissue culture medium.

Compounds of the invention and pharmaceutical compositions of the invention are useful for the treatment of fungal infections in a subject. In one embodiment, a therapeutically effective amount of a compound of the invention, or a pharmaceutically acceptable salt thereof, is administered to a subject in need thereof, thereby treating the fungal infection.

Yeasts are eukaryotic organisms classified in the kingdom Fungi. Fungi include yeasts, molds, and larger organisms including mushrooms. Yeasts and molds are of clinical relevance as infectious agents. Yeasts are typically described as budding forms of fungi. Of particular importance in connection with the invention are species of yeast that can cause infections in mammalian hosts. Such infections most commonly occur in immunocompromised hosts, including hosts with compromised barriers to infection (e.g., burn victims) and hosts with compromised immune systems (e.g., hosts receiving chemotherapy or immune suppressive therapy, and hosts infected with HIV). Pathogenic yeasts include, without limitation, various species of the genus *Candida*, as well as of *Cryptococcus*. Of particular note among pathogenic yeasts of the genus *Candida* are *C. albicans*, *C. tropicalis*, *C. stellatoidea*, *C. glabrata*, *C. krusei*, *C. parapsilosis*, *C. guilliermondii*, *C. viswanathii*, and *C. lusitaniae*. The genus *Cryptococcus* specifically includes *Cryptococcus neoformans*. Yeast can cause infections of mucosal membranes, for example oral, esophageal, and vaginal infections in humans, as well as infections of bone, blood, urogenital tract, and central nervous system. This list is exemplary and is not limiting in any way.

A number of fungi (apart from yeast) can cause infections in mammalian hosts. Such infections most commonly occur in immunocompromised hosts, including hosts with compromised barriers to infection (e.g., burn victims) and hosts with compromised immune systems (e.g., hosts receiving chemotherapy or immune suppressive therapy, and hosts infected with HIV). Pathogenic fungi (apart from yeast) include, without limitation, species of *Aspergillus, Rhizopus, Mucor, Histoplasma, Coccidioides, Blastomyces, Trichophyton, Microsporum*, and *Epidermophyton*. Of particular note among the foregoing are *A. fumigatus*, *A. flavus*, *A. niger*, *H. capsulatum*, *C. immitis*, and *B. dermatitidis*. Fungi can cause systemic and deep tissue infections in lung, bone, blood, urogenital tract, and central nervous system, to name a few. Some fungi are responsible for infections of the skin and nails.

Definitions

For convenience, certain terms employed in the specification, examples, and appended claims are collected here.

The articles "a" and "an" are used herein to refer to one or to more than one (i.e., to at least one) of the grammatical object of the article. By way of example, "an element" means one element or more than one element.

The term "acyl", as used herein, refers to —C(═O)R, where R represents an alkyl, aryl, heteroaryl, aralkyl, or heteroaralkyl group as defined herein. Amides (RC(O)NR$_2$) and esters (RC(O)OR') are classes of acyl compounds, as are ketones (RC(O)R) and aldehydes (RC(O)H). Non-limiting examples of acyl groups include formyl, acetyl, propionyl, and benzyl.

The terms "alkenyl" and "alkynyl" are art-recognized and refer to unsaturated aliphatic groups analogous in length and possible substitution to the alkyls described herein, but that contain at least one double or triple bond, respectively.

The term "alkoxy" means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxycarbonyl" means an alkoxy group, as defined herein, appended to the parent molecular moiety through a carbonyl group, represented by —C(═O)—, as defined herein. Representative examples of alkoxycarbonyl include, but are not limited to, methoxycarbonyl, ethoxycarbonyl, and tert-butoxycarbonyl.

The term "alkyl" means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, and n-hexyl.

The term "alkyl" is art-recognized, and includes saturated aliphatic groups, including straight-chain alkyl groups, branched-chain alkyl groups, and cycloalkyl (alicyclic) groups. In certain embodiments, a straight-chain or branched-chain alkyl has about 30 or fewer carbon atoms in its backbone (e.g., $C_1$-$C_{30}$ for straight chain, $C_3$-$C_{30}$ for branched chain), and alternatively, about 20 or fewer. In certain embodiments, a straight-chain or branched-chain alkyl has about 10 or fewer carbon atoms in its backbone. In certain embodiments, a straight-chain alkyl has 1 to 6 carbon atoms in its backbone. In certain embodiments, a branched-chain alkyl has 3 to 8 carbon atoms in its backbone. Representative examples of linear and branched-chain alkyl groups include, but are not limited to, methyl, ethyl, n-propyl, iso-propyl, n-butyl, sec-butyl, iso-butyl, tert-butyl, n-pentyl, isopentyl, neopentyl, and n-hexyl. Cycloalkyls have from about 3 to about 10 carbon atoms in their ring structure. In certain embodiments, cycloalkyls have 3, 4, 5, 6, or 7 carbons in the ring structure. Representative examples of cycloalkyl groups include, but are not limited to, cyclopropyl, cyclobutyl, cyclopentyl, cyclohexyl, and cycloheptyl.

The term "alkylcarbonyl", as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonyloxy", as used herein, means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy.

The term "alkylthio", as used herein, means an alkyl group, as defined herein, appended to the parent molecular moiety through a sulfur atom. Representative examples of alkylthio include, but are not limited, methylthio, ethylthio, tert-butylthio, and hexylthio. The terms "arylthio", "alkenylthio", and "arylalkylthio," for example, are likewise defined in a corresponding fashion.

The term "amido", as used herein, refers to a moiety that may be represented by the general formula:

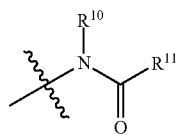

wherein $R^{10}$ and $R^{11}$ each independently represent hydrogen or a substituted or unsubstituted group selected from alkyl, cycloalkyl, cycloalkylalkyl, heterocyclyl, alkenyl, cycloalkenyl, aminoalkyl, aryl, heteroaryl, aralkyl, and heteroaralkyl. Nonlimiting examples of amido include those for which $R^{10}$ is hydrogen, and $R^{11}$ is selected from methyl, ethyl, propyl, isopropyl, propenyl, cyclohexyl, benzyl,

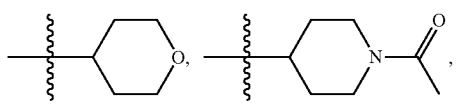

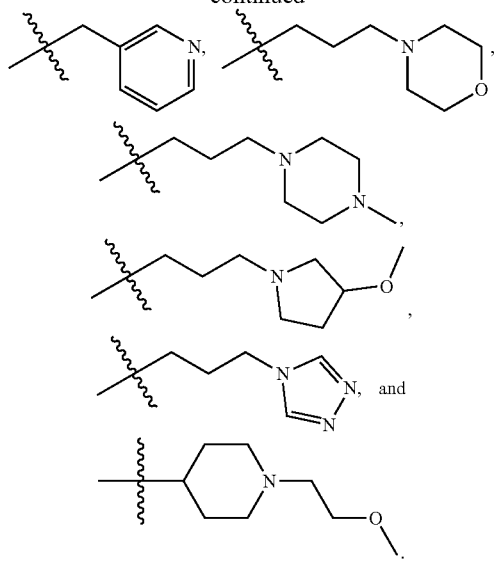

Additional nonlimiting examples of amido include those for which $R^{10}$ is hydrogen, and $R^{11}$ is selected from —$CH_2NH_2$, —$CH_2N(CH_3)_2$, and —$CH(NH_2)(CH_2)_nNH_2$, where n is an integer 1-6. Yet additional nonlimiting examples of amido include those for which $R^{10}$ is hydrogen, and $R^{11}$ is selected from

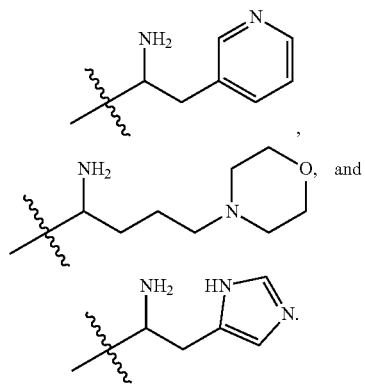

The terms "amino" and "amine" are art-recognized and refer to both unsubstituted and substituted amines, e.g., a moiety that may be represented by the general formulas:

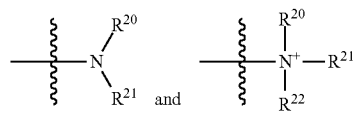

wherein $R^{20}$, $R^{21}$, and $R^{22}$ each independently represent a hydrogen, an alkyl, an alkenyl, —$(CH_2)_m$—$R^{61}$; or $R^{20}$ and $R^{21}$, taken together with the N atom to which they are attached, complete a heterocycle having from 4 to 10 atoms in the ring structure, wherein said ring is monocyclic, bicyclic, tricyclic, or spirocyclic; $R^{61}$ represents an aryl, a cycloalkyl, a cycloalkenyl, a heterocycle or a polycycle; and m is zero or an integer in the range of 1 to 8. In other embodiments, $R^{20}$ and $R^{21}$ (and optionally $R^{22}$) each independently represent a hydrogen, an alkyl, an alkenyl, or —(CH$_2$)$_m$—R$^{61}$. Thus, the term "alkylamine" includes an amine group, as defined above, having a substituted or unsubstituted alkyl attached thereto, i.e., at least one of R$^{20}$ and R$^{21}$ is an alkyl group. Nonlimiting examples of amino groups include —NH$_2$, —N(H)CH$_3$, —N(H)CH$_2$CH$_3$, —N(H)CH$_2$CH$_2$CH$_3$, —N(H)CH$_2$CH$_2$CH$_2$CH$_3$, —N(CH$_3$)$_2$, —N(CH(CH$_3$)$_2$)$_2$, —N(CH$_3$)CH$_2$CH$_3$, —N(CH$_3$)CH$_2$CH$_2$CH$_3$, —N(CH$_3$)CH$_2$CH$_2$CH$_2$CH$_3$, —N(CH$_2$CH$_3$)$_2$, —N(CH$_2$CH$_3$)CH$_2$CH$_2$CH$_3$, —N(CH$_2$CH$_3$)CH$_2$CH$_2$CH$_2$CH$_3$, —N(CH$_2$CH$_3$)$_2$, —N(CH$_2$CH$_2$CH$_3$)CH$_2$CH$_2$CH$_2$CH$_3$, —N(CH$_2$CH$_2$CH$_2$CH$_3$)$_2$,

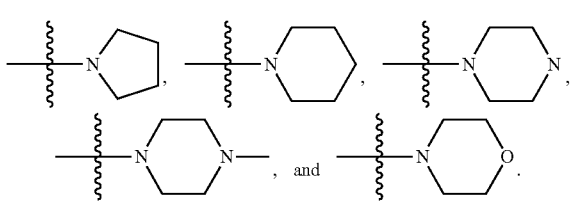

In certain embodiments, amino is —NH$_2$. In certain embodiments, amino is —N(H)CH$_3$.

The term "aminoalkyl" as used herein, means an amino group, as defined herein, appended to the parent molecular moiety through an alkyl group, also as defined herein.

The term "aromatic" refers to a planar monocyclic or polycyclic structure characterized by a cyclically conjugated molecular moiety containing 4n+2 electrons, wherein n is the absolute value of an integer. Aromatic groups comprising only carbon atoms in their ring structure are termed "aryl" groups. Aromatic groups comprising one or more heteroatoms in their ring structure are termed "heteroaryl" or "heteroaromatic" groups. Aromatic groups containing fused, or joined, rings also are referred to as polycyclic aromatic groups. For example, bicyclic aromatic groups containing heteroatoms in a hydrocarbon ring structure are referred to as bicyclic heteroaryl groups.

Examples of 5-, 6-, and 7-membered single-ring aromatic groups that may include from zero to four heteroatoms include, for example, benzene, pyrrole, furan, thiophene, imidazole, oxazole, thiazole, triazole, pyrazole, pyridine, pyrazine, pyridazine, pyrimidine, and the like.

Non-limiting examples of polycyclic aromatic and heteroaromatic groups include quinoline, isoquinoline, carbazole, naphthalene, anthracene, and pyrene.

The aryl groups of the invention can be optionally substituted with 1, 2, 3, 4 or 5 substituents independently selected from the group consisting of alkenyl, alkoxy, alkoxycarbonyl, alkoxysulfonyl, alkyl, alkylcarbonyl, alkylcarbonyloxy, alkyl sulfonyl, alkylthio, alkynyl, amido, amino, carboxy, cyano, formyl, halo, haloalkoxy, haloalkyl, hydroxyl, hydroxyalkyl, mercapto, nitro, phosphinyl, silyl and silyloxy. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The term "arylcarbonyloxy", as used herein, means an arylcarbonyl group, as defined herein, appended to the parent molecular moiety through an oxygen atom. Representative examples of arylcarbonyloxy include, but are not limited to, phenylcarbonyloxy.

The term "arylene" is art-recognized, and, as used herein, pertains to a bidentate moiety obtained by removing two hydrogen atoms of an aryl ring, as defined above.

The term "arylalkyl" or "aralkyl", as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "azido", as used herein, refers to —N$_3$.

The term "carbamate", as used herein, refers to a moiety that may be represented by the general formula:

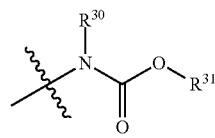

wherein R$^{30}$ and R$^{31}$ each independently represent hydrogen or a substituted or unsubstituted group selected from alkyl, cycloalkyl, cycloalkylalkyl, heterocyclyl, alkenyl, cycloalkenyl, aryl, heteroaryl, aralkyl, and heteroaralkyl. Nonlimiting examples of carbamate include those for which R$^{30}$ is hydrogen, and R$^{31}$ is selected from methyl, ethyl, propyl, isopropyl, propenyl, cyclohexyl, benzyl,

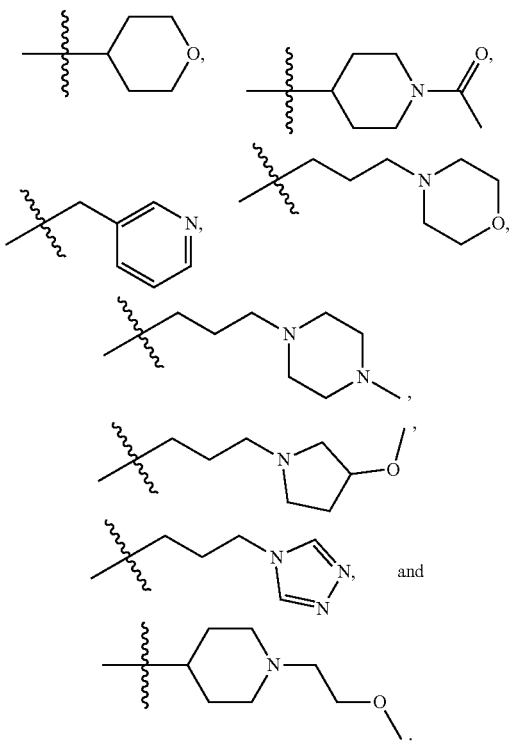

The term "carbonyl", as used herein, means a —C(=O)— group.

The term "carboxyl", as used herein, means a —CO$_2$H group.

The term "cyano", as used herein, means a —CN group.

The term "cycloalkylalkyl" as used herein, refers to a cycloalkyl group, as defined herein, appended to the parent molecular moiety through an alkyl group, also as defined herein.

The term "guanidinyl", as used herein, refers to a moiety that may be represented by the general formula:

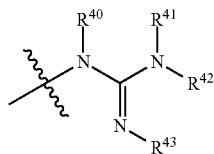

wherein $R^{40}$, $R^{41}$, $R^{42}$, and $R^{43}$ each independently represent hydrogen or a substituted or unsubstituted group selected from alkyl, cycloalkyl, cycloalkylalkyl, heterocyclyl, alkenyl, cycloalkenyl, aryl, heteroaryl, aralkyl, and heteroaralkyl. In one embodiment, $R^{40}$, $R^{41}$, $R^{42}$, and $R^{43}$ each represent hydrogen.

The term "halo" or "halogen" means —F, —Cl, —Br, or —I.

The term "haloalkyl" means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaralkyl", as used herein, means a heteroaryl, as defined herein, appended to the parent molecular moiety through an alkyl group, as defined herein. Representative examples of heteroarylalkyl include, but are not limited to, pyridin-3-ylmethyl and 2-(thien-2-yl)ethyl.

The term "heteroaryl", as used herein, includes aromatic ring systems, including, but not limited to, monocyclic, bicyclic, and tricyclic rings, and have 3 to 12 atoms including at least one heteroatom, such as nitrogen, oxygen, or sulfur. For purposes of exemplification, which should not be construed as limiting the scope of this invention, the following are examples of heteroaryl: azaindolyl, benzo(b)thienyl, benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, triazolyl or tropanyl. The heteroaryl groups may be substituted with 0, 1, 2, 3, 4 or 5 substituents independently selected from alkenyl, alkoxy, alkoxycarbonyl, alkoxysulfonyl, alkyl, alkylcarbonyl, alkylcarbonyloxy, alkylsulfonyl, alkylthio, alkynyl, amido, amino, carboxy, cyano, formyl, halo, haloalkoxy, haloalkyl, hydroxyl, hydroxyalkyl, mercapto, nitro, phosphinyl, silyl and silyloxy.

The term "heteroatom" is art-recognized and refers to an atom of any element other than carbon or hydrogen. Illustrative heteroatoms include boron, nitrogen, oxygen, phosphorus, sulfur, and selenium.

The term "heterocyclyl", as used herein, refers to non-aromatic ring systems, including, but not limited to, monocyclic, bicyclic, tricyclic and spirocyclic rings, which can be completely saturated or which can contain one or more units of unsaturation (for the avoidance of doubt, the degree of unsaturation does not result in an aromatic ring system) and have 3 to 12 atoms including at least one heteroatom, such as nitrogen, oxygen, or sulfur. For purposes of exemplification, which should not be construed as limiting the scope of this invention, the following are examples of heterocyclic rings: azepines, azetidinyl, morpholinyl, oxopiperidinyl, oxopyrrolidinyl, piperazinyl, piperidinyl, pyrrolidinyl, quinicludinyl, thiomorpholinyl, tetrahydropyranyl and tetrahydrofuranyl. The heterocyclyl groups may be substituted with 0, 1, 2, 3, 4 or 5 substituents independently selected from alkenyl, alkoxy, alkoxycarbonyl, alkoxysulfonyl, alkyl, alkylcarbonyl, alkylcarbonyloxy, alkyl sulfonyl, alkylthio, alkynyl, amido, amino, carboxy, cyano, formyl, halo, haloalkoxy, haloalkyl, hydroxyl, hydroxyalkyl, mercapto, nitro, phosphinyl, silyl and silyloxy.

The term "hydroxyl", as used herein, means an —OH group.

The term "hydroxyalkyl", as used herein, means at least one hydroxy group, as defined herein, is appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "nitro", as used herein, means a —NO$_2$ group.

The term "silyl", as used herein, includes hydrocarbyl derivatives of the silyl (H$_3$Si—) group (i.e., (hydrocarbyl)$_3$Si—), wherein a hydrocarbyl groups are univalent groups formed by removing a hydrogen atom from a hydrocarbon, e.g., ethyl, phenyl. The hydrocarbyl groups can be combinations of differing groups which can be varied in order to provide a number of silyl groups, such as trimethylsilyl (TMS), tert-butyldiphenylsilyl (TBDPS), tert-butyldimethylsilyl (TBS/TBDMS), triisopropylsilyl (TIPS), and [2-(trimethylsilyl)ethoxy]methyl (SEM).

The term "silyloxy", as used herein, means a silyl group, as defined herein, is appended to the parent molecule through an oxygen atom.

The term "sulfhydryl", as used herein, means a —SH group.

The term "sulfonyl" is art-recognized and refers to —SO$_2^-$.

The term "urea", as used herein, means a moiety that may be represented by the general formula:

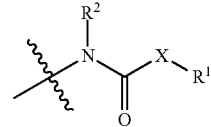

wherein X is —N(R$^2$)—;

R$^1$ is a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, acyl, amino, amido, aminoalkyl, and alkoxyl; or —N(R$^1$)(R$^2$) may represent a substituted or unsubstituted 3- to 10-membered heterocyclic ring, wherein said ring is monocyclic, bicyclic, tricyclic, or spirocyclic;

R$^2$ is independently hydrogen or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, acyl, amino, amido, aminoalkyl, and alkoxyl.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*.

Certain compounds contained in compositions of the invention may exist in particular geometric or stereoisomeric forms. In addition, polymers of the invention may also be optically active. The invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, alkyl, alkenyl, alkynyl, aryl, aralkyl, heterocyclyl, (heterocyclyl)alkyl, (cycloalkyl)alkyl, alkoxy, aryloxy, alkoxycarbonyl, alkoxysulfonyl, aryloxycarbonyl, aryloxysulfonyl, alkylcarbonyl, arylcarbonyl, alkylcarbonyloxy, arylcarbonyloxy, alkylsulfonyl, arylsulfonyl, alkylsulfonyloxy, arylsulfonyloxy, alkylthio, arylthio, amido, amino, carboxy, cyano, formyl, halo, haloalkoxy, haloalkyl, hydroxyl, hydroxyalkyl, mercapto, nitro, phosphinyl, acyl, acyloxy, silyl and silyloxy. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group", as used herein, means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis, 2$^{nd}$ ed.*; Wiley: New York, 1991). Protected forms of the inventive compounds are included within the scope of this invention.

For purposes of this invention, the chemical elements are identified in accordance with the Periodic Table of the Elements, CAS version, Handbook of Chemistry and Physics, 67th Ed., 1986-87, inside cover.

Compounds of the Invention

The invention provides a number of derivatives of AmB, including derivatives characterized by (i) certain modifications at C13; (ii) certain N modifications at C3'; (iii) certain urea derivatives at C16; and (iv) the combination of certain urea derivatives at C16 and C2'epiAmB.

For example, the invention provides a number of derivatives of AmB, including derivatives characterized by (i) certain modifications at C13; (ii) certain N modifications at C3'; (iii) certain urea derivatives at C16; and (iv) the combination of certain urea derivatives at C16 and C2'epiAmB.

An aspect of the invention is a compound represented by Formula (I) or a pharmaceutically acceptable salt thereof:

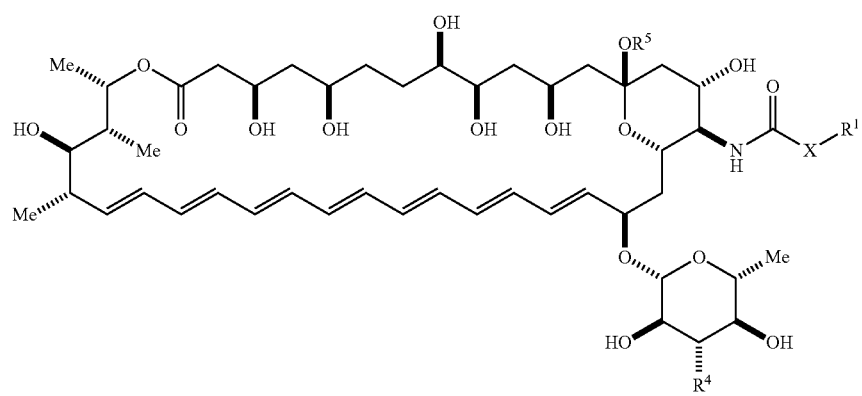

wherein, independently for each occurrence:

X is —N(R²)—;

R¹ is a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, acyl, amino, amido, aminoalkyl, and alkoxyl; or R¹ and R², together with the nitrogen to which they are attached, may form a substituted or unsubstituted 3- to 10-membered heterocyclic ring, wherein said ring is monocyclic, bicyclic, tricyclic, or spirocyclic;

R² is hydrogen or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, acyl, amino, amido, aminoalkyl, and alkoxyl;

R⁴ is selected from the group consisting of secondary amino, tertiary amino, amido, azido, isonitrile, nitro, urea, isocyanate, carbamate, and guanidinyl; and R⁵ is selected from the group consisting of hydrogen, alkyl, and haloalkyl.

In certain embodiments, R² is hydrogen.

In certain embodiments, —XR¹ is selected from the group consisting of —NHCH₂CH₃, —NHCH₂CH₂CH₃, —NHCH(CH₃)₂, —NH(2-butyl), —NHcyclopropyl, —NHcyclobutyl, —NHcyclopentyl, —NHcyclohexyl, —NHCH₃,

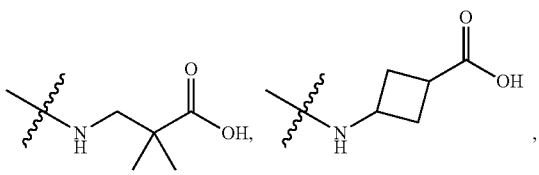

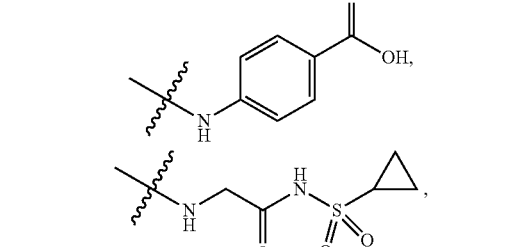

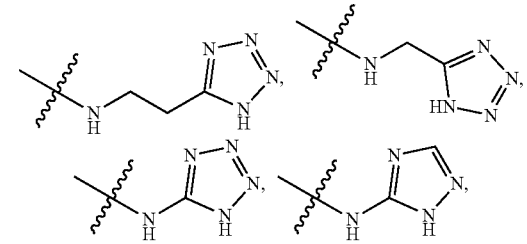

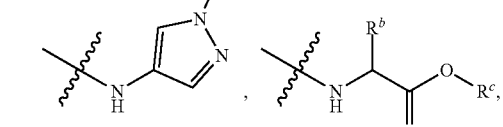

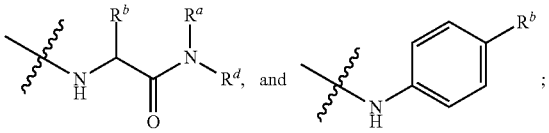

wherein, independently for each occurrence:

Rᵃ is hydrogen or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, acyl, amino, amido, aminoalkyl, and alkoxyl;

Rᵇ is hydrogen, halogen, hydroxyl, sulfhydryl, nitro, cyano, or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, carboxyl, acyl, acyloxy, amino, amido, azido, aminoalkyl, and alkoxyl;

Rᶜ is hydrogen or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, acyl, amino, amido, and aminoalkyl; and Rᵈ is hydrogen or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, acyl, amino, amido, aminoalkyl, and alkoxyl; or, when —XR¹ is

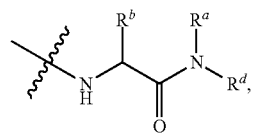

Rᵃ and Rᵈ, together with the nitrogen to which they are attached, may form a substituted or unsubstituted 3- to 10-membered heterocyclic ring, wherein said ring is monocyclic, bicyclic, tricyclic, or spirocyclic.

In certain embodiments, —XR¹ is selected from the group consisting of

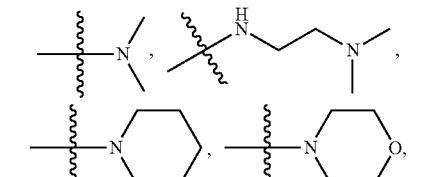

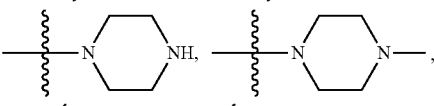

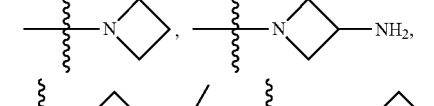

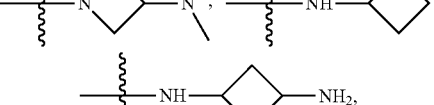

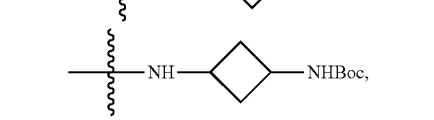

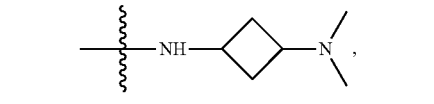

In certain embodiments, —XR[1] is selected from the group consisting of

In certain embodiments, —XR[1] is selected from the group consisting of —NHCH$_2$CH$_3$, —NHCH$_2$CH$_2$CH$_3$, —NHCH(CH$_3$)$_2$, —NH(2-butyl), —NHcyclopropyl, —NHcyclobutyl, —NHcyclopentyl, —NHcyclohexyl,

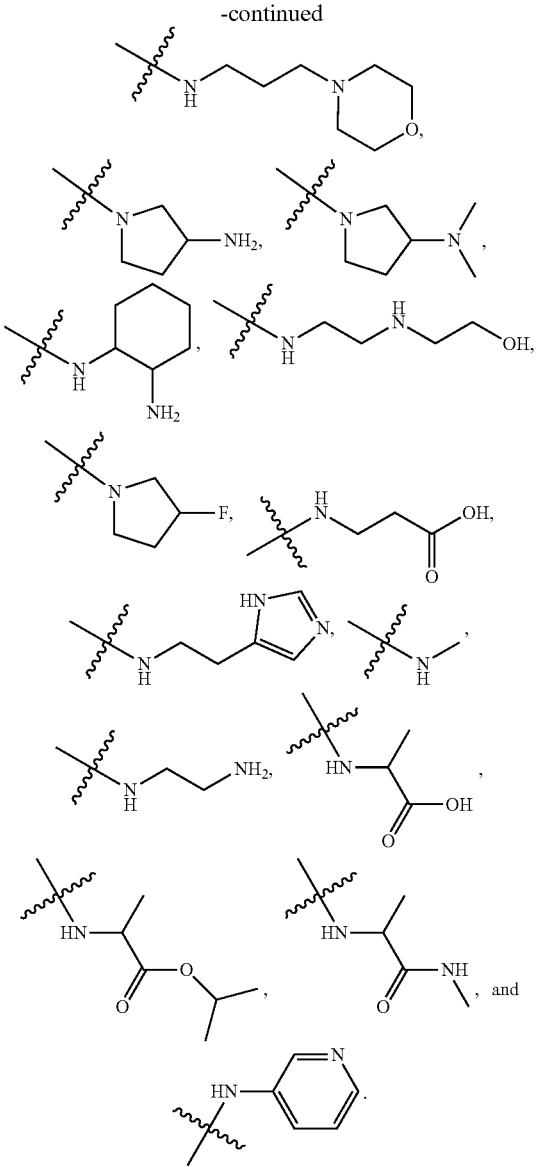

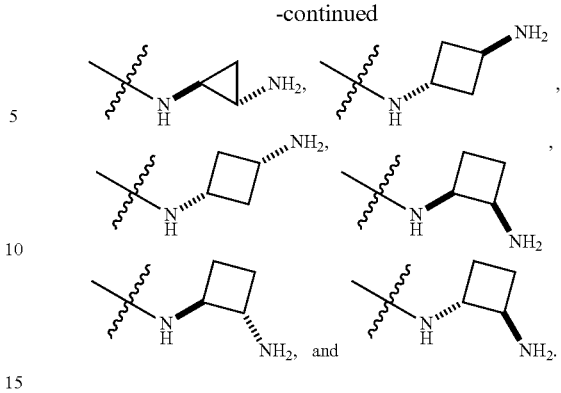

In certain embodiments, $R^4$ is secondary amino.
In certain embodiments, $R^4$ is tertiary amino.
In certain embodiments, $R^4$ is amido.
In certain embodiments, $R^4$ is azido.
In certain embodiments, $R^4$ is isonitrile.
In certain embodiments, $R^4$ is nitro.
In certain embodiments, $R^4$ is urea.
In certain embodiments, $R^4$ is isocyanate.
In certain embodiments, $R^4$ is carbamate.
In certain embodiments, $R^4$ is guanidinyl.
In certain embodiments, $R^4$ is selected from the group consisting of

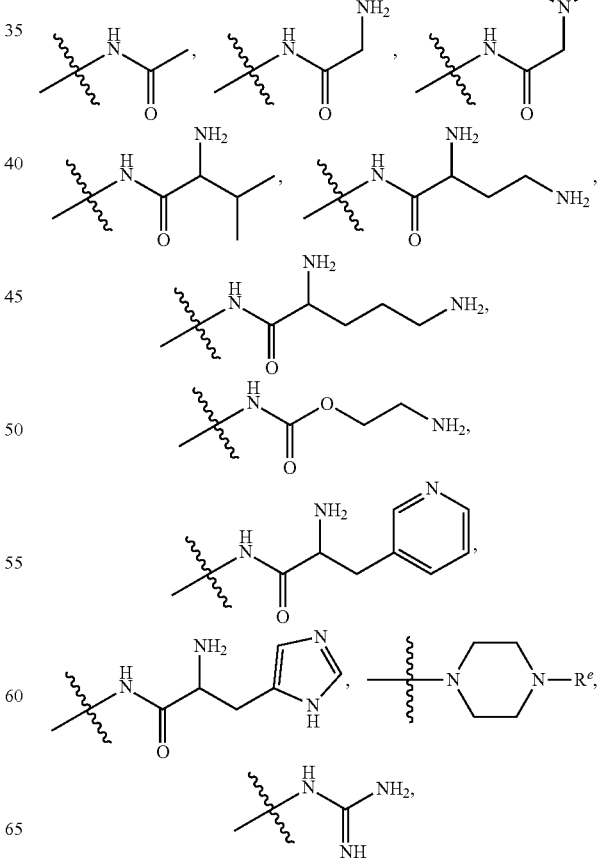

In certain embodiments, —$XR^1$ is selected from the group consisting of

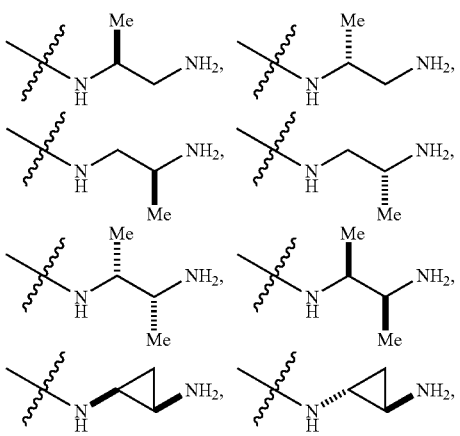

-continued

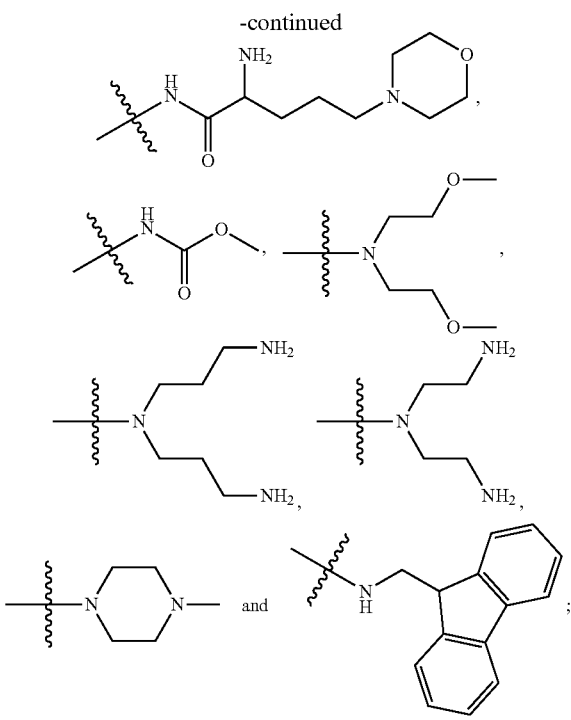

wherein
R$^e$ is hydrogen or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, acyl, amino, amido, aminoalkyl, and alkoxyl.

In certain embodiments, R$^5$ is hydrogen.
In certain embodiments, R$^5$ is alkyl.
In certain embodiments, R$^5$ is haloalkyl.

An aspect of the invention is a compound represented by Formula (IV) or a pharmaceutically acceptable salt thereof:

substituted or unsubstituted 3- to 10-membered heterocyclic ring, wherein said ring is monocyclic, bicyclic, tricyclic, or spirocyclic;

R$^2$ is hydrogen or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, acyl, amino, amido, aminoalkyl, and alkoxyl;

R$^5$ is selected from the group consisting of hydrogen, alkyl, and haloalkyl;

R$^6$ is C(O)OR$^f$; and

R$^f$ is selected from the group consisting of 2-alken-1-yl, tert-butyl, benzyl and fluorenylmethyl.

In certain embodiments, R$^2$ is hydrogen.

In certain embodiments, —XR$^1$ is selected from the group consisting of —NHCH$_2$CH$_3$, —NHCH$_2$CH$_2$CH$_3$, —NHCH(CH$_3$)$_2$, —NH(2-butyl), —NHcyclopropyl, —NHcyclobutyl, —NHcyclopentyl, —NHcyclohexyl, —NHCH$_3$,

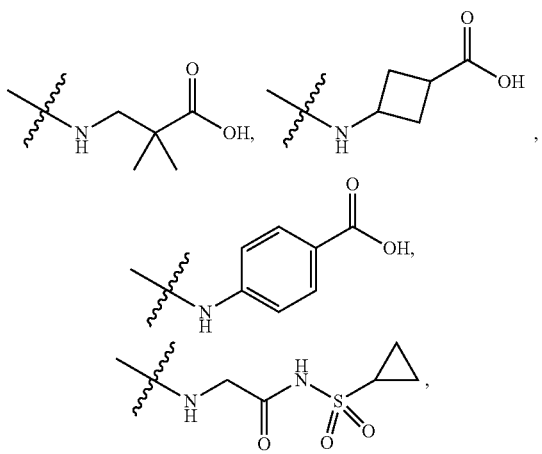

(IV)

[Structure of Formula (IV)]

wherein:
X is —N(R$^2$)—;
R$^1$ is a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, acyl, amino, amido, aminoalkyl, and alkoxyl; or R$^1$ and R$^2$, together with the nitrogen to which they are attached, may form a -continued

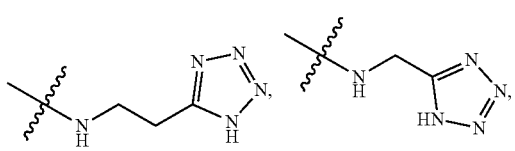

-continued

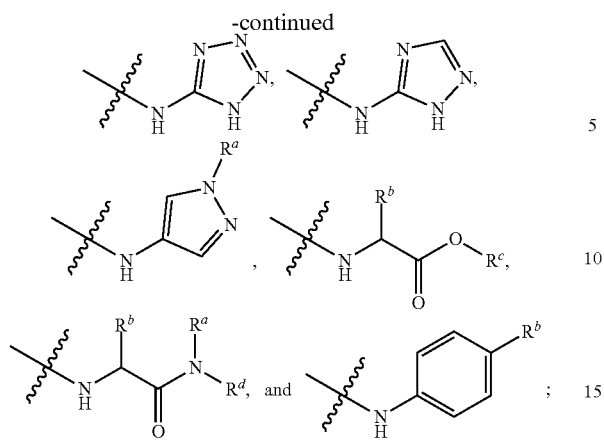

wherein, independently for each occurrence:

$R^a$ is hydrogen or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, acyl, amino, amido, aminoalkyl, and alkoxyl;

$R^b$ is hydrogen, halogen, hydroxyl, sulfhydryl, nitro, cyano, or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, carboxyl, acyl, acyloxy, amino, amido, azido, aminoalkyl, and alkoxyl;

$R^c$ is hydrogen or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, acyl, amino, amido, and aminoalkyl; and $R^d$ is hydrogen or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, acyl, amino, amido, aminoalkyl, and alkoxyl; or, when —$XR^1$ is

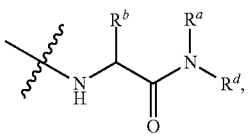

$R^a$ and $R^d$, together with the nitrogen to which they are attached, may form a substituted or unsubstituted 3- to 10-membered heterocyclic ring, wherein said ring is monocyclic, bicyclic, tricyclic, or spirocyclic.

In certain embodiments, —$XR^1$ is selected from the group consisting of

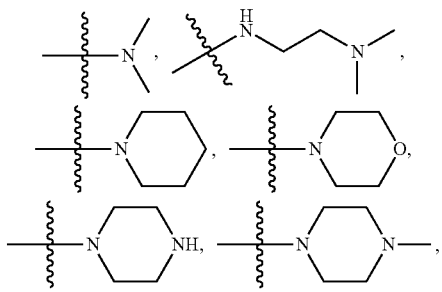

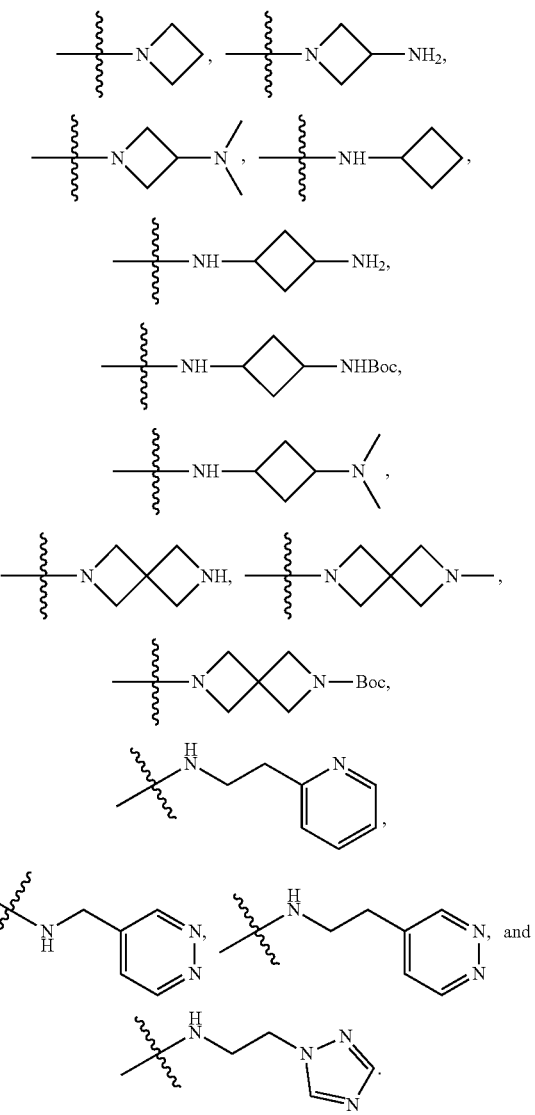

In certain embodiments, —$XR^1$ is selected from the group consisting of

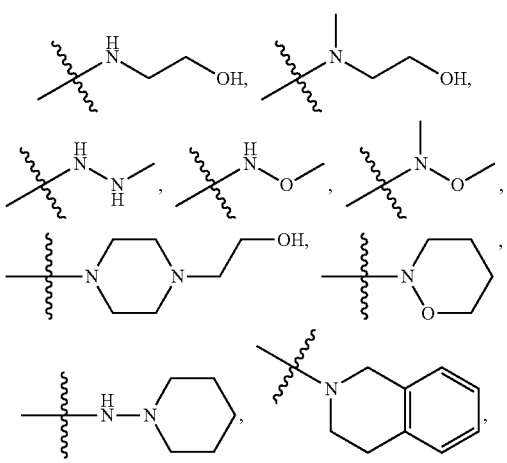

-continued
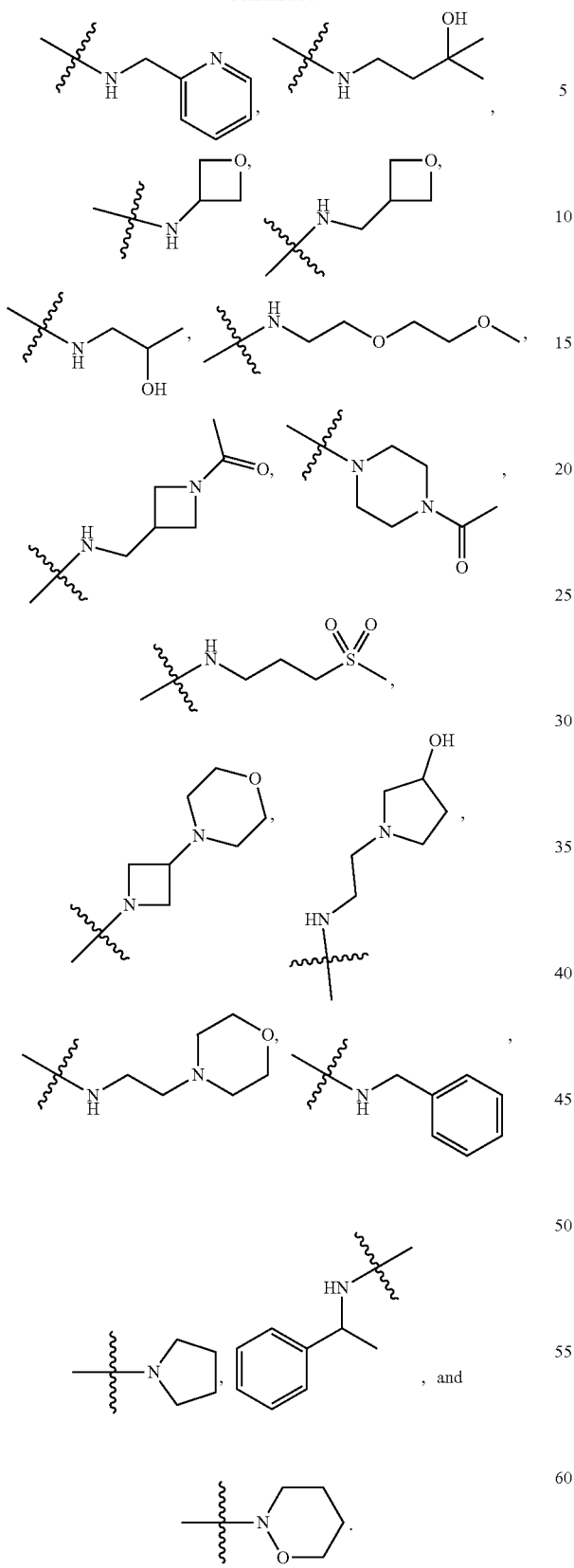
In certain embodiments, —XR$^1$ is selected from the group consisting of
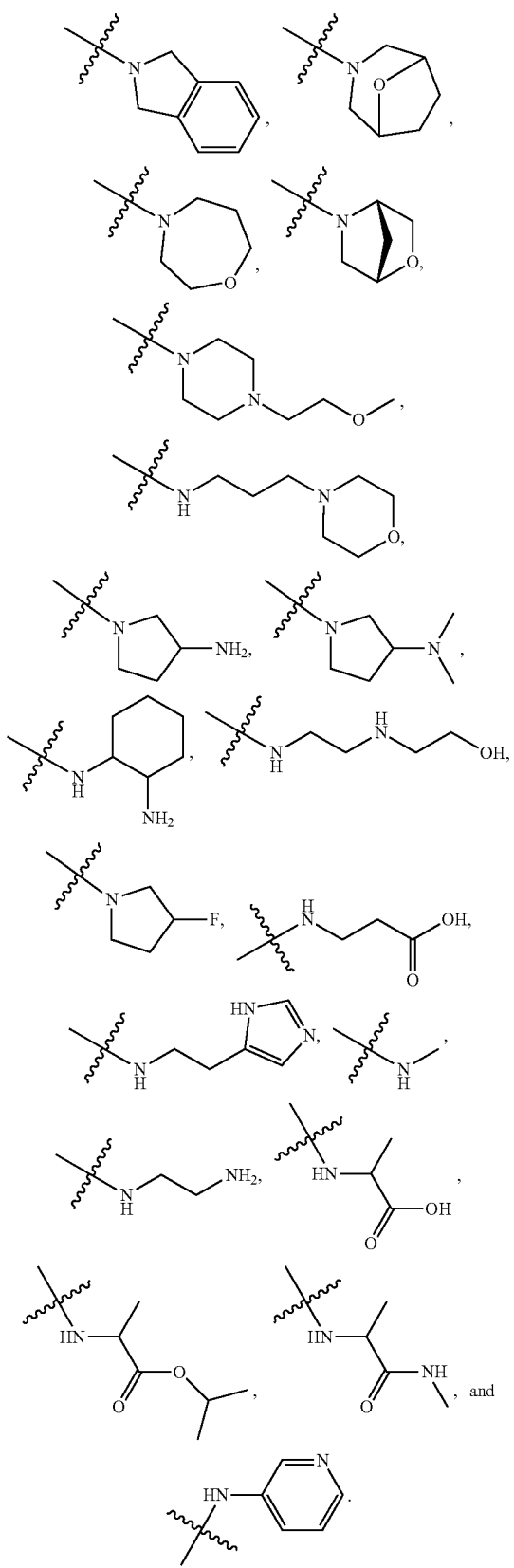
In certain embodiments, —XR$^1$ is selected from the group consisting of

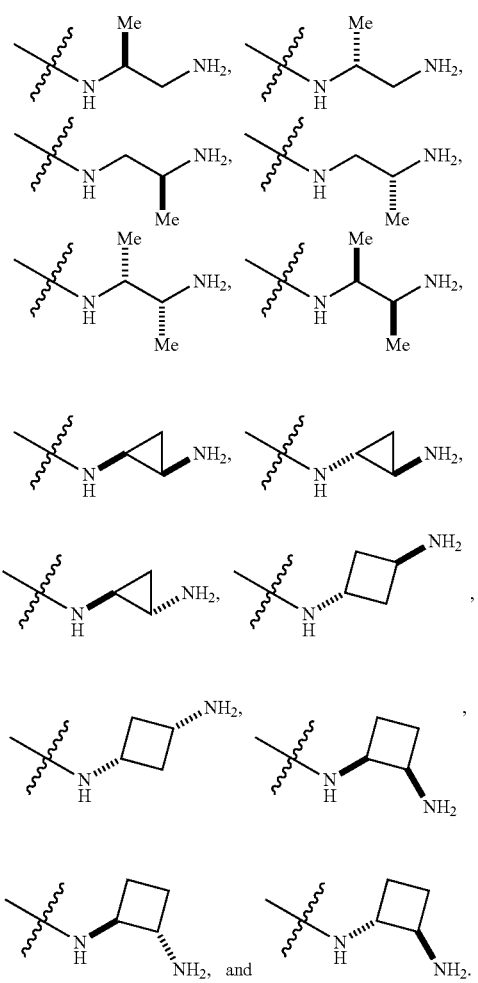

In certain embodiments, R⁵ is hydrogen.
In certain embodiments, R⁵ is alkyl.
In certain embodiments, R⁵ is haloalkyl.
In certain embodiments, R^f is 2-alken-1-yl.
In certain embodiments, R^f is tert-butyl.
In certain embodiments, R^f is benzyl.
In certain embodiments, R^f is fluorenylmethyl.

An aspect of the invention is a compound represented by Formula (V) or a pharmaceutically acceptable salt thereof:

wherein:

R⁵ is selected from the group consisting of hydrogen, alkyl, and haloalkyl;

—XR¹ is selected from the group consisting of

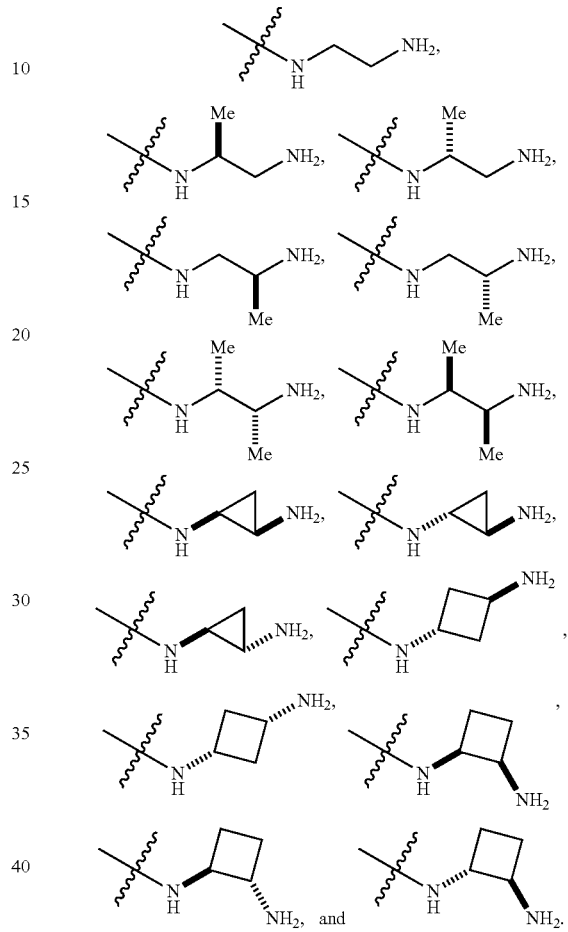

In certain embodiments, R⁵ is hydrogen.
In certain embodiments, R⁵ is alkyl.
In certain embodiments, R⁵ is haloalkyl.

(V)

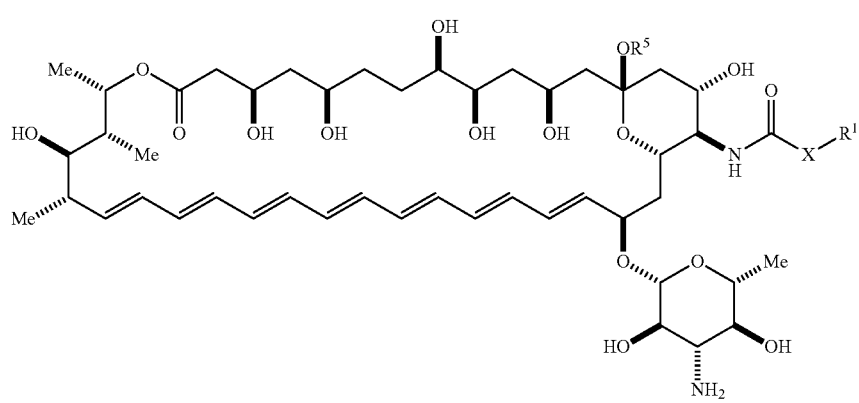

In certain embodiments, —XR¹ is

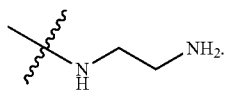 [SMILES: *NCCN]

In certain embodiments, R⁵ is hydrogen; and —XR¹ is

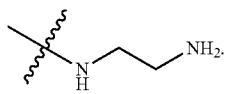 [SMILES: *NCCN]

An aspect of the invention is a compound represented by Formula (II) or a pharmaceutically acceptable salt thereof:

(II)

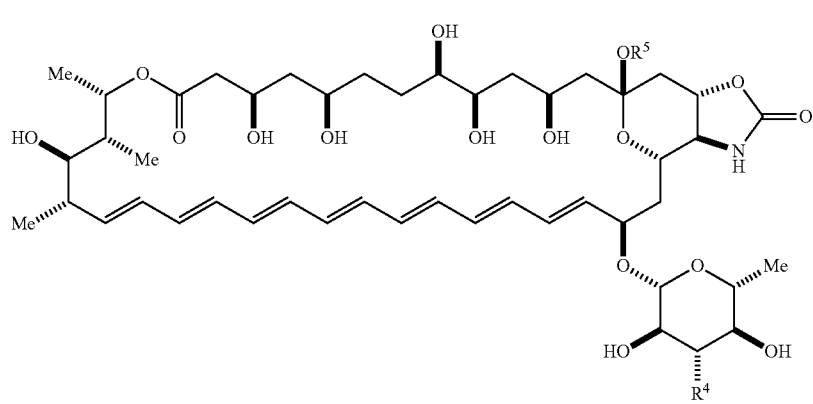

wherein, independently for each occurrence:
R⁴ is selected from the group consisting of primary amino, secondary amino, tertiary amino, amido, azido, isonitrile, nitro, urea, isocyanate, carbamate, and guanidinyl; and
R⁵ is selected from the group consisting of hydrogen, alkyl, and haloalkyl.

In certain embodiments, R⁴ is primary amino.
In certain embodiments, R⁴ is secondary amino.
In certain embodiments, R⁴ is tertiary amino.
In certain embodiments, R⁴ is amido.
In certain embodiments, R⁴ is azido.
In certain embodiments, R⁴ is isonitrile.
In certain embodiments, R⁴ is nitro.
In certain embodiments, R⁴ is urea.
In certain embodiments, R⁴ is isocyanate.
In certain embodiments, R⁴ is carbamate.
In certain embodiments, R⁴ is guanidinyl.
In certain embodiments, R⁴ is selected from the group consisting of

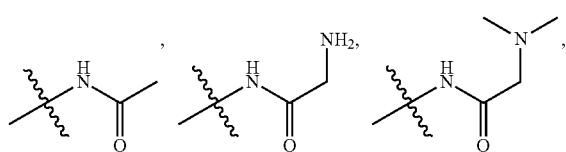

-continued

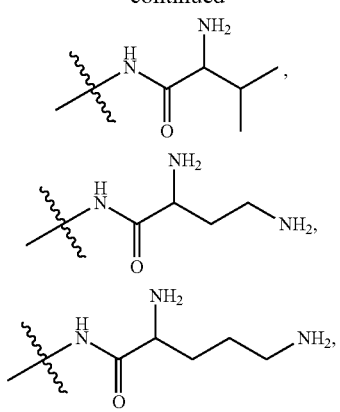

-continued

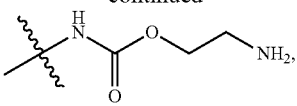

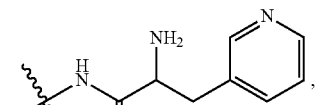

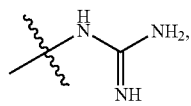

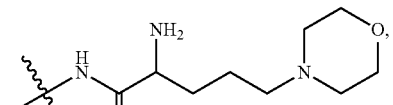

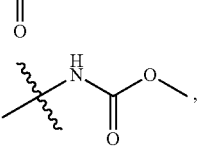

-continued

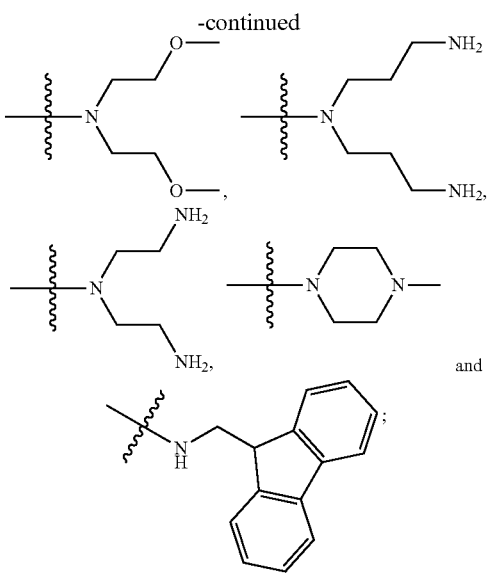

wherein

R$^e$ is hydrogen or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, acyl, amino, amido, aminoalkyl, and alkoxyl.

In certain embodiments, R$^5$ is hydrogen.
In certain embodiments, R$^5$ is alkyl.
In certain embodiments, R$^5$ is haloalkyl.

An aspect of the invention is a compound represented by Formula (III) or a pharmaceutically acceptable salt thereof:

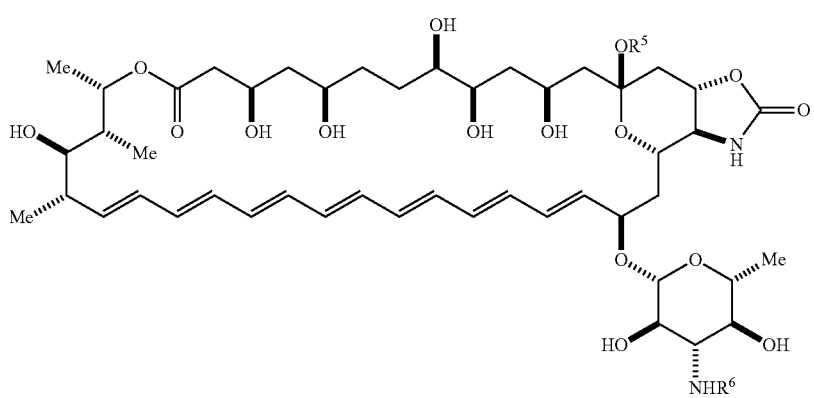

wherein:
R$^5$ is selected from the group consisting of hydrogen, alkyl, and haloalkyl;
R$^6$ is —C(O)OR$^f$; and
R$^f$ is selected from the group consisting of 2-alken-1-yl, tert-butyl, benzyl and fluorenylmethyl.
In certain embodiments, R$^5$ is hydrogen.
In certain embodiments, R$^5$ is alkyl.
In certain embodiments, R$^5$ is haloalkyl.
In certain embodiments, R$^f$ is 2-alken-1-yl.
In certain embodiments, R$^f$ is tert-butyl.
In certain embodiments, R$^f$ is benzyl.
In certain embodiments, R$^f$ is fluorenylmethyl.

Pharmaceutical Compositions

The invention also provides pharmaceutical compositions and methods for making same.

An aspect of the invention is a pharmaceutical composition comprising a compound of the invention; and a pharmaceutically acceptable carrier. In certain embodiments, the invention is a pharmaceutical composition, comprising a compound of the invention, or a pharmaceutically acceptable salt thereof, and a pharmaceutically acceptable carrier. The term "pharmaceutically acceptable carrier" means one or more compatible solid or liquid filler, diluent, or encapsulating substances which are suitable for administration to a human or other vertebrate animal. The term "carrier" denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficacy.

In certain embodiments, the pharmaceutical composition is an intravenous dosage form.

In certain embodiments, the pharmaceutical composition is an oral dosage form.

In certain embodiments, the pharmaceutical composition is a lyophilized preparation of a liposome-intercalated or liposome-encapsulated active compound.

In certain embodiments, the pharmaceutical composition is a lipid complex of the compound in aqueous suspension.

The foregoing embodiments of pharmaceutical compositions of the invention are meant to be exemplary and are not limiting.

Also provided is a method for making such pharmaceutical compositions. The method comprises placing a compound of the invention, or a pharmaceutically acceptable salt thereof, in a pharmaceutically acceptable carrier.

Methods of the Invention

Compounds of the invention are useful for inhibiting growth of fungi and yeast, including, in particular, fungi and yeast of clinical significance as pathogens. Advantageously, the compounds of the invention have improved therapeutic indices compared to AmB, thereby providing agents with improved efficacy and reduced toxicity as compared to AmB. Compounds of the invention are useful in methods of treating fungal and yeast infections, including, in particular, systemic fungal and yeast infections. Compounds of the invention are also useful in the manufacture of medicaments for treating fungal and yeast infections, including, in particular, systemic fungal and yeast infections. The invention further provides the use of compounds of the invention for the treatment of fungal and yeast infections, including, in particular, systemic fungal and yeast infections.

An aspect of the invention is a method of treating a fungal infection, comprising administering to a subject in need thereof a therapeutically effective amount of a compound of the invention, thereby treating the fungal infection.

As used herein, "inhibit" or "inhibiting" means reduce by an objectively measureable amount or degree compared to control. In one embodiment, inhibit or inhibiting means reduce by at least a statistically significant amount compared to control. In one embodiment, inhibit or inhibiting means reduce by at least 5 percent compared to control. In various individual embodiments, inhibit or inhibiting means reduce by at least 10, 15, 20, 25, 30, 33, 40, 50, 60, 67, 70, 75, 80, 90, or 95 percent (%) compared to control.

As used herein, the terms "treat" and "treating" refer to performing an intervention that results in (a) preventing a condition or disease from occurring in a subject that may be at risk of developing or predisposed to having the condition or disease but has not yet been diagnosed as having it; (b) inhibiting a condition or disease, e.g., slowing or arresting its development; or (c) relieving or ameliorating a condition or disease, e.g., causing regression of the condition or disease. In one embodiment the terms "treating" and "treat" refer to performing an intervention that results in (a) inhibiting a condition or disease, e.g., slowing or arresting its development; or (b) relieving or ameliorating a condition or disease, e.g., causing regression of the condition or disease. For example, in one embodiment the terms "treating" and "treat" refer to performing an intervention that results in (a) inhibiting a fungal infection, e.g., slowing or arresting its development; or (b) relieving or ameliorating a fungal infection, e.g., causing regression of the fungal infection.

A "fungal infection" as used herein refers to an infection in or of a subject with a fungus as defined herein. In one embodiment the term "fungal infection" includes a yeast infection. A "yeast infection" as used herein refers to an infection in or of a subject with a yeast as defined herein.

As used herein, a "subject" refers to a living mammal. In various embodiments a subject is a non-human mammal, including, without limitation, a mouse, rat, hamster, guinea pig, rabbit, sheep, goat, cat, dog, pig, horse, cow, or non-human primate. In one embodiment a subject is a human.

As used herein, a "subject having a fungal infection" refers to a subject that exhibits at least one objective manifestation of a fungal infection. In one embodiment a subject having a fungal infection is a subject that has been diagnosed as having a fungal infection and is in need of treatment thereof. Methods of diagnosing a fungal infection are well known and need not be described here in any detail.

As used herein, a "subject having a yeast infection" refers to a subject that exhibits at least one objective manifestation of a yeast infection. In one embodiment a subject having a yeast infection is a subject that has been diagnosed as having a yeast infection and is in need of treatment thereof. Methods of diagnosing a yeast infection are well known and need not be described here in any detail.

In certain embodiments, the compound is administered intravenously.

In certain embodiments, the compound is administered orally.

In certain embodiments, the compound is administered systemically.

In certain embodiments, the compound is administered parenterally.

In certain embodiments, the compound is administered intraperitoneally.

In certain embodiments, the compound is administered enterally.

In certain embodiments, the compound is administered intraocularly.

In certain embodiments, the compound is administered topically.

Additional routes of administration of compounds of the invention are contemplated by the invention, including, without limitation, intravesicularly (urinary bladder), pulmonary, and intrathecally.

As used herein, the phrase "effective amount" refers to any amount that is sufficient to achieve a desired biological effect.

As used herein, the phrase "therapeutically effective amount" refers to an amount that is sufficient to achieve a desired therapeutic effect, e.g., to treat a fungal or yeast infection.

For any compound described herein, a therapeutically effective amount can, in general, be initially determined from in vitro studies, animal models, or both in vitro studies and animal models. In vitro methods are well known and can include determination of minimum inhibitory concentration (MIC), minimum fungicidal concentration (MFC), concentration at which growth is inhibited by 50 percent ($IC_{50}$), concentration at which growth is inhibited by 90 percent ($IC_{90}$), and the like. A therapeutically effective amount can also be determined from human data for compounds of the invention which have been tested in humans and for compounds which are known to exhibit similar pharmacological activities, such as other related active agents (e.g., AmB). Higher doses may be required for parenteral administration. The applied dose can be adjusted based on the relative bioavailability and potency of the administered compound. Adjusting the dose to achieve maximal efficacy based on the methods described herein and other methods as are well-known in the art is well within the capabilities of the ordinarily skilled artisan.

For any compound described herein, a therapeutically effective amount for use in human subjects can be initially determined from in vitro studies, animal models, or both in vitro studies and animal models. A therapeutically effective amount for use in human subjects can also be determined from human data for compounds of the invention which have been tested in humans and for compounds which are known to exhibit similar pharmacological activities, such as other related active agents (e.g., AmB). Higher doses may be required for parenteral administration. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

Dosing and Formulation

Compounds of the invention can be combined with other therapeutic agents. The compound of the invention and other therapeutic agent may be administered simultaneously or sequentially. When the other therapeutic agents are administered simultaneously, they can be administered in the same or separate formulations, but they are administered substantially at the same time. The other therapeutic agents are administered sequentially with one another and with compound of the invention, when the administration of the other therapeutic agents and the compound of the invention is temporally separated. The separation in time between the administration of these compounds may be a matter of minutes or it may be longer.

Examples of other therapeutic agents include other antifungal agents, including AmB, as well as other antibiotics, anti-viral agents, anti-inflammatory agents, immunosuppressive agents, and anti-cancer agents.

As stated above, an "effective amount" refers to any amount that is sufficient to achieve a desired biological effect. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial unwanted toxicity and yet is effective to treat the particular subject. The effective amount for any particular application can vary depending on such factors as the disease or condition being treated, the particular compound of the invention being administered, the size of the subject, or the severity of the disease or condition. One of ordinary skill in the art can empirically determine the effective amount of a particular compound of the invention and/or other therapeutic agent without necessitating undue experimentation. It is preferred generally that a maximum dose be used, that is, the highest safe dose according to some medical judgment. Multiple doses per day may be contemplated to achieve appropriate systemic levels of compounds. Appropriate systemic levels can be determined by, for example, measurement of the patient's peak or sustained plasma level of the drug. "Dose" and "dosage" are used interchangeably herein.

Generally, daily oral doses of active compounds will be, for human subjects, from about 0.01 milligrams/kg per day to 1000 milligrams/kg per day. It is expected that oral doses in the range of 0.5 to 50 milligrams/kg, in one or several administrations per day, will yield the desired results. Dosage may be adjusted appropriately to achieve desired drug levels, local or systemic, depending upon the mode of administration. For example, it is expected that intravenous administration would be from one order to several orders of magnitude lower dose per day. In the event that the response in a subject is insufficient at such doses, even higher doses (or effective higher doses by a different, more localized delivery route) may be employed to the extent that patient tolerance permits. Multiple doses per day are contemplated to achieve appropriate systemic levels of compounds.

In one embodiment, intravenous administration of a compound of the invention may typically be from 0.1 mg/kg/day to 20 mg/kg/day. Intravenous dosing thus may be similar to, or advantageously, may exceed maximal tolerated doses of AmB. Intravenous dosing also may be similar to, or advantageously, may exceed maximal tolerated daily doses of AmB. Intravenous dosing also may be similar to, or advantageously, may exceed maximal tolerated cumulative doses of AmB.

Intravenous dosing also may be similar to, or advantageously, may exceed maximal recommended doses of AmB. Intravenous dosing also may be similar to, or advantageously, may exceed maximal recommended daily doses of AmB. Intravenous dosing also may be similar to, or advantageously, may exceed maximal recommended cumulative doses of AmB.

For any compound described herein the therapeutically effective amount can be initially determined from animal models. A therapeutically effective dose can also be determined from human data for compounds of the invention which have been tested in humans and for compounds which are known to exhibit similar pharmacological activities, such as other related active agents. Higher doses may be required for parenteral administration. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

Amphotericin B is commercially available in a number of formulations, including deoxycholate-based (sometimes referred to as desoxycholate-based) formulations and lipid-based (including liposomal) formulations. Amphotericin B derivative compounds of the invention similarly may be formulated, for example, and without limitation, as deoxycholate-based formulations and lipid-based (including liposomal) formulations.

For use in therapy, an effective amount of the compound of the invention can be administered to a subject by any mode that delivers the compound of the invention to the desired surface. Administering the pharmaceutical composition of the present invention may be accomplished by any means known to the skilled artisan. Routes of administration include but are not limited to oral, intravenous, intramuscular, intraperitoneal, subcutaneous, direct injection (for example, into a tumor or abscess), mucosal, pulmonary (e.g., inhalation), and topical.

For intravenous and other parenteral routes of administration, the compounds of the invention generally may be formulated similarly to AmB. For example, a compound of the invention can be formulated as a lyophilized preparation with deoxycholic acid, as a lyophilized preparation of liposome-intercalated or -encapsulated active compound, as a lipid complex in aqueous suspension, or as a cholesteryl sulfate complex. Lyophilized formulations are generally reconstituted in suitable aqueous solution, e.g., in sterile water or saline, shortly prior to administration.

For oral administration, the compounds (i.e., compounds of the invention, and other therapeutic agents) can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, e.g., EDTA for neutralizing internal acid conditions or may be administered without any carriers.

Also specifically contemplated are oral dosage forms of the above component or components. The component or components may be chemically modified so that oral delivery of the derivative is efficacious. Generally, the chemical modification contemplated is the attachment of at least one moiety to the component molecule itself, where said moiety permits (a) inhibition of acid hydrolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, "Soluble Polymer-Enzyme Adducts", In: Enzymes as Drugs, Hocenberg and Roberts, eds., Wiley-Interscience, New York, N.Y., pp. 367-383 (1981); Newmark et al., *J Appl Biochem* 4: 185-9 (1982). Other polymers that could be used are poly-1,3-dioxolane and poly-1,3,6-tioxocane. Preferred for pharmaceutical usage, as indicated above, are polyethylene glycol moieties.

For the component (or derivative) the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the compound of the invention (or derivative) or by release of the biologically active material beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic (e.g., powder); for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the compound of the invention (or derivative) may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, α-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents which can be used and can include benzalkonium chloride and benzethonium chloride. Potential non-ionic detergents that could be included in the formulation as surfactants include lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the compound of the invention or derivative either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

Also contemplated herein is pulmonary delivery of the compounds of the invention (or derivatives thereof). The compound of the invention (or derivative) is delivered to the lungs of a mammal while inhaling and traverses across the lung epithelial lining to the blood stream. Other reports of inhaled molecules include Adjei et al., *Pharm Res* 7:565-569 (1990); Adjei et al., *Int J Pharmaceutics* 63:135-144 (1990) (leuprolide acetate); Braquet et al., *J Cardiovasc Pharmacol* 13 (suppl. 5):143-146 (1989) (endothelin-1); Hubbard et al., *Annal Int Med* 3:206-212 (1989) ($\alpha$1-antitrypsin); Smith et al., 1989, *J Clin Invest* 84:1145-1146 (a-1-proteinase); Oswein et al., 1990, "Aerosolization of Proteins", Proceedings of Symposium on Respiratory Drug Delivery II, Keystone, Colo., March, (recombinant human growth hormone); Debs et al., 1988, *J Immunol* 140:3482-3488 (interferon-gamma and tumor necrosis factor alpha) and Platz et al., U.S. Pat. No. 5,284,656 (granulocyte colony stimulating factor). A method and composition for pulmonary delivery of drugs for systemic effect is described in U.S. Pat. No. 5,451,569, issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of compound of the invention (or derivative). Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified compound of the invention may also be prepared in different formulations depending on the type of chemical modification or the type of device employed.

Formulations suitable for use with a nebulizer, either jet or ultrasonic, will typically comprise compound of the invention (or derivative) dissolved in water at a concentration of about 0.1 to 25 mg of biologically active compound of the invention per mL of solution. The formulation may also include a buffer and a simple sugar (e.g., for compound of the invention stabilization and regulation of osmotic pressure). The nebulizer formulation may also contain a surfactant, to reduce or prevent surface induced aggregation of the compound of the invention caused by atomization of the solution in forming the aerosol.

Formulations for use with a metered-dose inhaler device will generally comprise a finely divided powder containing the compound of the invention (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing compound of the invention (or derivative) and may also include a bulking agent, such as lactose, sorbitol, sucrose, or mannitol in amounts which facilitate dispersal of the powder from the device, e.g., 50 to 90% by weight of the formulation. The compound of the invention (or derivative) should advantageously be prepared in particulate form with an average particle size of less than 10 micrometers (μm), most preferably 0.5 to 5 μm, for most effective delivery to the deep lung.

Nasal delivery of a pharmaceutical composition of the present invention is also contemplated. Nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions, or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethylcellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described above, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer R, *Science* 249:1527-33 (1990), which is incorporated herein by reference.

The compounds of the invention and optionally other therapeutics may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

Pharmaceutical compositions of the invention contain an effective amount of a compound of the invention and optionally at least one additional therapeutic agent included in a pharmaceutically acceptable carrier.

The therapeutic agent(s), including specifically but not limited to the compound of the invention, may be provided in particles. Particles as used herein means nanoparticles or microparticles (or in some instances larger particles) which can consist in whole or in part of the compound of the invention or the other therapeutic agent(s) as described herein. The particles may contain the therapeutic agent(s) in a core surrounded by a coating, including, but not limited to, an enteric coating. The therapeutic agent(s) also may be dispersed throughout the particles. The therapeutic agent(s) also may be adsorbed into the particles. The particles may be of any order release kinetics, including zero-order release, first-order release, second-order release, delayed release, sustained release, immediate release, and any combination thereof, etc. The particle may include, in addition to the therapeutic agent(s), any of those materials routinely used in the art of pharmacy and medicine, including, but not limited to, erodible, nonerodible, biodegradable, or nonbiodegradable material or combinations thereof. The particles may be microcapsules which contain the compound of the invention in a solution or in a semi-solid state. The particles may be of virtually any shape.

Both non-biodegradable and biodegradable polymeric materials can be used in the manufacture of particles for delivering the therapeutic agent(s). Such polymers may be natural or synthetic polymers. The polymer is selected based on the period of time over which release is desired. Bioadhesive polymers of particular interest include bioerodible hydrogels described in Sawhney H S et al. (1993) *Macromolecules* 26:581-7, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly (butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The therapeutic agent(s) may be contained in controlled release systems. The term "controlled release" is intended to refer to any drug-containing formulation in which the manner and profile of drug release from the formulation are controlled. This refers to immediate as well as non-immediate release formulations, with non-immediate release formulations including but not limited to sustained release and delayed release formulations. The term "sustained release" (also referred to as "extended release") is used in its conventional sense to refer to a drug formulation that provides for gradual release of a drug over an extended period of time, and that preferably, although not necessarily, results in substantially constant blood levels of a drug over an extended time period. The term "delayed release" is used in its conventional sense to refer to a drug formulation in which there is a time delay between administration of the formulation and the release of the drug there from. "Delayed release" may or may not involve gradual release of drug over an extended period of time, and thus may or may not be "sustained release."

Use of a long-term sustained release implant may be particularly suitable for treatment of chronic conditions. "Long-term" release, as used herein, means that the implant is constructed and arranged to deliver therapeutic levels of the active ingredient for at least 7 days, and preferably 30-60 days. Long-term sustained release implants are well-known to those of ordinary skill in the art and include some of the release systems described above.

Exemplary Methods of Making Hybrid Amphotericin B Derivatives

The invention provides a number of derivatives of AmB, including derivatives characterized by (i) certain modifications at C13; (ii) certain N modifications at C3'; (iii) certain urea derivatives at C16; and (iv) the combination of certain urea derivatives at C16 and C2'epiAmB.

The invention describes a synthesis platform to make atomistic modifications of AmB, which led to the discovery that sterol binding, rather than membrane permeabilization, primarily drives cytocidal action. In certain embodiments, a new method for site-selective modification of AmB involves electronic tuning of acylation reagents to achieve site-discriminating transition states for acyl transfer which achieved site-selective acylations of the 10 hydroxyl groups appended to AmB. See Wilcock, B. C. et al., *Nat Chem* 2012, 4 (12), 996-1003, the teachings of which are incorporated herein by reference. This methodology allows efficient epimerization of a single stereogenic center at the C2'position of AmB, thus opening practical access to the non-toxic AmB derivatives. In certain embodiments, the highly complex macrolide skeleton of AmB is amenable to a tandem sequence involving Curtius rearrangement at C16 and trapping the resulting isocyanate by the C15-OH. This generates an isolable but conformationally strained and thus "spring-loaded" oxazolidinone intermediate poised for one-step late-stage transformation into a wide range of AmBUrea derivatives. See Davis, S. A. et al., *Nat Chem Biol* 2015, 11 (7), 481-7, the teachings of which are incorporated herein by reference. This chemistry allows the preparation of new hybrid C2'epiAmBUrea derivatives, C2'epiAmBAU. This new AmB derivative shows dramatically improved activity against both *Candida* and *Aspergillus* strains (up to >500 fold increase in potency), while maintaining a reduced toxicity profile. Thus, these new AmB derivatives allow a new high-dose treatment strategy to eradicate life-threatening invasive fungal infections with a significantly improved safety profile.

An aspect of the invention is a method of making a C16 urea derivative of C2'epi-Amphotericin B according to any one of the four transformations shown in Scheme 1:

Scheme 1

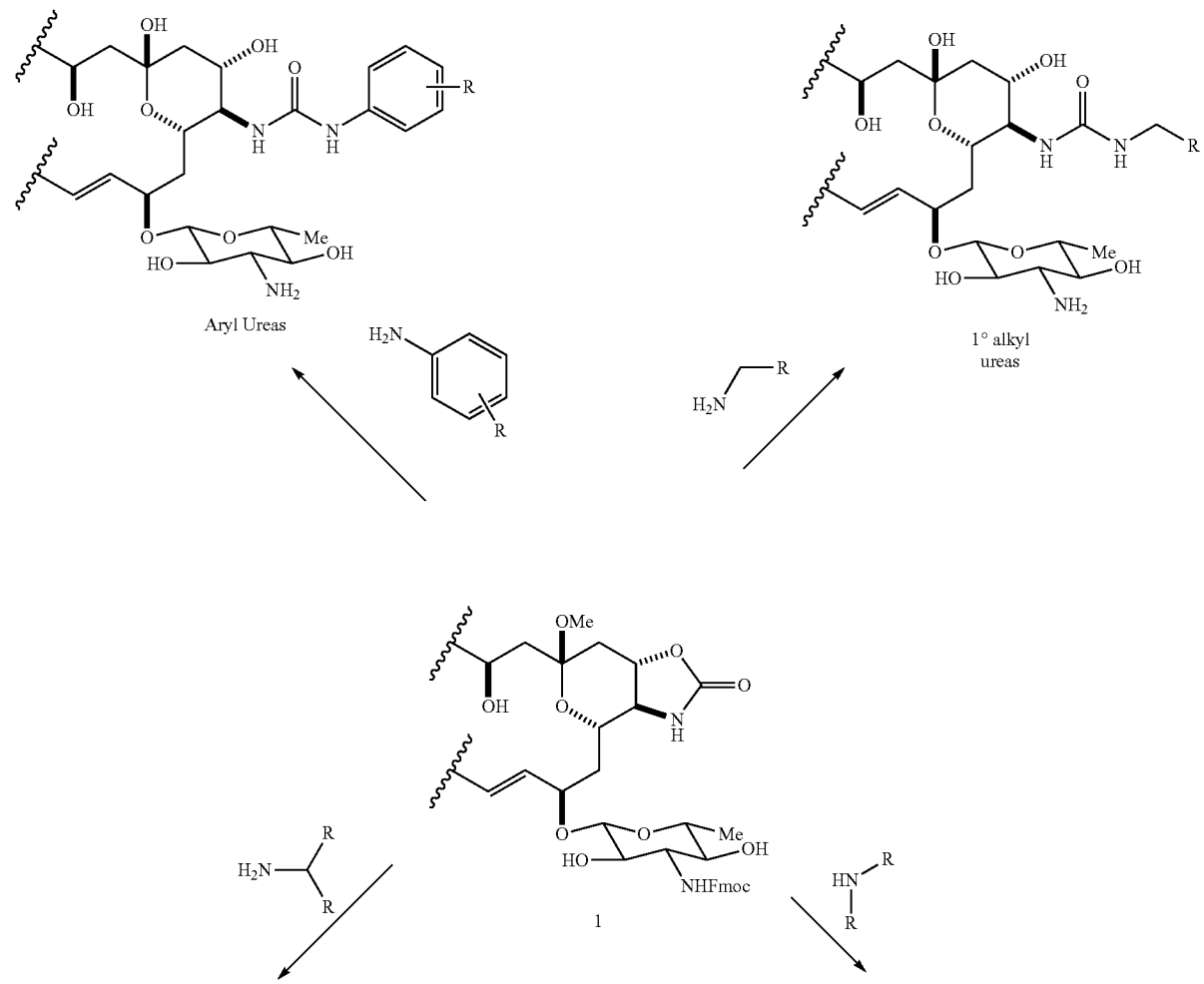

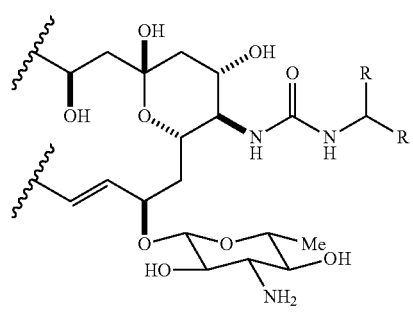

Branched Ureas

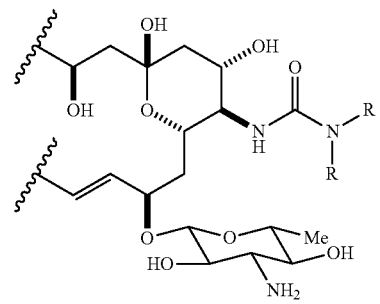

2° alkyl ureas wherein 1 represents

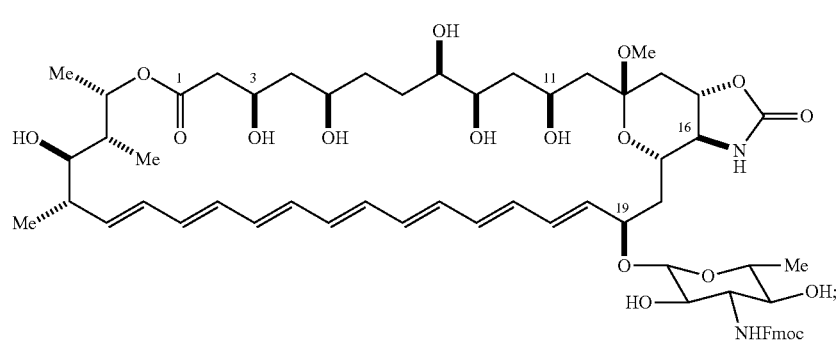

and each instance of R is independently selected from the group consisting of hydrogen, halogen, straight- and branched-chain alkyl, cycloalkyl, cycloalkylalkyl, heterocyclyl, aryl, heteroaryl, aralkyl, heteroaralkyl, hydroxyl, sulfhydryl, carboxyl, amino, amido, azido, nitro, cyano, aminoalkyl, and alkoxyl.

EXAMPLES

Having now described the present invention in detail, the same will be more clearly understood by reference to the following examples, which are included herewith for purposes of illustration only and are not intended to be limiting of the invention.

Example 1

Novel Chemical Design With No Mammalian Toxicity

Figure 1B:
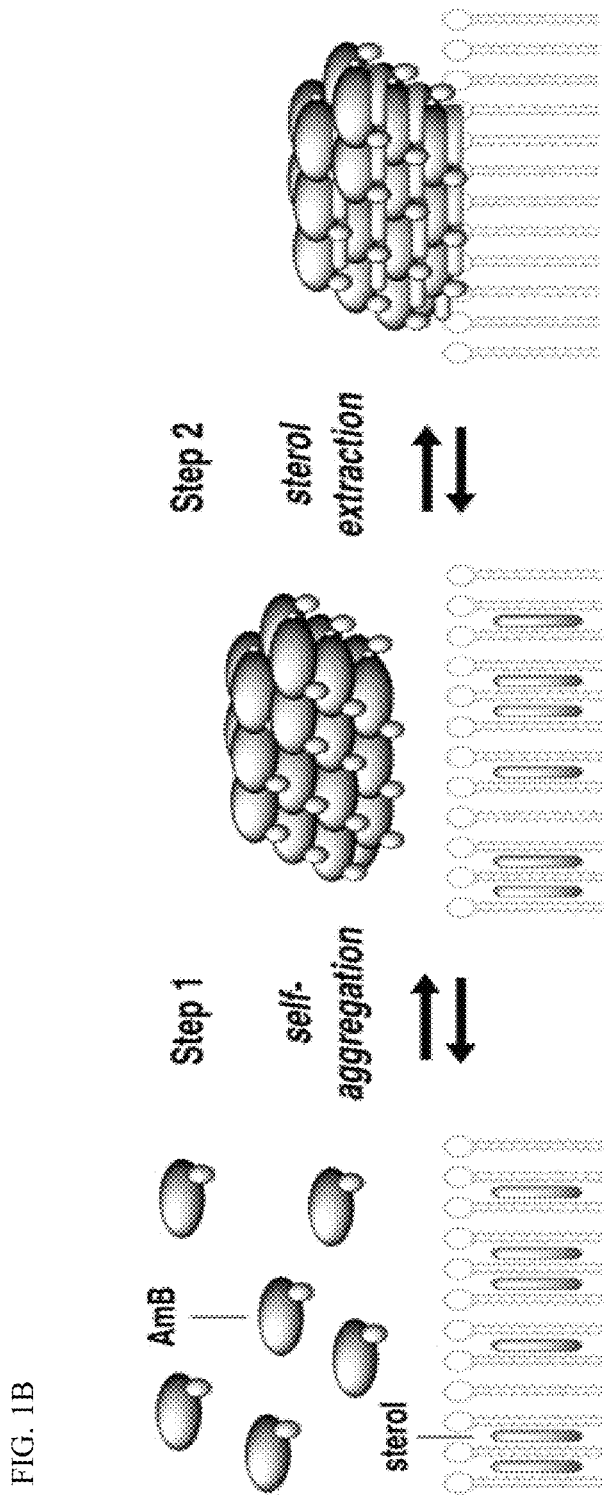
FIG. 1B depicts a two-step "Sterol Sponge" model for the cytocidal action of AmB.

Enabled by the disclosed development of frontier synthesis methods for efficient modification of new AmB derivatives, we alternatively discovered that AmB primarily kills fungal and human cells by binding ergosterol and cholesterol, respectively (FIG. 1A); channel formation is not required. All data are consistent with a "sterol sponge" model (FIG. 1B), whereby AmB self-assembles into a large extramembraneous aggregate and rapidly extracts physiologically vital sterols from fungal and human cells, thereby causing cell death. Frontier SSNMR studies (w/Chad Rienstra at UIUC) further revealed key insights into the structure of AmB sponge-sterol complexes. Anderson, T. M. et al., *Nat Chem Biol* 2014, 10 (5), 400-6.

Figure 2B:
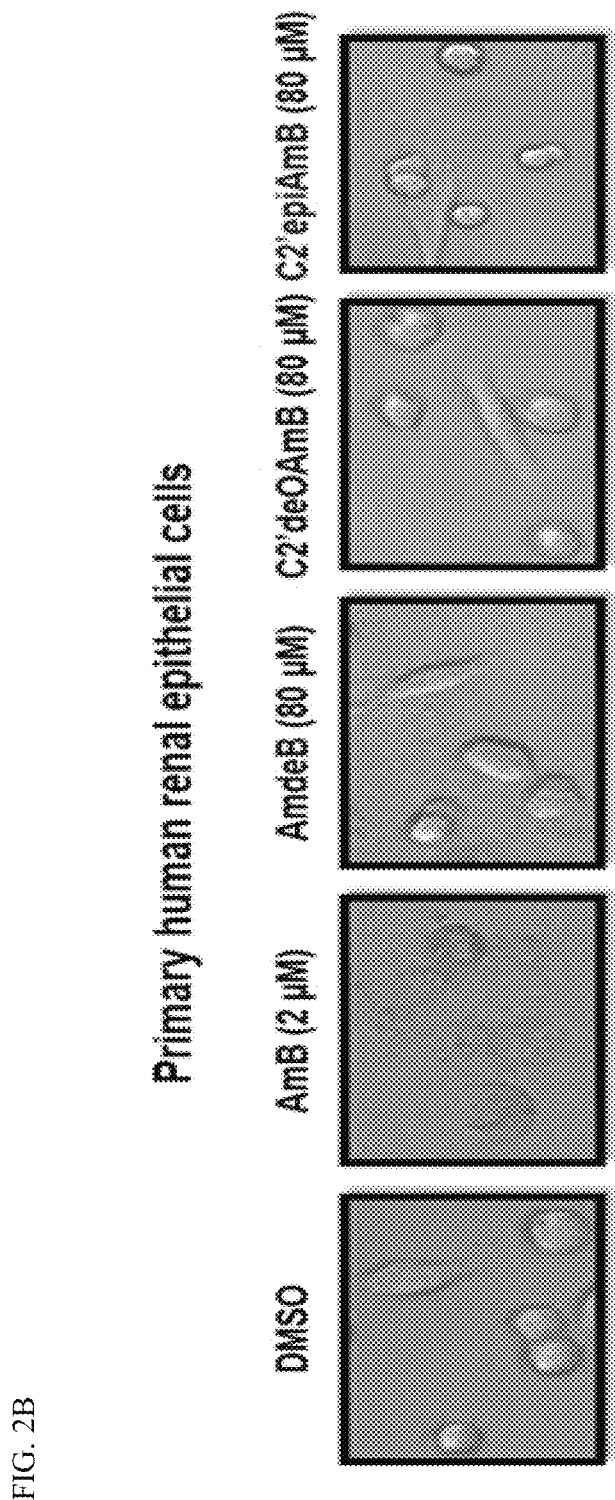
FIG. 2B represents biophysical activities of AmB, AmdeB, C2'deOAmB, and C2'epiAmB in primary human renal epithelial cells.
Figure 2C:
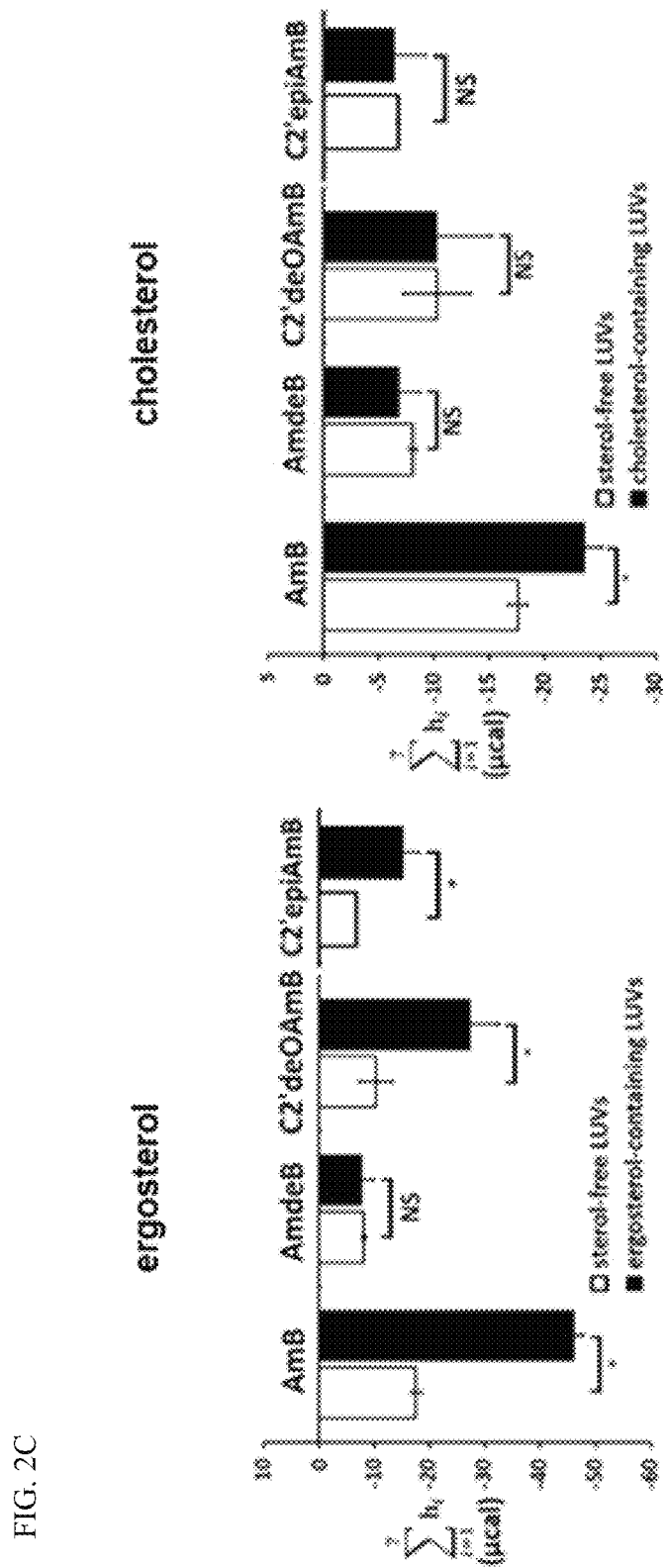
FIG. 2C represents ergosterol and cholesterol activities of AmB, AmdeB, C2'deOAmB, and C2'epiAmB.

This key discovery opened a path to the rational development of a non-toxic AmB variant. To probe its predicted role in sterol binding, the hydroxyl group was synthetically deleted at the C2' position on the mycosamine appendage. The resulting derivative, C2'deOAmB (FIG. 2A), was found to bind ergosterol but, within the detection limits of isothermal titration calorimetry (ITC), not cholesterol (FIG. 2C). Consistent with the sterol sponge model, this derivative retained good activity against yeast but, most importantly, was nontoxic to human red blood cells and primary (hREC) (FIG. 2B).

Figure 3A:
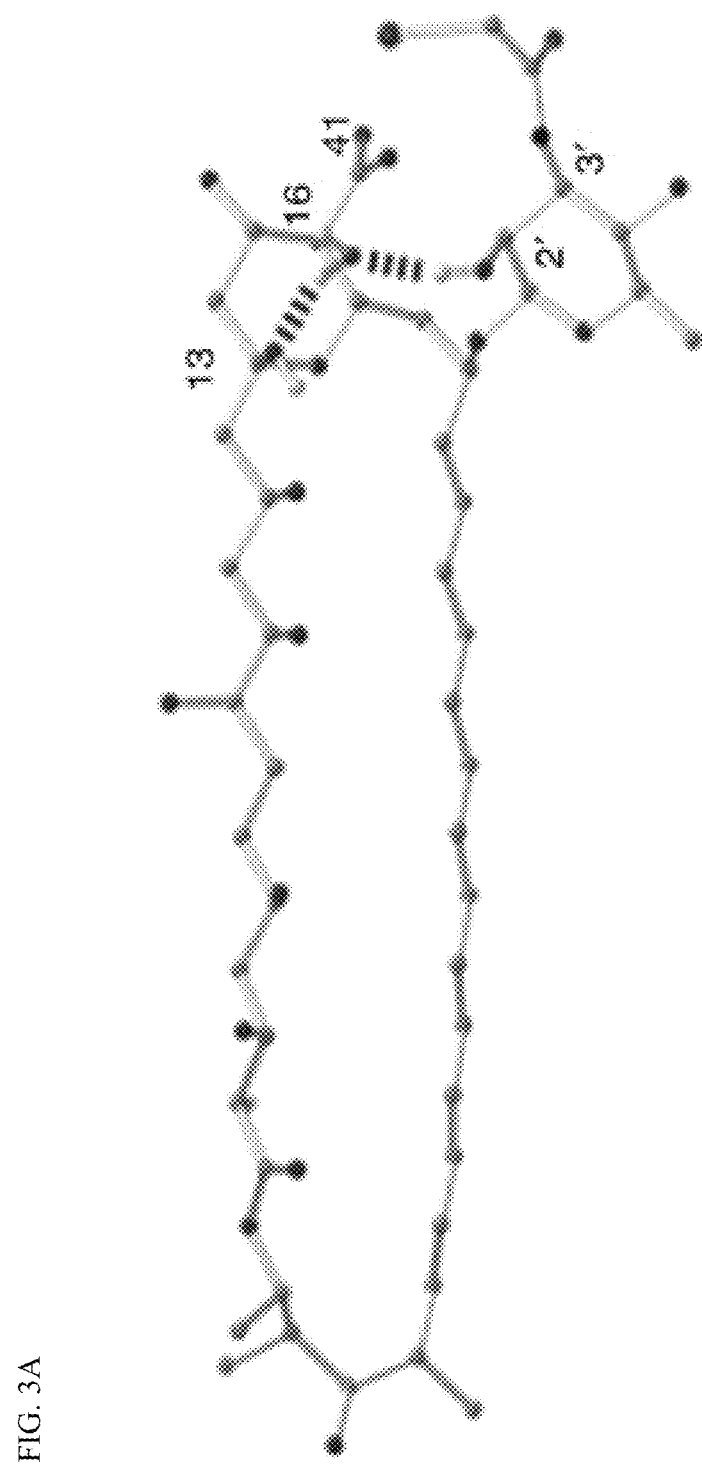
FIG. 3A is an X-ray crystal structure of N-iodoacyl AmB.
Figure 3B:
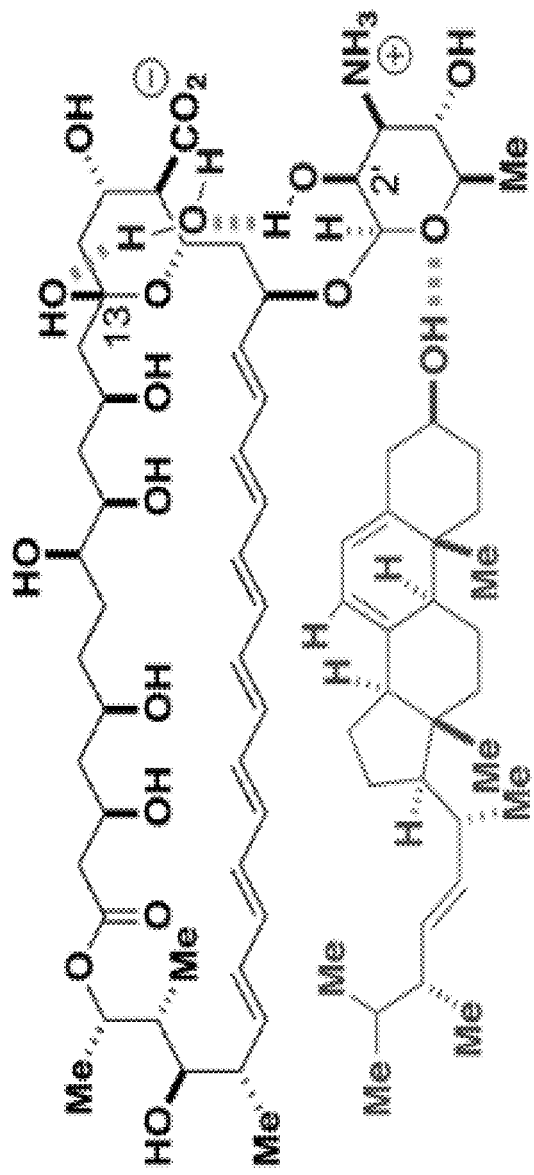
FIG. 3B depicts a proposed structural model for AmB-Erg complex. A similar model is proposed for cholesterol.

2-Deoxy glycosides are notoriously challenging to synthesize and lack of scalable access to C2'deOAmB has precluded its development. However, these findings led us to a predictive model for guiding the development of more synthetically accessible derivatives with similar selectivity profiles. Crich, D. et. al., *The Journal of Organic Chemistry* 2011, 76 (22), 9193-9209; Hou, D. et al., *Carbohyd Res* 2009, 344 (15), 1911-1940; Rodriguez, M. Á. Et al., *The Journal of Organic Chemistry* 2005, 70 (25), 10297-10310; and Hou, D., et al., *Organic Letters* 2007, 9 (22), 4487-4490. Specifically, to rationalize the selective toxicity of C2'deOAmB for fungal vs. human cells, a model was proposed in which the C2'-OH stabilizes a conformer of AmB that readily binds both ergosterol and cholesterol. The deletion of this hydroxyl group favors a shift to a different conformer or set of conformers which retain the capacity to bind ergosterol but not the more sterically bulky cholesterol. Alternatively, this model suggests that deletion of the C2'OH of AmB causes a small molecule-based allosteric effect that results in ligand-selective binding. Based on the high-resolution X-ray crystal structure of N-iodoacyl AmB (FIG. 3A), there is a prominent water-bridged hydrogen-bond between the hydroxyl groups at C2' and C13 that may serve to stabilize a particular conformation of the mycosamine appendage relative to the polyene macrolide core. This observation, combined with our previous findings that the mycosamine appendage is critical for binding both ergosterol and cholesterol and observations by SSNMR of direct intermolecular contacts between the AmB polyene and the A/B rings of ergosterol, allowed us to propose a specific structural model for both AmB-sterol complexes consistent with all of our data (FIG. 3B). Woerly, E. M. et al, *Nat Chem* 2014, 6 (6), 484-91; Anderson, T. M. et al., *Nat Chem Biol* 2014, 10 (5), 400-6.

Guided by this model, a simple epimerization of the more synthetically accessible C2' hydroxyl group, would likewise eliminate the water-bridged C2'OH—C13OH interaction and cause a shift in the orientation of the mycosamine appendage similar to that predicted in C2'deOAmB. The resulting derivative, C2'epiAmB (FIG. 2A), selectively binds ergosterol and exerts cytocidal action against fungal but not human cells. Notably, C2'epiAmB differs from AmB only in the stereochemistry at a single atom.

Figure 4:
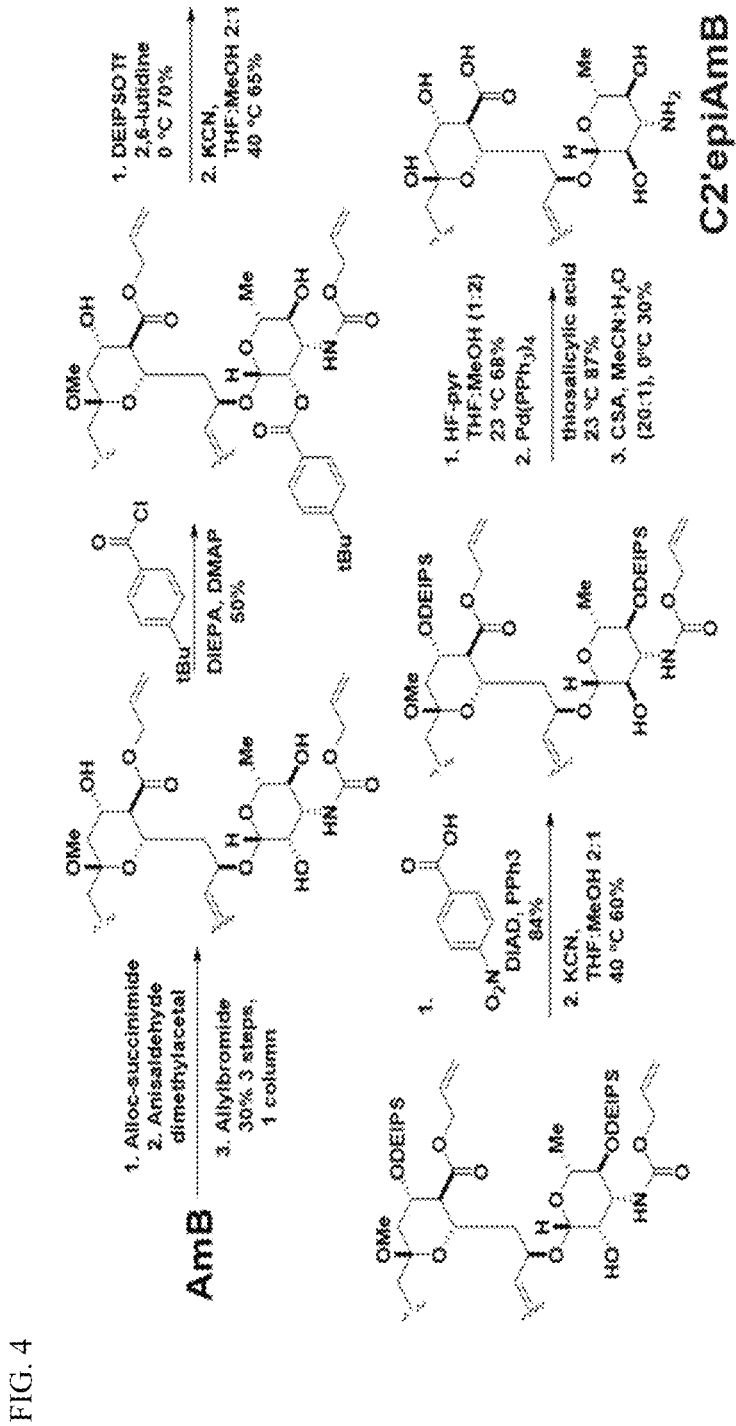
FIG. 4 represents the 11-step synthesis of C2'epiAmB from AmB.

A practical 11-step synthesis of C2'epiAmB using a frontier site-selective acylation method was developed (FIG. 4). Wilcock, B. C. et al., *Nat Chem* 2012, 4 (12), 996-1003; Uno, B. E. *A synthesis enabled understanding of Amphotericin B leading to derivatives with improved therapeutic indices.* University of Illinois at Urbana-Champaign, 2014. The sterol binding and cell killing activities was then determined. As predicted, like C2'deOAmB, C2'epiAmB was found by ITC to bind ergosterol but not (detectably) cholesterol, and, most importantly, to kill fungal but not human cells (FIGS. 2A-C).

Figure 5A:
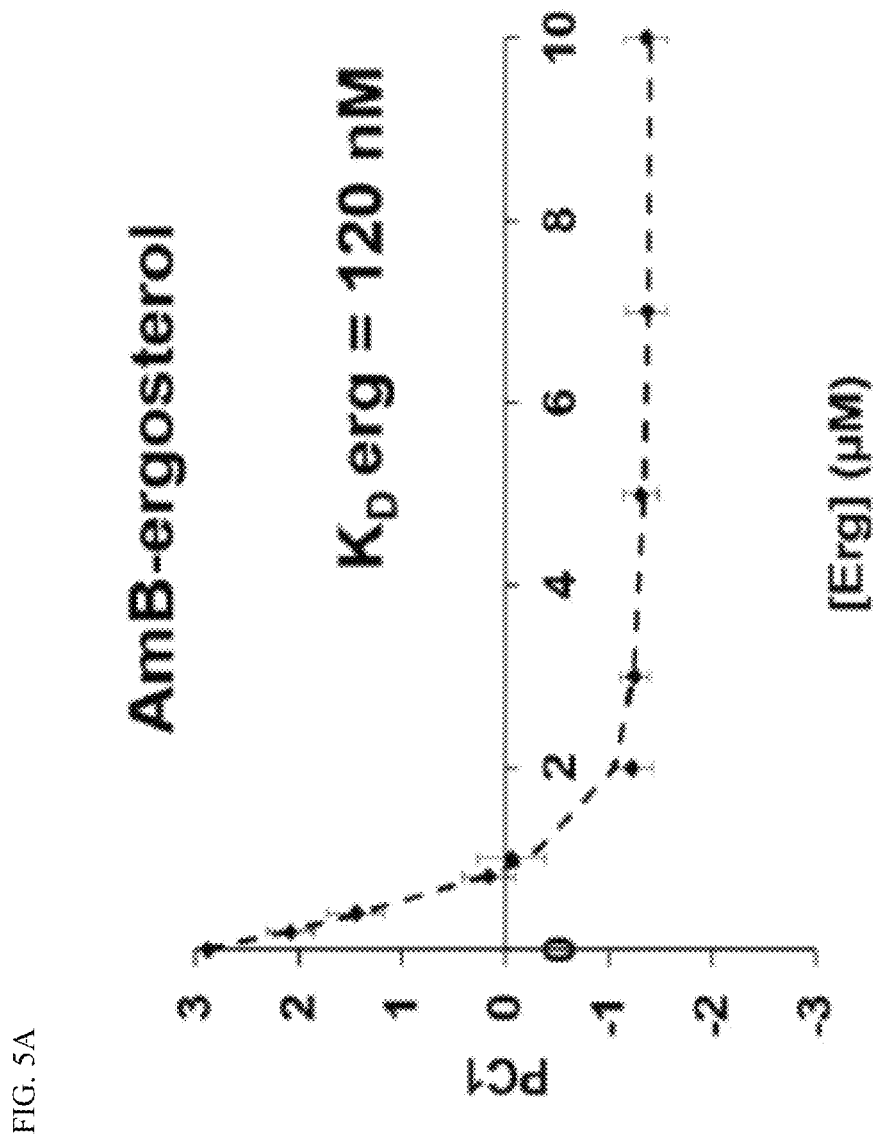
FIG. 5A depicts sterol binding. Sterol sponges formed in vitro from AmB were titrated with ergosterol and analyzed by UV-Vis spectroscopy.
Figure 5B:
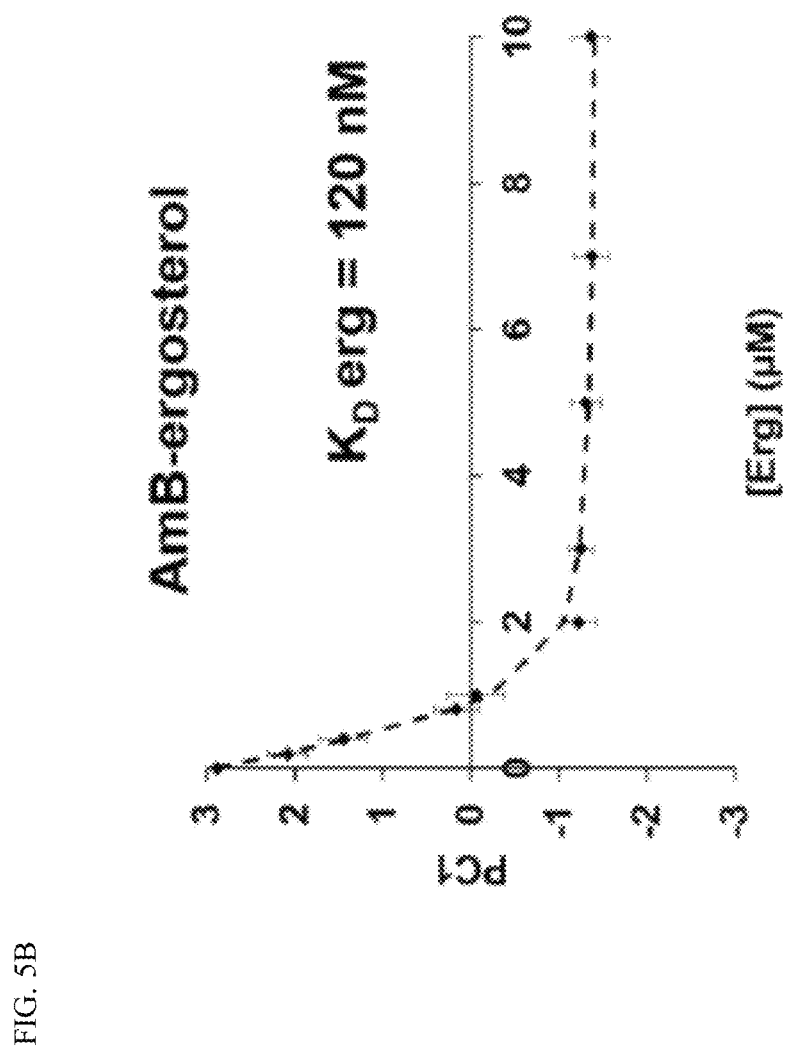
FIG. 5B depicts sterol binding. Sterol sponges formed in vitro from AmB were titrated with cholesterol and analyzed by UV-Vis spectroscopy.
Figure 5C:
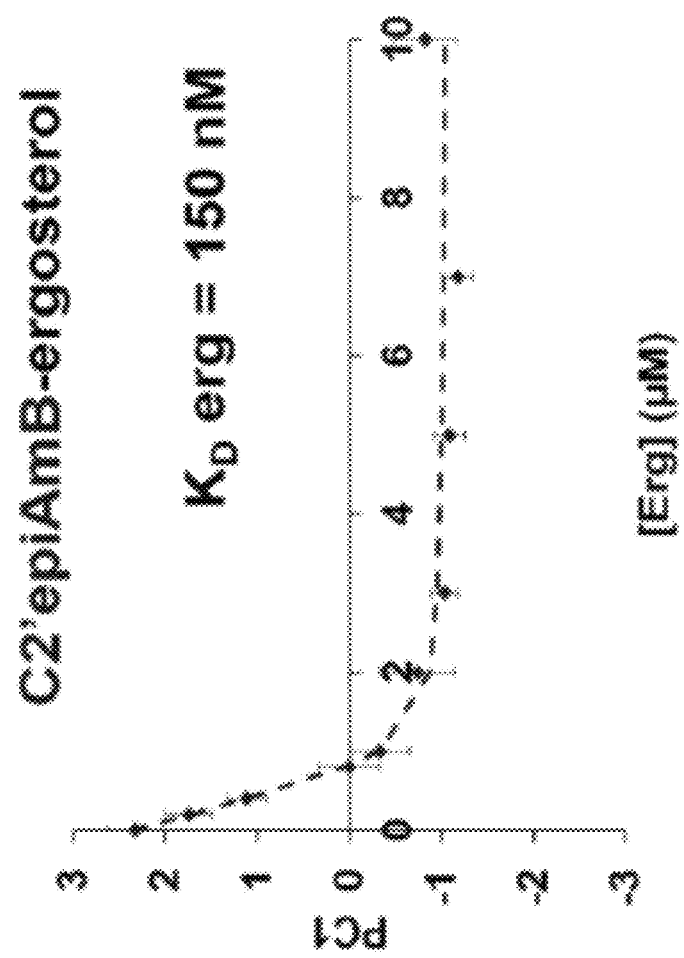
FIG. 5C depicts sterol binding. Sterol sponges formed in vitro from C2'epiAmB were titrated with ergosterol and analyzed by UV-Vis spectroscopy.
Figure 5D:
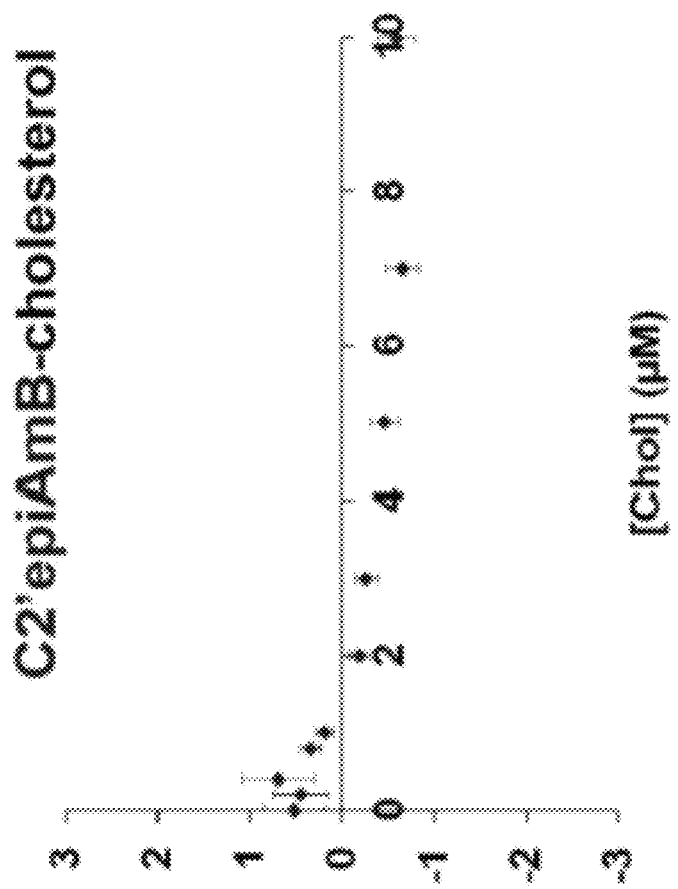
FIG. 5D depicts sterol binding. Sterol sponges formed in vitro from C2'epiAmB were titrated with cholesterol and analyzed by UV-Vis spectroscopy.

These ITC studies failed to yield S-shaped isotherms, precluding determination of binding constants and other thermodynamic parameters. However, an alternative method was developed for reproducible formation of homogenous AmB and C2'epiAmB sterol sponge aggregates in vitro. Using these preparations, a quantitative UV-Vis and Principle Component (PCA) based assay for determining the apparent $K_{DS}$ for the binding of AmB and C2'epiAmB to ergosterol and cholesterol (FIGS. 5A-D) was developed. Consistent with the small therapeutic index of this natural product, strong binding of AmB to both ergosterol ($K_{D, erg}$=120 nM) and cholesterol ($K_{D,chol}$=840 nM) was observed. Consistent with evaluating C2'epiAmB in vitro, strong binding for C2'epiAmB to ergosterol ($K_{D,erg}$=150 nM) (FIG. 5C), but little or no binding of cholesterol (FIG. 5D) was observed. The data does not permit confident assigning of a $K_D$ for the latter interaction, but it was estimated that it is at least >2000 nM (which is the estimated $K_{D,chol}$ if the data was fitted). Since C2'epiAmB shows no mammalian toxicity, these mechanistically grounded biophysical parameters can be used as benchmarks to prioritize new hybrid derivatives for further development.

Example 2

AmB Derivatives With No Observed Animal Toxicity

Figure 6:
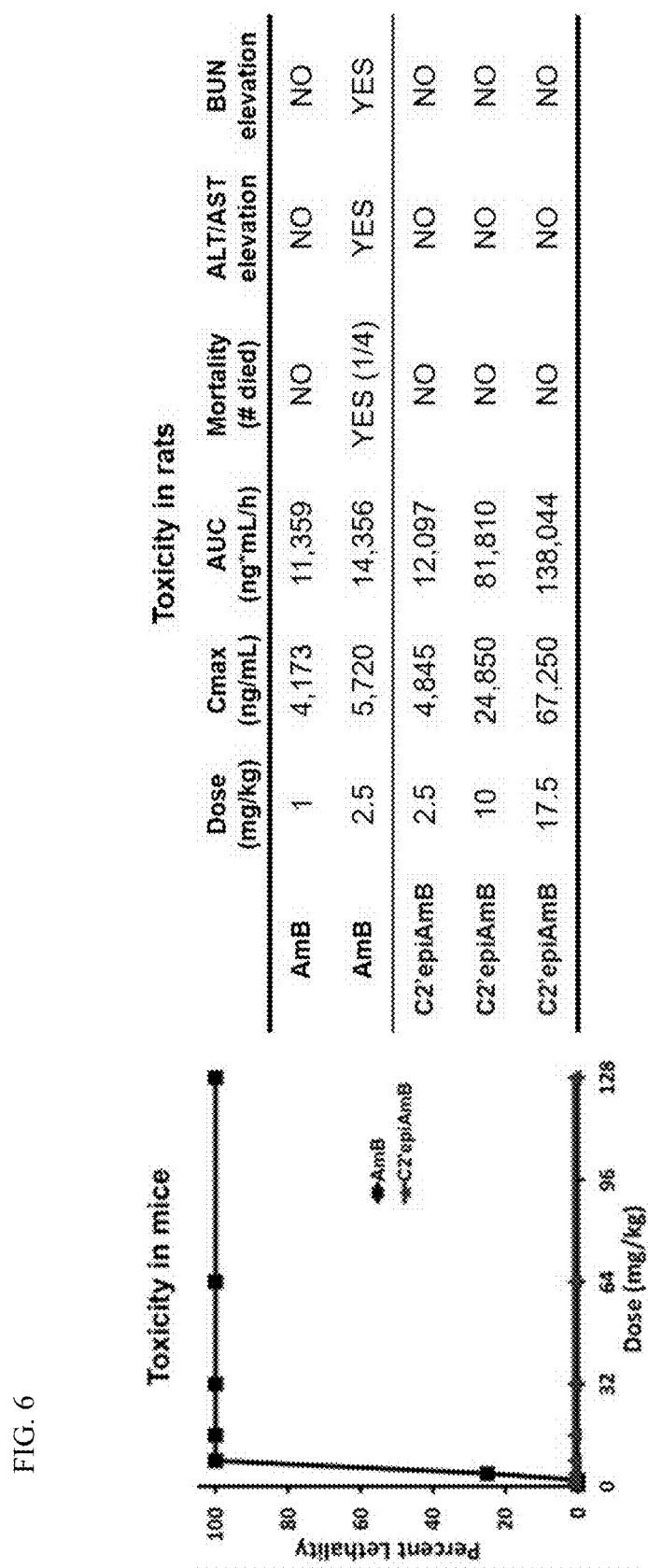
FIG. 6 represents toxicity data of AmB-deoxycholate and C2'epiAmB-doxycholate in mice.

>100 mg of C2'epiAmB was prepared, formulated it as the corresponding deoxycholate complex, and evaluated this derivative head-to-head with AmB-deoxycholate for toxicity and efficacy in animal models. Intravenous (IV) administration of AmB-deoxycholate to mice was found to be lethal at 2-4 mg/kg (FIG. 6, Left). In contrast, no mortality was observed upon IV injection of C2'epiAmB-deoxycholate even at 128 mg/kg (the highest dose tested). IV administration of AmB-deoxycholate to rats (2.5 mg/kg) caused significant elevations in Blood Urea Nitrogen (BUN), Alanine transaminase/Aspartate transaminase (ALT/AST) and mortality (FIG. 6, Right). Alternatively, no elevations in BUN or ALT/AST and no mortality when rats were treated with IV injections of C2'epiAmB at doses of 2, 10, and 17.5 mg/kg (the highest dose that was tested) was observed. The $C_{max}$ for C2'epiAmB at 17.5 mg/kg was >16-fold higher than the $C_{max}$ for AmB at 1 mg/kg.

The toxicity of C2'epiAmB to AmBisome®, a liposomal formulation of AmB that is widely used clinically because it is somewhat less toxic than Fungizone® (AmB-deoxycholate) (FIG. 7) was directly compared. Consistent with literature precedent, we confirmed that AmBisome® shows significant toxicity in mice at 48 mg/kg as judged by state-of-the art renal genotoxicity biomarkers. Kondo, C. et al., *J Toxicol Sci* 2012, 37 (4), 723-37. Alternatively, mice were injected with the same high dose (48 mg/kg) of C2'epiAmB-deoxycholate and observed no significant elevations in these same biomarkers. Thus, C2'epiAmB is significantly less toxic than AmBisome® in mice.

In each case, C2'epiAmB is non-toxic to human red blood cells, primary hREC, mice, and rats up to the highest dose tested. These results are consistent with the finding that, within limits of detection of all of the experiments, C2'epiAmB does not bind cholesterol.

Example 3

Partially Retained In Vitro Antifungal Activity

In vitro antifungal activity of C2'epiAmB was compared with that of AmB against an extensive series of *Candida* and *Aspergillus* clinical isolates (FIG. 8A) at Evotec (Oxfordshire, UK). C2'epiAmB showed good activity against many *Candida* and several *Aspergillus* strains. However, there were several strains of *A. fumigatus* (AF293, A1163, and ATC204305), for which C2'epiAmB was 4-fold less potent than AmB, and in one strain (AF91) C2'epiAmB was >32 times less potent. C2'epiAmB was also sent to the US national Fungus Testing Laboratory at UT-San Antonio for antifungal testing against an extended panel of especially challenging 40 *Aspergillus* clinical isolates, including azole-resistant *A. fumigatus, A. flavus*, and *A. terreus* (FIG. 8B). C2'epiAmB was found to be 2-16 times less potent than AmB (average 5.6-fold less potent across all 40 strains). Recently, Steinbach and Burke directly compared the activity of AmB, AmBisome®, caspofungin, voriconazole, and C2'epiAmB against an even broader panel of clinically relevant invasive molds (FIG. 8C). These studies again showed good antifungal potency for C2'epiAmB against many strains, including a pan-azole resistant strain (F14196), but also important opportunities for improved activity against *Aspergillus*.

Example 4

Retained Primary Mechanism of In Vitro Antifungal Activity

Figure 9:
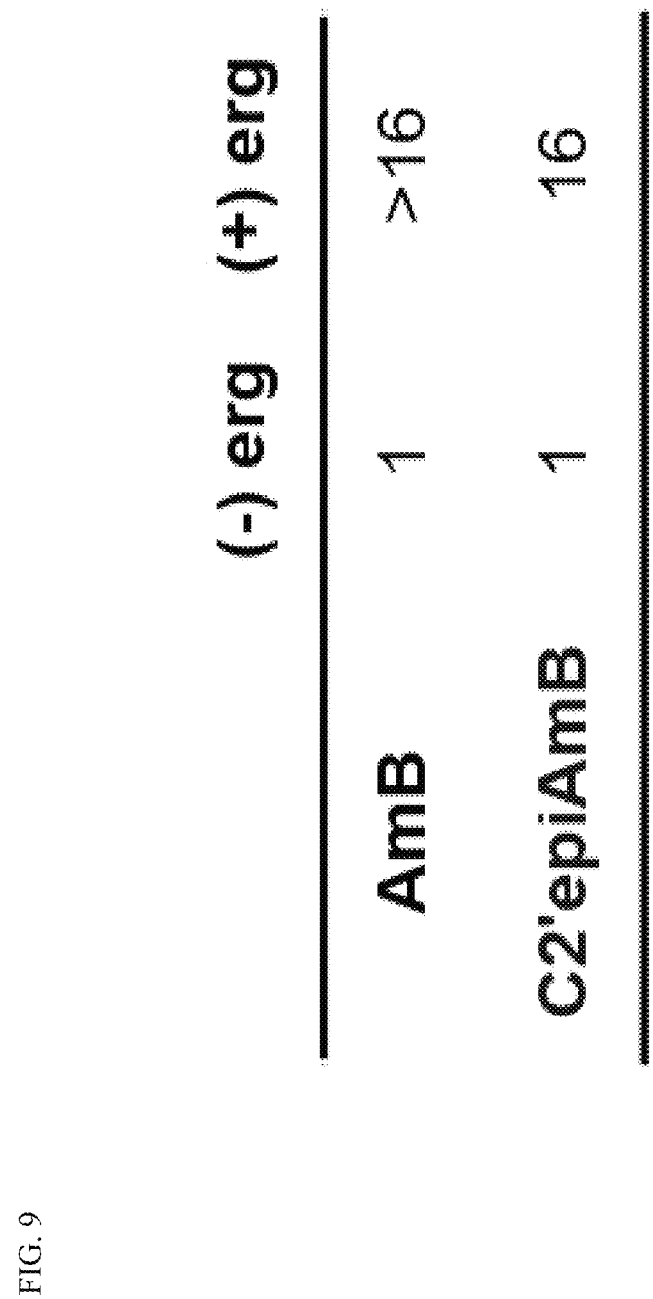
FIG. 9 depicts the MICs of AmB and C2'epiAmB against C. albicans with and without pre-complexation with ergosterol.

Providing strong evidence for the sterol sponge mechanism, it was previously demonstrated that the antifungal activity of AmB is mitigated via pre-complexing the AmB sterol sponge with ergosterol, thus blocking its ability to extract ergosterol from yeast cells. Anderson, T. M. et al., *Nat Chem Biol* 2014, 10 (5), 400-6. In a follow-up study performed in collaboration with Susan Lindquist at MIT, this mechanism also showed that it is inherently evasive to clinical resistance, because mutating the ergosterol target causes loss of pathogenicity. Davis, S. A., et al., *Nat Chem Biol* 2015, 11 (7), 481-7. To test whether C2'epiAmB primarily kills cells via the same sterol sponge mechanism, the C2'epiAmB sponge was similarly pre-complexed with ergosterol (FIG. 9). The same reduction in potency for AmB and C2'epiAmB upon ergosterol pre-complexation was observed. Thus, C2'epiAmB similarly kills yeast primarily via sterol binding, and, by extension, the new compounds targeted in this application are expected to have a similar barrier to fungal resistance that has been observed for the past 50+ years with AmB.

Example 5

Non-Toxic Dose-Dependent Efficacy in Murine Invasive *Candidiasis*

Figure 10:
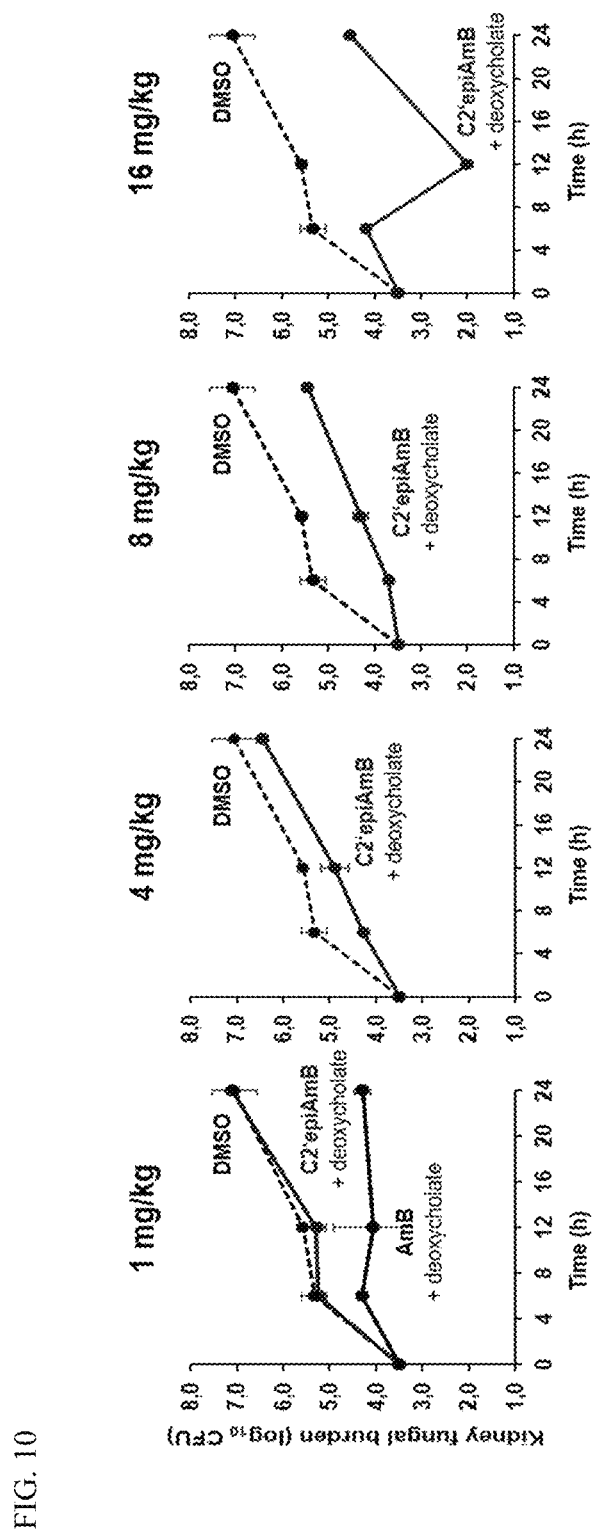
FIG. 10 represents the efficacy of AmB and C2'epiAmB in a mouse model of invasive candidiasis.

Finally, the dose-dependent efficacy of C2'epiAmB-deoxycholate complex in a murine model of invasive *candidiasis* was tested (FIG. 10). Neutropenic ICR/Swiss mice were injected via lateral tail vein with a lethal inoculum of *C. albicans* and then treated via single IP injection of AmB-deoxycholate (1 or 4 mg/kg) or C2'epiAmB-deoxycholate (1, 4, 8, or 16 mg/kg). Previous work from the Andes lab shows dose-dependent efficacy for AmB-deoxycholate. Andes, D. et al., *Antimicrobial agents and chemotherapy* 2001, 45 (3), 922-6. In fact, the PD parameter that best correlates with outcome is Cmax-/MIC. The same was subsequently observed in a pulmonary model of invasive aspergillosis. Wiederhold, N. P. et al., *Antimicrobial agents and chemotherapy* 2006, 50 (2), 469-73. As shown in FIG. 10 C2'epiAmB also showed dose-dependent efficacy, with outstanding reductions in fungal burden at the 16 mg/kg dose.

These results show that C2'epiAmB is a unique antifungal agent with potent fungicidal activity against several *Candida* and *Aspergillus* strains and no detectable mammalian toxicity, a first for an amphotericin derivative. However, C2'epiAmB also has some important limitations with respect to potency and pathogen scope. Thus, the next plan is to develop a new series of "hybrid" derivatives designed to improve the antifungal potency and pathogen scope of C2'epiAmB while maintaining its lack of toxicity.

Example 6

Chemical Modifications Resulting in Excellent Efficacy, But Retained Toxicity Limitations AmB urea derivatives modified at C16 have shown to substantially increase antifungal activity in vitro and in vivo relative to AmB. These compounds are orders of magnitude more water soluble than AmB, which may in part account for their improved potency. These urea derivatives evaded pathogen resistance and also displayed excellent PK/PD properties in mice, rats, and dogs. However, these derivatives had unacceptable toxicities. Thus, the toxicity-eliminating modification found in C2'epiAmB was combined with the efficacy-promoting modifications at C16 to develop a new class of hybrid polyene fungicidal agents that are both non-toxic and exceptionally effective in eradicating invasive fungal infections.

Figure 11A:
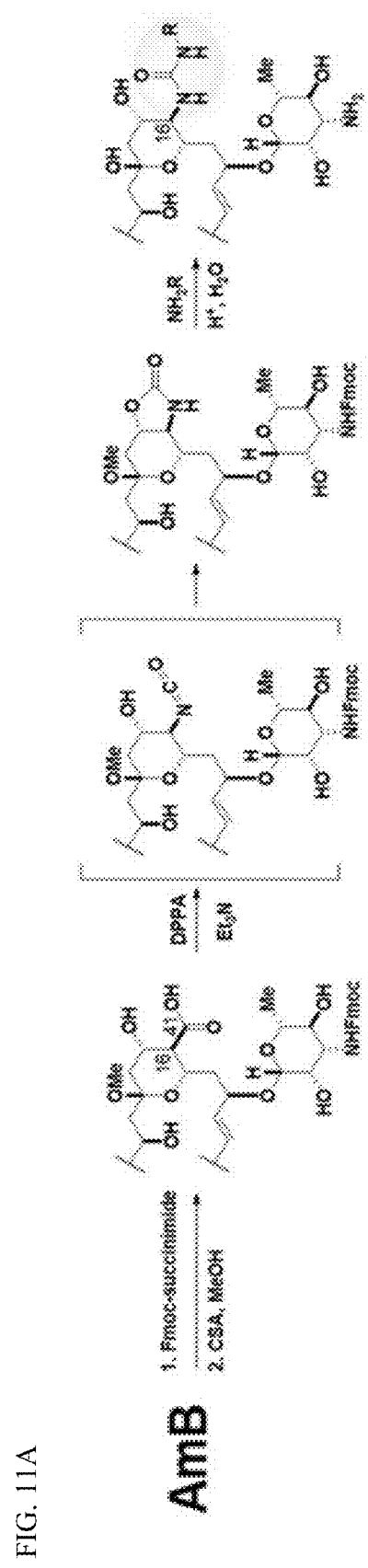
FIG. 11A represents a practical three-step synthesis of AmBUreas from AmB.

Burke, Andes, and Lindquist reported in 2015 a series of AmB derivatives in which the C16 acid is replaced with a urea motif via a scalable 3-step synthesis from AmB (FIG. 11A). Davis, S. A., et al., *Nat Chem Biol* 2015, 11 (7), 481-7. AmBUreas were studied at REVOLUTION Medicines, a biotech company for which Burke is a Founder and Consultant and Steinbach served on the Clinical Advisory Board. Several derivatives demonstrated in vitro potency and scope similar to AmB against a panel of clinical isolates (FIG. 11B).

Steinbach and Burke recently collaborated to further compare the activity of a series of AmBUreas (AmBAU, AmBMU, and AmBCU) with AmBisome®, C2'epiAmB, caspofungin, and voriconazole against a wide range of clinically relevant pathogens, including AmB-resistant *Scedosporium* strains (FIG. 11C). Again, AmBAU showed excellent potency, equal if not better than that shown by AmB across a wide range of pathogens, importantly it was active against the recalcitrant strain *Scedosporium prolificans*.

Recently another AmB urea possessing a primary amine, AmBTACBU (FIG. 11B) was identified which was found to be more potent than AmB in vitro (FIG. 11B) (Mean MIC for AmB=1.23 µM, Mean MIC for AmBTACBU=0.95). Both AmBAU and AmBTACBU was further tested and compared to AmB against four strains of clinically relevant *Candida* species and four challenging strains of *A. fumigatus* (FIG. 11D). Substantial increases in potency (Mean MIC for AmB=1.33 µM; Mean MIC for AmBAU=0.5; Mean MIC for AmBTACBU=0.4) was observed. Importantly, it was also found that these AmBUreas are more water soluble than AmB, which may in part account for their increased potencies.

Figure 12:
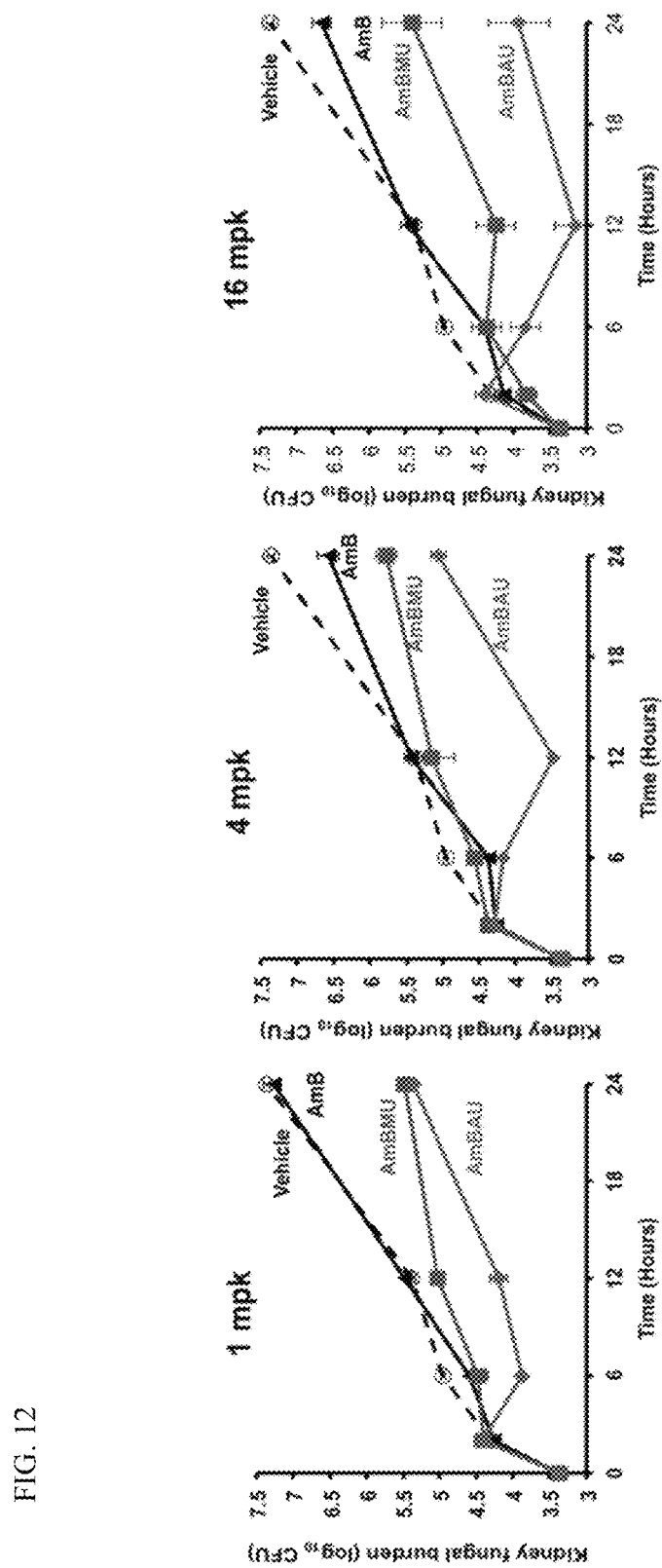
FIG. 12 represents the efficacy of AmB, AmBMU and AmBAU in a mouse model of invasive candidiasis.
Figure 13:
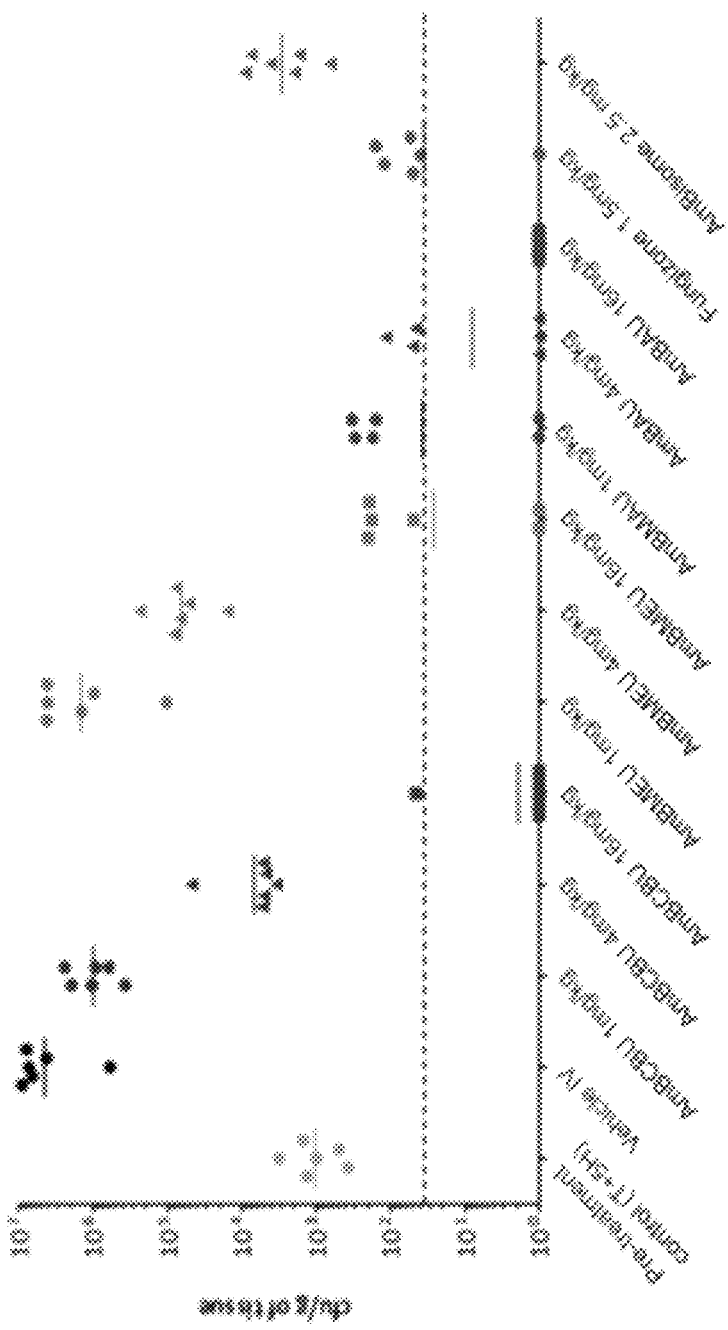
FIG. 13 represents the efficacy of AmBCBU, AmBMEU, AmBAU, Fungizone®, and AmBisome® in a candidiasis mouse model.

AmBAU proved to be exceptionally effective when administered intraperitoneally in a murine model of invasive candidiasis (FIG. 12). To enable a head-to-head comparison with the AmB urea derivatives, AmB was delivered as a non-deoxycholate complex. The lack of solubility likely accounts for the atypical lack of dose-response observed for AmB in these experiments. These AmBUreas were also tested via intravenous administration in a similar model at EvoTec (Oxfordshire, UK), and their activities were compared directly with IV AmB-deoxycholate (Fungizone®) and liposomal AmB (AmBisome®) (FIG. 13). Good activity was observed for AmBCBU and AmBMEU, with substantial reductions in kidney fungal burden at 4 and 16 mg/kg for each compound. Again, AmBAU was exceptionally effective, leading to sterilization in multiple mice (within the limits of assay detection) with just 1 mg/kg IV AmBAU. This was equal to the activity of IV Fungizone® delivered at its MTD (1.5 mg/kg), and superior to IV AmBisome® (2.5 mg/kg). Most importantly, complete sterilization was achieved with AmBAU at 16 mg/kg. AmBAU demonstrated favorable PK/PD properties in mice, rats, dogs (FIG. 14), and had a similar capacity to evade pathogen resistance as AmB.

Figure 7:
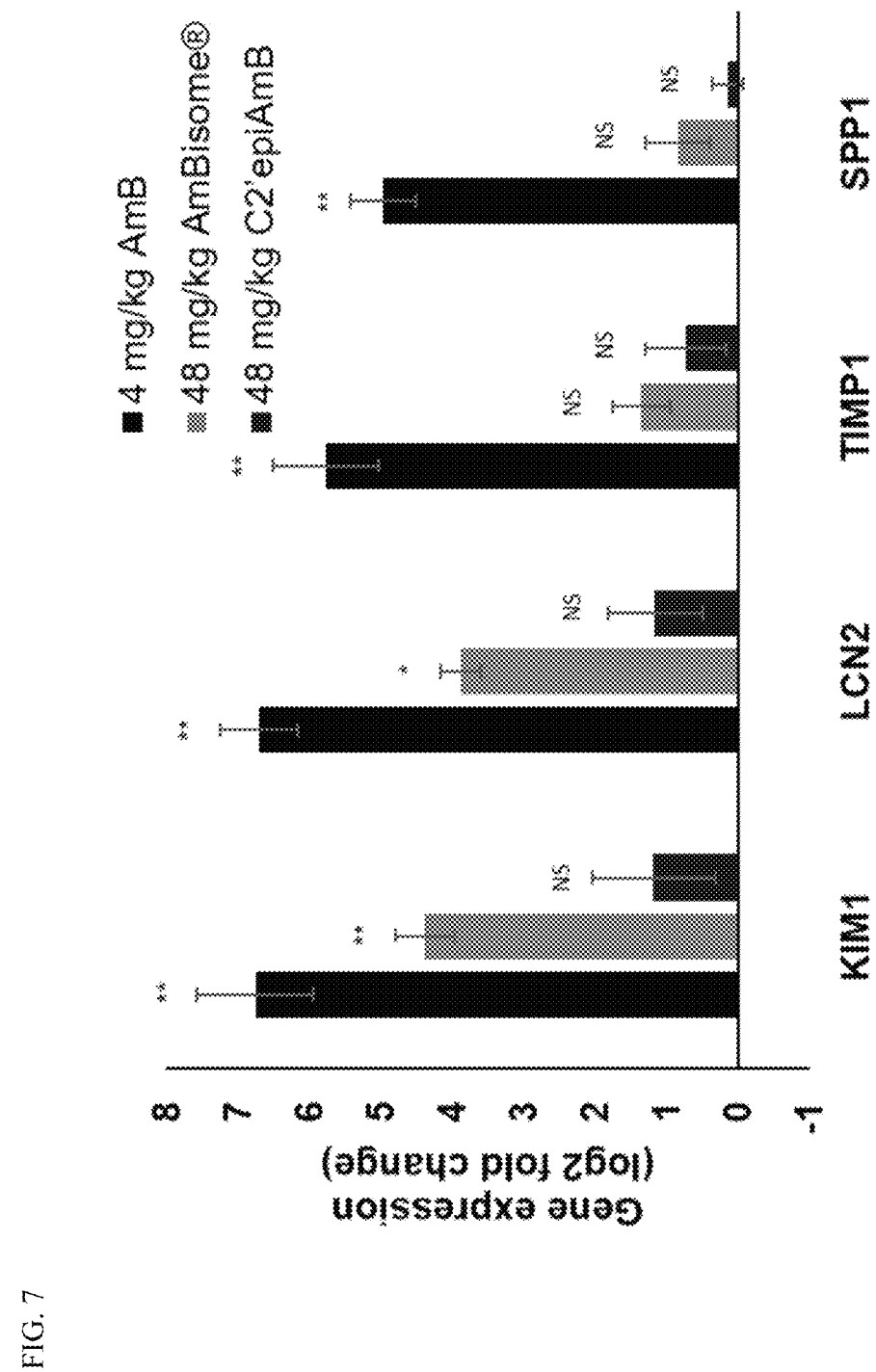
FIG. 7 represents toxicity data of AmBisome® compared directly with C2'epiAmB, as judged by renal genotoxicity biomarkers.

AmBUreas were also less toxic than AmB in vitro and in vivo, but were less than the complete elimination of toxicity observed with C2'epiAmB (FIGS. 6 and 7). Specifically, the minimum toxic concentrations (MTC) against primary hRECs are 2.4 µM for AmB, 11.3 µM for AmBAU, 44.4 µM for AmBMU, and >80 µM for C2'epiAmB. In IV-injected mice, death was observed at 32 mg/kg for AmBAU, whereas all mice treated with C2'epiAmB at 128 mg/kg survived. In rats, both AmBMU and AmBAU caused significant toxicity at 6 mg/kg, precluding further development. As described above, no such toxicity was observed in the same rats at the highest tested dose of C2'epiAmB (17.5 mg/kg) (FIG. 6).

Biophysical studies support the conclusion that different capacities to bind cholesterol underlie these striking differences in toxicity for the AmBUreas versus C2'epiAmB (FIG. 15). Isothermal titration calorimetry is unable to distinguish between cholesterol binding in these two series. However, a more sensitive and quantitative UV-Vis/PCA based sponge-sterol titration experiments described above (see Example 1) was employed to quantify the binding of a representative AmB urea (AmBAU) to ergosterol and cholesterol. Like AmB, AmBAU was confirmed to bind ergosterol and cholesterol, consistent with the retained antifungal and mammalian toxicities of this class of compounds. In contrast, C2'epiAmB showed retained binding to ergosterol but no detectable binding to cholesterol and no mammalian toxicity. It was reasoned that the lack of cholesterol binding in C2'epiAmB to a ligand-selective allosteric effect was caused by epimerization of the C2'stereocenter (see Example 1), and thus predict that the biophysical effects associated with C2'-epimerization should be transposable to other AmB derivatives.

Figure 16:
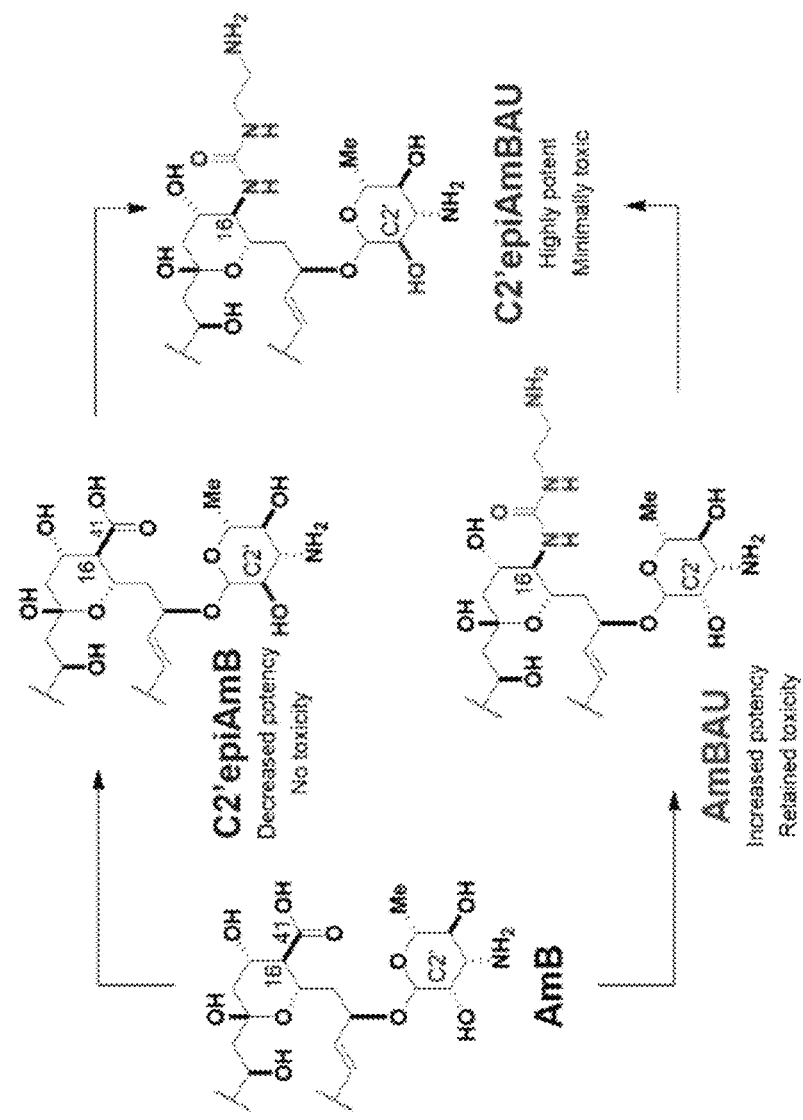
FIG. 16 represents a hybrid AmB derivative, C2'epiAmBAU, with exceptional potency and minimal toxicity.

Thus the goal is to hybridize the toxicity-eliminating modification in C2'epiAmB with the most potency-promoting C16 urea modifications to generate a new class of hybrid AmB derivatives that possess the combined favorable features of both series (FIG. 16). Using this strategy, a new type of fungicidal, broad spectrum, resistance evasive, and non-toxic polyene antifungal that enables a high-dose treatment paradigm for invasive fungal infections will be generated.

Example 7

Synthesis of a New Series of AmB Derivatives That Hybridize the toxicity-Eliminating Epimerization at C2' With Efficacy-Promoting Aminoalkylurea Modifications at C16

Two distinct semisynthetic routes to synthesize C2'epiAmB (FIG. 4) and AmBUreas (FIG. 11A) from AmB were developed. These routes were merged to synthesize a novel series of ~50 hybrid C2'epiAmBUreas, in a single step from a common oxazolidinone intermediate (FIG. 17). 1.5 grams C2'epiAmB was prepared as described in FIG. 4, then converted to the corresponding oxazolidinone intermediate using the process previously developed for AmB; 500 mg of this intermediate will be prepared and purified by reverse-phase MPLC. More than a gram of the analogous intermediate from AmB using the same route and purification protocol was previously prepared. Davis, S. A., et al., *Nat Chem Biol* 2015, 11 (7), 481-7; Wilcock, B. C. et al., *Nat Chem* 2012, 4 (12), 996-1003, which are incorporated herein by reference. This oxazolidinone intermediate will then be subdivided into 20 mg batches, and condensed with a collection of small alkyl diamines (obtained from commercial sources or synthesized using established methods), to yield new targeted hybrid C2'epiAmBUreas (representative examples in FIG. 17). This places the diversification step last in the sequence and employ a scalable, accessible and stable oxazolidinone intermediate, substantially maximizing the overall efficiency of this discovery program.

Figure 17:
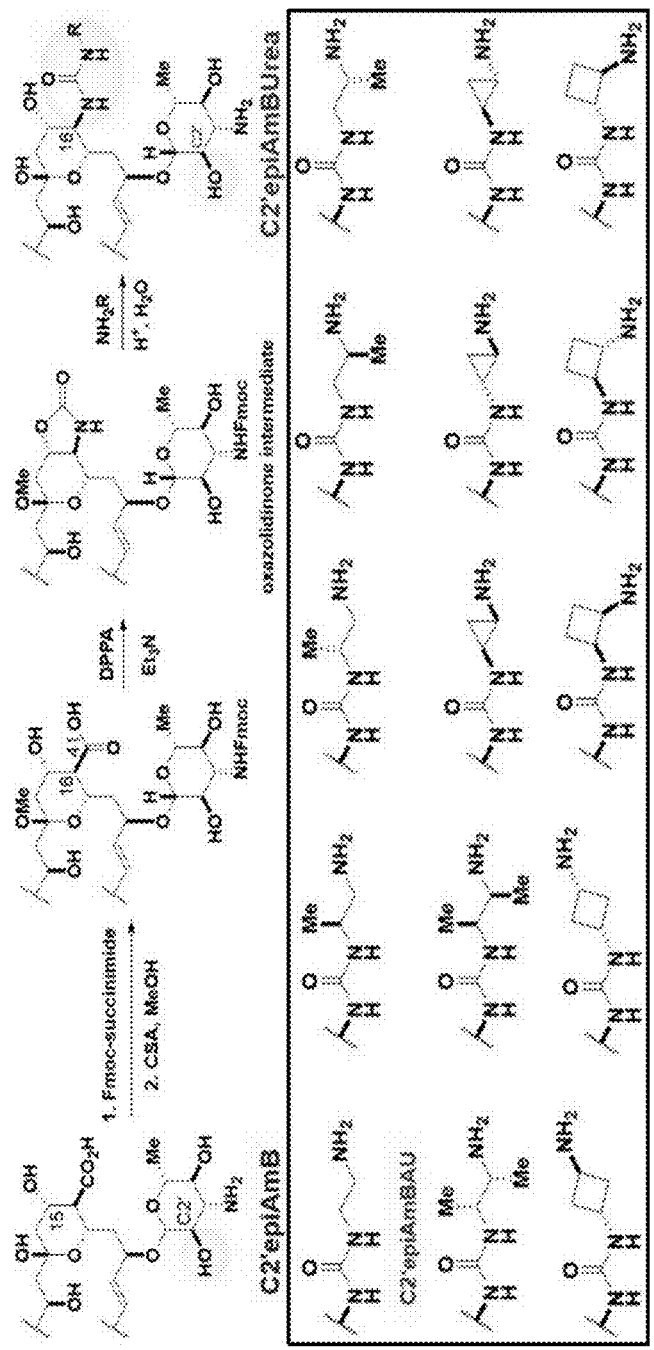
FIG. 17 represents hybrid C2'epiAmBUreas targeted for synthesis.

In a key result, synthesis on small scale was accomplished on the first targeted hybrid derivative, C2'epiAmBAU, as per FIG. 17 confirming the feasibility of the route to these natural product analogs. The initial biological analysis of this first C2'epiAmBUrea derivative was very encouraging since a substantial increase in antifungal potency for C2'epiAmBAU relative to C2'epiAmB was observed (FIG. 18). Specifically, C2'epiAmBAU is up to >500 times more potent than C2'epiAmB, and is even in most cases more potent than AmB, against a series of important pathogens. These include very challenging strains of *Aspergillus* (*A. fumigatus* 91, *A. fumigatus* 1163, and *A. fumigatus* 1100) that showed complete or nearly complete resistance to C2'epiAmB. Moreover, preliminary analysis in hREC demonstrated substantially reduced toxicity for C2'epiAmBAU relative to AmB (minimum toxic concentration (MTC) for AmB=2-4 µM, and preliminary studies yielded an MTC of 64 µM for C2'epiAmBAU).

A diverse collection of aminoalkyl variants will first be synthesized and tested in the first round of the screening funnel described below (Example 8) to quickly establish SAR for this new series. A few derivatives without the amino group will also be prepared, to spot-check whether the amine functionality generally imparts increases in potency. Although no studies related to mammalian toxicity were performed, it is encouraging that a recently described C2'epiAmBC41 methyl ester derivative retained potent antifungal activity. Croatt, M. P. et al., *Organic Letters* 2011, 13 (6), 1390-1393. Once the types of urea substituents that appear most promising are identified, the synthesis of dense collections of structural and stereoisomeric variants of these derivatives for input into the clinically-oriented antifungal screening funnel (Example 8), enabling identification of an optimal derivative for in-depth PK/PD and toxicity studies in larger animals (Example 9).

Each derivative will be purified by reverse-phase HPLC, using the same methods that we previously employed to purify the corresponding AmB ureas. Davis, S. A., et al., *Nat Chem Biol* 2015, 11 (7), 481-7. The structure of each product will be unambiguously confirmed via a standard suite of one- and two-dimensional $^1$H and $^{13}$C NMR techniques (COSY, HMBC, HMQC, NOESY) as well as high resolution mass spectroscopy, as previously done with the AmBUreas. Purity of each product will be judged by analytical HLPC at three different wavelengths (406, 383, 254 nm), with a cut-off of 95% purity in each case. Compounds will be stored as dry powders under inert atmospheres in foil-wrapped vials, and shipped on dry ice to the Steinbach and Andes labs.

Based on extensive experience in synthesizing the AmBUreas and the C2'epiAmBAU, the expectation is that the proposed route will provide access to all of the targeted derivatives, and that condensations between diamines and the oxazolidinone intermediate will yield 5-10 mg of each C2'epiAmB aminoalkylurea. If the yields for any of the targeted condensations are unexpectedly low with the free diamines, the mono-protected variants of the alkyl diamine will be synthesized and the reactions will be repeated using a larger excess of the amine nucleophile in the condensation reaction.

Example 8

Figure 19:
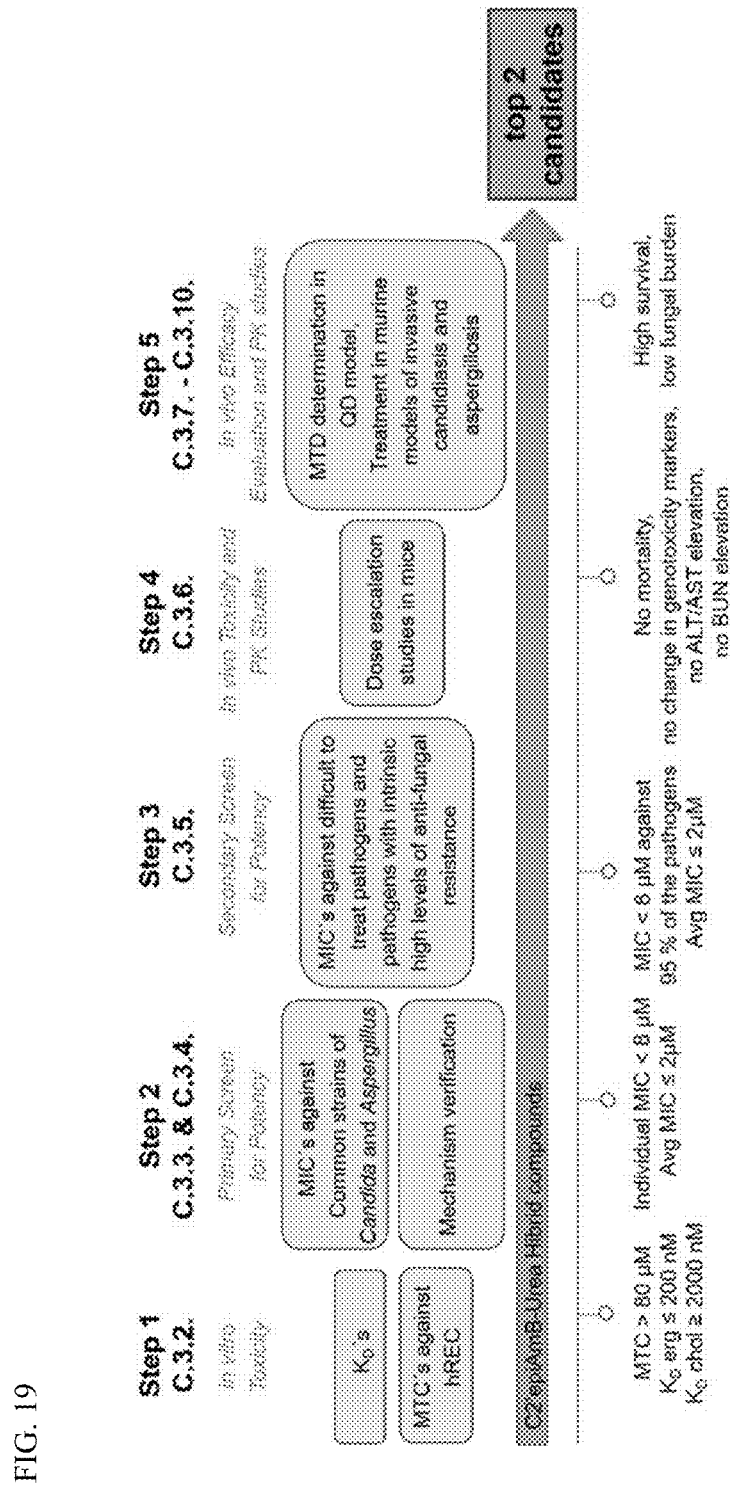
FIG. 19 shows a clinically oriented screening funnel to identify the most promising C2'epiAmBUreas.
Figure 20:
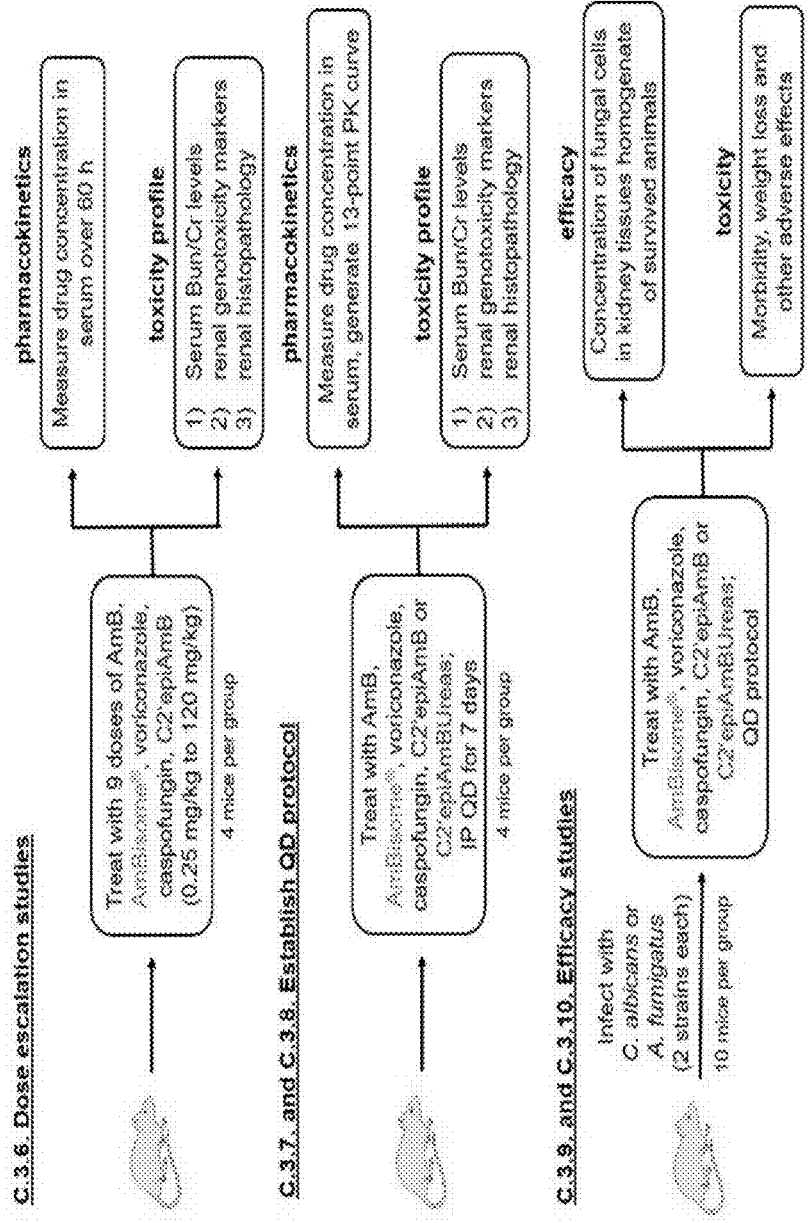
FIG. 20 depicts a systematic efficacy evaluation of high-dose C2'epiAmBUreas.

Characterize the Hybrid C2'epiAmBUreas in a State-of-the-Art Toxicity, Mechanism of Action, and Efficacy Screening Funnel to Identify the Top 2 Candidates For Further Advancement C.3.1. Rationale Employing the rigorous and efficient screening funnel shown in FIG. 19, the five most broadly potent and non-toxic C2' epiAmBUreas will first be identified. Then the derivative which is most effective for following 'high-dose' QD administration in murine models of invasive candidiasis and aspergillosis will be determined. FIG. 20 depicts a systematic efficacy evaluation of high-dose C2'epiAmBUreas.

Scientific Rigor and Biological Variables: To avoid biased interpretations, individuals analyzing data will be blinded to treatment details. Mice will be randomly allocated to experimental groups, and as per NIH's guidelines, a 50:50 ratio of male:female will be included to account for sex as a biological variable. These results will be evaluated via two-way ANOVA, testing for an interaction between the gender and treatment group. If there is a significance between gender and treatment, studies to understand mechanisms underlying gender specific differences will be sought. In vitro studies from three biological replicates from three independent experiments will be analyzed.

C.3.2. $K_D$s For Binding Ergosterol and Cholesterol and In Vitro Toxicity in Primary hREC C2'epiAmB is non-toxic in animals at the highest doses tested. As a first screen to evaluate the toxicity of C2'epiAmBUrea derivatives, two assays will be applied that have mechanistically supported C2'epiAmB's lack of specificity in vitro toxicity against primary hREC and UV-Vis sterol binding. First, the highly sensitive sponge-sterol binding assay demonstrates that C2'epiAmB retains strong binding to ergosterol ($K_{D,erg}$=120 nM) and little or no binding to cholesterol ($K_{D,chol}$>2000 nM). This allows, for the first time, to rationally guide optimization of the therapeutic index based on rigorous quantification of a biochemical parameter directly linked to the primary mechanism driving cellular toxicity. Specifically, the corresponding $K_D$s will be determined for each of the new C2'epiAmBUreas and prioritize advancement of those derivatives that similarly show retained binding to ergosterol ($K_{D,erg}$<200 nM) and little or no binding to cholesterol ($K_{D,chol}$>2000 nM).

These studies have found that a toxicity assay against hRECs, the primary target of toxicity in human patients, has advantages over the commonly used red blood cell lysis assay in evaluating the toxicities of AmB derivatives. In vitro studies with C2'epiAmB also showed that the minimum toxic concentration (MTC) against hREC is >80 µM. Other derivatives (e.g., AmBAU), which proved to be unacceptably toxic in animals, had lower MTCs in this same assay (AmB and AmBAU have MTC's of 2.4 and 11.3 µM, respectively). In contrast, AmBAU failed to fully lyse red blood cells at the highest concentrations tested (>500 µM). Thus, it was concluded that initial toxicity in vitro using hREC is an excellent and superior predictor of in vivo toxicity relative to the more commonly used red cell lysis assay. As a complementary parallel first step in the screening funnel, the MTC's of all new derivatives will be evaluated against hREC using a WST-8 cell proliferation assay kit as previously described above. The MTC will be determined by calculating the mean of at least two biological replicates. Compounds that demonstrate an MTC>80 µM in this assay will also be prioritized for advancement. Thus, combining these metrics, all compounds determined to have $K_{D,erg}$<200 nM, $K_{D,chol}$>2000 nM, and MTC>80 µM in hREC will be advanced for in vitro efficacy testing (see C.3.3.).

C.3.3. In Vitro Antifungal Activity Against Clinically-Relevant Panel of Candida and Aspergillus Strains Promising C2'epiAmB-Urea derivatives will be evaluated for in vitro activity against a panel of the most common pathogenic Candida and Aspergillus species. This study will determine, in triplicate and in parallel with FDA-approved antifungal controls (AmB, AmBisome®, fluconazole, caspofungin, and voriconazole) and C2'epiAmB, the MICs of each compound against the 5 most common species of Candida (C. albicans, C. glabrata, C. krusei, C. tropicalis and C. parapsilosis) and the 5 most common species of Aspergillus (A. fumigatus, A. flavus, A. niger, A. terreus and A. nidulans) following standard CLSI M27-A3 and M38-A2 antifungal susceptibility methodologies.http://shop.clsi.org/site/Sample_pdf/M27A3_sample.pdf. Compounds with an average MIC≤2 µM against both sets of strains, and no individual MIC>8 µM, will be advanced to assess mechanism of action (see C.3.4.).

C.3.4. Verification of Sterol Sponge as Primary Mechanism of Cytocidal Action and Retained Capacity to Evade Resistance This study will determine whether each remaining C2'epiAmBUrea primarily kills yeast via the sterol sponge mechanism. Building on the extensive prior studies with AmB, this study will test each C2'epiAmBUrea test for 1) capacity to extract ergosterol from yeast cells, 2) loss of capacity to extract ergosterol from yeast via pre-complexation with ergosterol, and 3) loss of antifungal potency via pre-complexation with ergosterol. Then it will be determined whether each C2'epiAmBUrea that is confirmed to primarily kill yeast via the sterol sponge mechanism, retains the resistance-evasive properties that are a hallmark of AmB. Building on other extensive studies, this step will 1) test for a retained AmB-like pattern of MICs against an established panel of C. albicans erg mutant strains, and 2) perform gradual resistance-selection protocol in liquid culture, with serial twofold increases in C2'epiAmBUrea concentration to identify any mutants that exhibit a greater than or equal to four-fold increase in MIC. The next step will then test whether any such mutants can 3) elude the marked fitness defects previously demonstrated for AmB-resistant strains, including sensitivity to oxidative stress heightened dependence on Hsp90, 4) retain the capacity for filamentation upon stimulation with fetal bovine serum, and/or 5) retain the capacity to cause lethal infection in mice. C2'epiAmBUreas that are verified to primarily operate via the sterol sponge mechanism and possess AmB-like capacity to evade resistance, will be advanced to secondary in vitro screening (see C.3.5.).

C.3.5. Secondary Screen For Extended Broad Spectrum In Vitro Antifungal Activity Remaining C2'epiAmBUreas will next be evaluated for their broad-spectrum efficacy in an extended panel of clinically-relevant pathogens. Specifically, the Steinbach lab will determine the activity of these compounds, tested in triplicate against azole-resistant C. albicans, echinocandin-resistant C. glabrata, Cryptococcus neoformans, A. calidoustus, A. lentulus, azole-resistant A. fumigatus, echinocandin-resistant A. fumigatus, Scedosporium prolificans, Scedosporium apiospermum, Fusarium solani, Fusarium oxysporum, Rhizopus oryzae, Mucor circinelloides, Rhizomucor pusillus, and Paecilomyces variotii. These strains have been carefully selected to represent difficult to treat invasive yeast and mold infections with no accepted or effective antifungal therapy or the emergence of antifungal resistance. As a benchmark of broad-spectrum activity, a compound has to manifest MIC≤8 µM against 95% of the strains tested and an average MIC≤2 µM against each class of pathogens. Compounds satisfying the aforementioned criteria ranked on the basis of their average MIC, and the top 5 candidates will be advanced to evaluate in vivo PK and toxicity (see C.3.6).

C.3.6. PK and Toxicity in a Dose-Escalation Study

Building on previous studies with AmB, the maximal peak plasma concentrations for AmB, AmBisome®, voriconazole, caspofungin, C2'epiAmB, and the top 5 C2'epiAmBUreas by head-to-head characterization of the PK and toxicity of all compounds as single IP doses in a dose escalation study will be first determined. Specifically, neutropenic [IP cyclophosphamide (150 mg/kg) on day −4 and (100 mg/kg) on day −1 of injection] ICR/Swiss mice (4 per group) will be injected IP with a single dose of AmB-deoxycholate, AmBisome®, voriconazole, caspofungin, or C2'epiAmB-deoxycholate at 0.25, 1, 2.5, 5, 10, 20, 40, 80, and 120 mg/kg. The study will then determine corresponding drug concentrations in serum at 0, 10 m, 20 m, 30 m, 40 m, 1 h, 2 h, 4 h, 6 h, 12 h, 24 h, 48 h, and 60 h via HPLC. After 60 hours, the serum Blood Urea Nitrogen to creatinine ratio (BUN/Cr), levels of renal genotoxicity markers (Kim1, Lcn2, Timp1, and Spp1), and renal histopathology will be determined. Genotoxicity markers and renal histopathology will be determined via sacrificing the animals and harvesting the kidneys, followed by homogenization of one kidney and quantification of Kim 1, Lcn2, Timp 1, and Spp1 expression via RT-PCR (FIG. 7) and histopathological evaluation of the other kidney (H&E and osteopontin). Using this multi-pronged pharmacokinetic and toxicity strategy, the maximum dose for AmB-deoxycholate, AmBisome®, voriconazole, caspofungin, C2'epiAmB-deoxycholate, and the top 5 C2'epiAmBUreas with no statistically significant toxicity will be identified.

C.3.7. Determine MTD in a Daily (QD) Multi-Dose Treatment Study

For AmB, AmBisome®, voriconazole, caspofungin, C2'epiAmB, and the top 5 C2'epiAmBUreas, the study will next test toxicity in animals of the maximum single dose that causes no statistically significant elevations in BUN/Cr or renal genotoxicity markers (see C.3.6), along with one dose higher and one dose lower in QD multi-dose treatment studies for 7 days. For each dose selected, neutropenic ICR/Swiss mice (4 per group) will be injected IP QD for 7 days. One kidney will be analyzed for renal genotoxicity markers Kim1, Lcn2, Timp1, and Spp1 via RT-PCR, and the other kidney will be analyzed for renal pathology via osteopontin and H&E staining. MTD for the 7 day QD treatment protocol will be defined as the dose of each compound that causes no deaths and only mild changes (≤20% increase) in BUN/Cr, renal genotoxicity markers, and renal pathology metrics.

C.3.8. PKs of the MTD in QD Multi-Dose Treatment Study

The study will next determine the PK profiles of the MTD of AmB, AmBisome®, voriconazole, caspofungin, C2'epiAmB, and the top 5 C2'epiAmBUreas following QD multi-dose treatments for 7 days. Specifically, neutropenic ICR/Swiss mice will be injected IP with the MTD of each compound (as determined in study C.3.7) QD for 7 days, and a 13 point PK curve will be generated as detailed in C.3.6.

C.3.9. Perform High-Dose Efficacy Studies With MTD of QD Multi-Dose Treatment in a Murine Model of Invasive Candidiasis Using the well-characterized MTDs of AmB, AmBisome®, voriconazole, caspofungin, C2'epiAmB, and the top 5 C2'epiAmBUreas, the study will test efficacy of each compound after 7 days QD treatment protocols in murine models of invasive candidiasis using two different strains in the well-established murine invasive candidiasis model used for 20 years in the Andes lab. Andes, D. et al., *Antimicrobial agents and chemotherapy* 2001, 45 (3), 922-6. Each arm will contain 10 mice. Briefly, neutropenic ICR/Swiss mice will be infected with *C. albicans* via lateral tail vein 2 h prior to the start of therapy. Animals will be treated QD with the MTD of each compound or vehicle control for 7 days. Animals will be monitored daily for adverse events and 24 h after the last injection all surviving animals will be sacrificed and both kidneys removed, homogenized, and plated for viable fungal colony counts.

C.3.10. Perform High-Dose Efficacy Studies With MTD of QD Multi-Dose Treatment in a Murine Model of Invasive Aspergillosis This study will similarly test the efficacy of AmB, AmBisome®, voriconazole, caspofungin, C2'epiAmB, and the top five C2'epiAmBUreas after 7 day QD treatment protocols using two different strains in a well-established model of invasive aspergillosis used in the Steinbach lab for over 15 years. Steinbach, W. J. et al., *Antimicrobial agents and chemotherapy* 2004, 48 (9), 3217-25. Each of these strains will then be tested in immunocompromised mice [cyclophosphamide 150 mg/kg (days −2, +3) and triamcinolone 40 mg/kg (days −1, +6)] and exposed to an aerosol of the strain (day 0) to develop pulmonary invasive aspergillosis. Each arm will contain 10 mice for adequate statistical power. Survival will be plotted on a Kaplan-Meier curve with log rank pair-wise comparison. Fungal burden with galactomannan assay at a pre-determined time point (day +5 after infection) will be analyzed with the Kruskal-Wallis test with Dunn's post-test. Histopathologic disease and tissue invasion, with lungs stained with hematoxylin and eosin for inflammation and Gomori's methenamine silver stain for fungal invasion, will be assessed according to a five-point pulmonary infarct score we developed. The two C2'epiAmBUreas that prove to be most effective in eradicating invasive candidiasis and aspergillosis in these experiments will be advanced for further studies in larger animals (see Example 9).

C.3.11. Expected Results, Potential Pitfalls, and Alternative Strategies

The results with C2'epiAmBAU strongly support the prediction that C16 modifications will show improved potency compared to C2'epiAmB. Importantly, C2'epiAmBAU is also substantially less toxic than AmB, but this study did observe low but measurable toxicity to hRECs. It is noted that AmBAU was one of the most toxic of the earlier series of AmBUreas, and many other AmBUreas were much less toxic that AmBAU yet still demonstrated excellent solubilities and antifungal potencies. Thus, it is expected that hybridizations of C2'epiAmB with other urea side chains will yield similar increases in potency without any mammalian toxicity. If this proves not to be the case, other classes of C16 modifications that also increase potency will be pursed. For example, C2'epiAmB C16 methyl ester (C2'epiAmBME) has been recently synthesized and it was found to also have substantially improved potency relative to C2'epiAmB against *A. fumigatus* 91 (MIC=>64 μM for C2'epiAmB and 4 μM for C2'epiAmBME) and *A. fumigatus* 1100 (MIC=32 μM for C2'epiAmB and 4 μM for C2'epiAmBME). This study also recently found that C16 amides of AmB substantially improve potency against a broad range of clinically relevant pathogens. Alternative modifications may be pursed at the mycosamine appendage that the modelling predicts should similarly eliminate the water-bridged C2'OH to C13OH hydrogen bond, e.g., C2'deoxygenation, C2'-halodeoxygenation, or C2'-methyldeoxygenation, and thus eliminate cholesterol binding (see FIGS. 3A and 3B). This study anticipates high doses of non-toxic C2'epiAmBUreas will yield a significant reduction in fungal burden and therefore an increase in survival in QD dosing efficacy studies relative to AmB-deoxycholate (Fungizone®), AmBisome®, C2'epiAmB, voriconazole, and caspofungin.

Example 9

Characterize the Safety of the Two Top C2'epiAmBUreas in Larger Animals

C.4.1. Safety in Rats

The two top C2'epiAmBUreas selected from C.3.7 will be administered IV at 1, 10, 20, 40 and 80 mg/kg to Sprague Dawley rats (3 male/3 female, again to account for sex as a biological variable) to evaluate toxicity and pharmacokinetic properties (as described for mice in C.3.6). Rats will be evaluated for weight loss, death, and elevations in BUN, Creatinine, and ALT/AST. In addition, this study will quantify urinary kidney biomarkers NGAL, albumin, clusterin, Kim1, Cystatin, osteopontin, and kidneys will be sectioned, stained, and analyzed for renal pathology by a pathologist. At the conclusion of this study, in addition to kidney tissues, all rats will have internal organs [brain, lung, heart, liver, spleen, stomach, small intestine, large intestine, bladder and gonadal organs (ovaries or testes)] collected for histological analysis, as well as bone marrow cytology. The C2'epiAmBUrea that shows the least overall toxicity in these rats and the highest $C_{max}$ will be selected for further studies in beagle dogs.

C.4.2. PK and Safety in Beagle Dogs

The top performing C2'epiAmBUrea will be further characterized in healthy beagle dogs, a large mammalian, non-rodent species. Extensive preclinical toxicity data of AmB-deoxycholate exists in dogs, identifying 0.625 mg/kg IV daily for 30 consecutive days as the MTD associated with reproducible renal pathology. With the expectation that the best performing C2'epiAmBUrea will afford at least a 10-fold increase in biologic tolerability in comparison with AmB-deoxycholate while retaining potent antifungal activities, 6 sexually-intact beagle dogs (3 male/3 female) will be treated daily for 14 consecutive days (a clinically relevant exposure duration for managing invasive fungal infections in humans) with the top C2'epiAmBUrea at 6.25 mg/kg as a 10-minute slow IV bolus. The study will then determine the corresponding drug concentrations in serum at 0, 10 m, 20 m, 30 m, 40 m, 1 h, 2 h, 4 h, 6 h, 12 h, and 24 h via HPLC on Day 1 (initial) and Day 14 (final) of C2'epiAmBUrea administration. Serial complete blood counts, chemistry panels, and urinalyses will be assessed pre-treatment (Day 0), and on Days 7 and 14 of drug administration for the detection of associated hematologic, non-hematologic, renal tubular toxicities. Beagle dogs will be observed daily for clinical symptoms associated with toxicity including lethargy, inappetence, vomiting, and diarrhea. On Day 15, beagle dogs will be humanely sacrificed, and a warm necropsy performed with detailed weighing and histologic assessment of the following internal organs [brain, lung, heart, thymus, thyroid gland, liver, spleen, lymph node, stomach, kidney, adrenal gland, small intestine, large intestine, bladder, gonadal organs (ovaries or testes) and bone marrow].

C.4.3. Expected Results, and Alternative Strategies

These studies expect the top C2'epiAmBUrea to show little or no toxicity in rats and beagle dogs. If unexpected toxicity is observed in either species, this study will alternatively test other C2'epiAmBUreas that also performed well in the screening funnel. As described above, if necessary this study will also pursue other mycosamine and/or C16 modifications that collectively maximize potency but yield no cholesterol binding and no mammalian toxicity.

Example 10

Synthesis and Characterization of C16 Urea Derivatives of AmB

As discussed above, a semisynthetic route to AmBUreas (FIG. 11A) from AmB was developed. A series of C16 Urea Derivatives of AmB have been synthesized via this route. The synthesis of these AmB ureas further supports the broad applicability of the oxazolidinone reagent with the C2'-epi-mycosamine (Scheme 1, compound 1) to make hybrid AmB ureas from a wide range of amines.

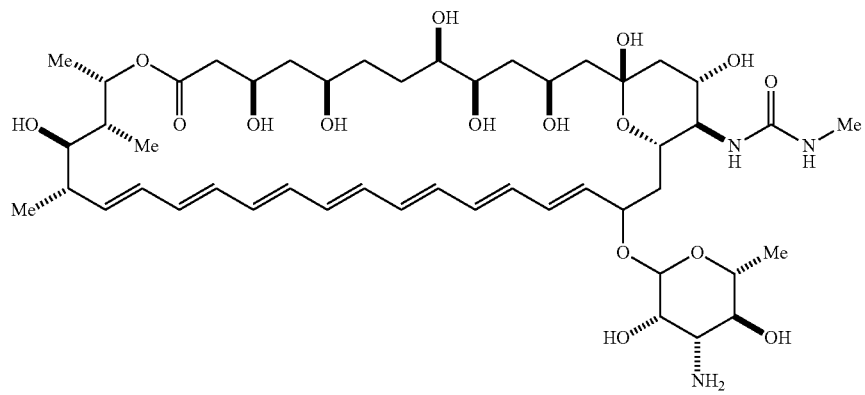 [SMILES: CNC(=O)N[C@H]1[C@@H]2CC(OC3O[C@H](C)[C@@H](O)[C@H](N)[C@@H]3O)/C=C/C=C/C=C/C=C/C=C/C=C/C=C/[C@H](C)[C@@H](O)[C@@H](C)[C@H](C)OC(=O)C[C@H](O)C[C@H](O)CC[C@@H](O)[C@H](O)C[C@H](O)C[C@](O)(C[C@@H]1O)O2]

A round bottom flask was charged with amphotericin B (0.5 g, ca. 1.082 mmol, 1 eq) and Fmocsuccinimide (0.28 g, 0.81 mmol, 1.5 eq) which were dissolved in a 2:1 mixture of DMF:MeOH (16.9 mL) at room temperature. Pyridine (0.25 mL, 3.10 mmol, 5.74 eq) was subsequently added and the reaction was stirred for 12 hours at room temperature. The reaction mixture was then poured into diethyl ether (0.5 L). After stirring for 30 minutes, the resulting yellow precipitate was isolated via Büchner filtration using Whatman #50 filter paper to afford a yellow solid. The filter cake was dried on the filter for 10 minutes and then stored under vacuum for one hour.

The resulting powder was dissolved in 1:1 THF:MeOH (18 mL) and cooled to 0° C. To this solution was added camphorsulfonic acid (69 mg, 0.30 mmol, 0.55 eq) and the resulting mixture was stirred for 1 hour at 0° C. The reaction was then quenched at 0° C. with triethylamine (0.07 mL, 0.30 mmol, 0.55 eq). The reaction was concentrated in vacuo removing approximately half of the solvent. The resulting saturated solution was poured into 1:1 hexanes:diethyl ether (0.5 L) and the yellow precipitate was collected via Büchner filtration using Whatman #50 filter paper and washed with diethyl ether (100 mL) to yield a yellow solid.

The resulting solid was dissolved in THF (14 mL, 0.01 M). To this solution was added triethylamine (0.075 mL, 0.54 mmol, 1 eq) and then diphenyl phosphoryl azide (0.35 mL, 1.63 mmol, 3 eq). The reaction was heated to 50° C. and stirred for 12 hours. After 12 hours the reaction was cooled to room temperature and methylamine (1.0 M in THF, 2.17 mL, 4.4 mmol, 8 eq) was added. The reaction then stirred at room temperature for 8 hours, slowly evolving a yellow precipitate. The reaction mixture was then poured into diethyl ether (0.5 L), and the resulting yellow precipitate was isolated via Büchner filtration using Whatman #50 filter paper to afford a yellow solid. The solid was dissolved in DMSO (~100 mg/mL) and purified by a single prep-HPLC purification (C18, 5-μm, 50×250 mm, 75 mL/min, 80:20 to 59:41 0.3% HCO2H (aq):MeCN over 9 minutes), Following HPLC purification, the solvent was removed in vacuo at 40° C. Upon complete solvent removal, residual formic acid was removed via azeotroping with milliQ water (10 mL) and toluene (50 mL). This process was repeated three times to ensure formic acid removal. During the course of this HPLC purification the methyl ketal was quantitatively converted to a hemiketal, and then get the compound dissolved in DMSO and dried on lyophilizer yielding AmBMU as a yellow solid.

Exact Mass Calculated 952.5382; HRMS (ESI) Observed [C48H77N3O16+H]$^+$ 952.5378 reaction mixture was then poured into diethyl ether (0.5 L). After stirring for 30 minutes, the resulting yellow precipitate was isolated via Büchner filtration using Whatman #50 filter paper to afford a yellow solid. The filter cake was dried on the filter for 10 minutes and then stored under vacuum for one hour.

The resulting powder was dissolved in 1:1 THF:MeOH (18 mL) and cooled to 0° C. To this solution was added camphorsulfonic acid (69 mg, 0.30 mmol, 0.55 eq) and the resulting mixture was stirred for 1 hour at 0° C. The reaction was then quenched at 0° C. with triethylamine (0.07 mL, 0.30 mmol, 0.55 eq). The reaction was concentrated in vacuo removing approximately half of the solvent. The resulting saturated solution was poured into 1:1 hexanes:diethyl ether (0.5 L) and the yellow precipitate was collected via Büchner filtration using Whatman #50 filter paper and washed with diethyl ether (100 mL) to yield a yellow solid.

The resulting solid was dissolved in THF (14 mL, 0.01 M). To this solution was added triethylamine (0.075 mL, 0.54 mmol, 1 eq) and then diphenyl phosphoryl azide (0.35 mL, 1.63 mmol, 3 eq). The reaction was heated to 50° C. and stirred for 12 hours. After 12 hours the reaction was cooled to room temperature and ethylamine (198 mg, 4.4 mmol, 8 eq) was added. The reaction then stirred at room temperature for 8 hours, slowly evolving a yellow precipitate. The reaction mixture was then poured into diethyl ether (0.5 L), and the resulting yellow precipitate was isolated via Büchner filtration using Whatman #50 filter paper to afford a yellow solid. The solid was dissolved in DMSO (~100 mg/mL) and purified by a single prep-HPLC purification (C18, 5-μm, 50×250 mm, 75 mL/min, 80:20 to 59:41 0.3% HCO2H (aq):MeCN over 9 minutes), Following HPLC purification, the solvent was removed in vacuo at 40° C. Upon complete solvent removal, residual formic acid was removed via azeotroping with milliQ water (10 mL) and toluene (50 mL). This process was repeated three times to ensure formic acid

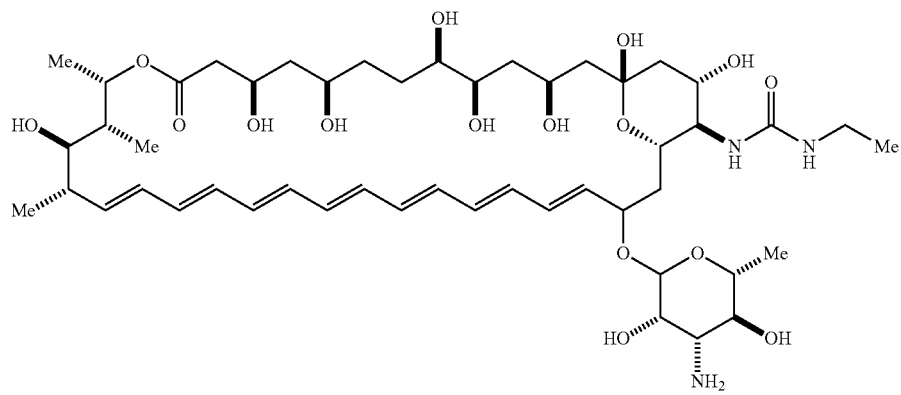 [SMILES: CCNC(=O)N[C@H]1[C@@H]2CC(OC3O[C@H](C)[C@@H](O)[C@H](N)[C@@H]3O)/C=C/C=C/C=C/C=C/C=C/C=C/C=C/[C@H](C)[C@@H](O)[C@@H](C)[C@H](C)OC(=O)C[C@H](O)C[C@H](O)CC[C@@H](O)[C@H](O)C[C@H](O)C[C@](O)(C[C@@H]1O)O2]

A round bottom flask was charged with amphotericin B (0.5 g, ca. 1.082 mmol, 1 eq) and Fmocsuccinimide (0.28 g, 0.81 mmol, 1.5 eq) which were dissolved in a 2:1 mixture of DMF:MeOH (16.9 mL) at room temperature. Pyridine (0.25 mL, 3.10 mmol, 5.74 eq) was subsequently added and the reaction was stirred for 12 hours at room temperature. The removal. During the course of this HPLC purification the methyl ketal was quantitatively converted to a hemiketal, and then get the compound dissolved in DMSO and dried on lyophilizer yielding as a yellow solid.

Exact Mass Calculated 966.5539; HRMS (ESI) Observed [C49H79N3O16+H]$^+$ 966.4875.

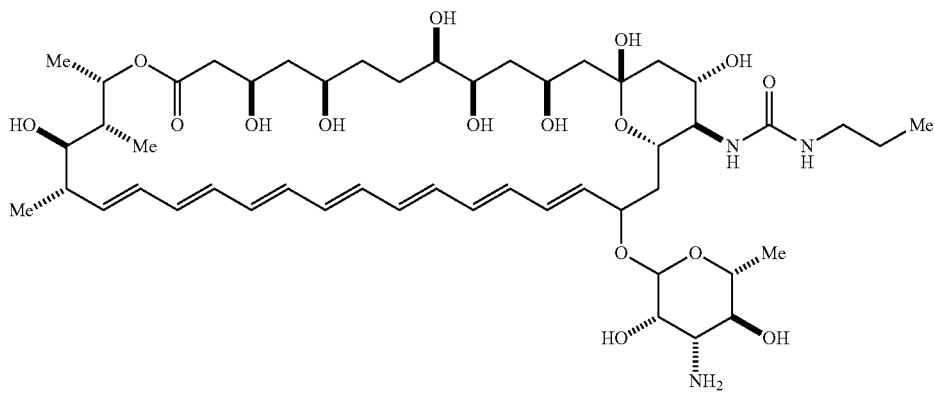 [SMILES: CCCNC(=O)N[C@H]1[C@@H]2CC(OC3O[C@H](C)[C@@H](O)[C@H](N)[C@@H]3O)/C=C/C=C/C=C/C=C/C=C/C=C/C=C/[C@H](C)[C@@H](O)[C@@H](C)[C@H](C)OC(=O)C[C@H](O)C[C@H](O)CC[C@@H](O)[C@H](O)C[C@H](O)C[C@](O)(C[C@@H]1O)O2]

A round bottom flask was charged with amphotericin B (0.5 g, ca. 1.082 mmol, 1 eq) and Fmocsuccinimide (0.28 g, 0.81 mmol, 1.5 eq) which were dissolved in a 2:1 mixture of DMF:MeOH (16.9 mL) at room temperature. Pyridine (0.25 mL, 3.10 mmol, 5.74 eq) was subsequently added and the reaction was stirred for 12 hours at room temperature. The reaction mixture was then poured into diethyl ether (0.5 L). After stirring for 30 minutes, the resulting yellow precipitate was isolated via Büchner filtration using Whatman #50 filter paper to afford a yellow solid. The filter cake was dried on the filter for 10 minutes and then stored under vacuum for one hour.

The resulting powder was dissolved in 1:1 THF:MeOH (18 mL) and cooled to 0° C. To this solution was added camphorsulfonic acid (69 mg, 0.30 mmol, 0.55 eq) and the resulting mixture was stirred for 1 hour at 0° C. The reaction was then quenched at 0° C. with triethylamine (0.07 mL, 0.30 mmol, 0.55 eq). The reaction was concentrated in vacuo removing approximately half of the solvent. The resulting saturated solution was poured into 1:1 hexanes:diethyl ether (0.5 L) and the yellow precipitate was collected via Büchner filtration using Whatman #50 filter paper and washed with diethyl ether (100 mL) to yield a yellow solid.

The resulting solid was dissolved in THF (14 mL, 0.01 M). To this solution was added triethylamine (0.075 mL, 0.54 mmol, 1 eq) and then diphenyl phosphoryl azide (0.35 mL, 1.63 mmol, 3 eq). The reaction was heated to 50° C. and stirred for 12 hours. After 12 hours the reaction was cooled to room temperature and propylamine (321 mg, 4.4 mmol, 8 eq) was added. The reaction then stirred at room temperature for 8 hours, slowly evolving a yellow precipitate. The reaction mixture was then poured into diethyl ether (0.5 L), and the resulting yellow precipitate was isolated via Büchner filtration using Whatman #50 filter paper to afford a yellow solid. The solid was dissolved in DMSO (~100 mg/mL) and purified by a single prep-HPLC purification (C18, 5-μm, 50×250 mm, 75 mL/min, 80:20 to 59:41 0.3% HCO2H (aq):MeCN over 9 minutes), Following HPLC purification, the solvent was removed in vacuo at 40° C. Upon complete solvent removal, residual formic acid was removed via azeotroping with milliQ water (10 mL) and toluene (50 mL). This process was repeated three times to ensure formic acid removal. During the course of this HPLC purification the methyl ketal was quantitatively converted to a hemiketal, and then get the compound dissolved in DMSO and dried on lyophilizer yielding as a yellow solid.

Exact Mass Calculated 980.5695; HRMS (ESI) Observed [C50H81N3O16+H]$^+$ 980.5666

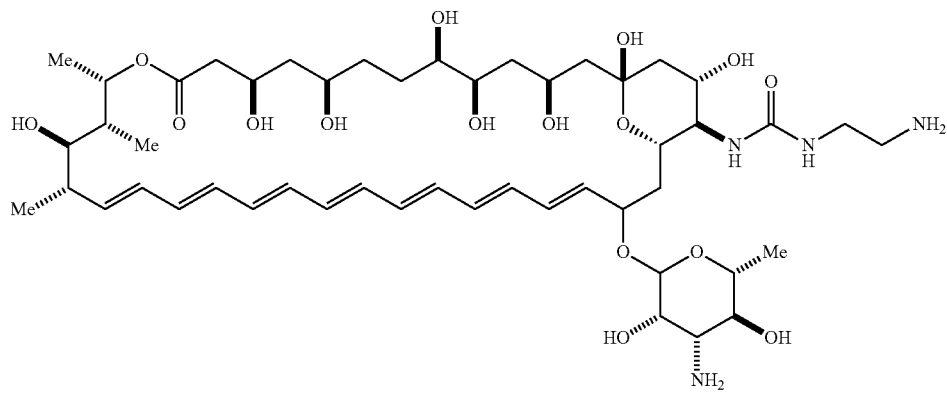 [SMILES: C[C@@H]1[C@H](O)[C@@H](C)/C=C/C=C/C=C/C=C/C=C/C=C/C=C/C(OC2O[C@H](C)[C@@H](O)[C@H](N)[C@@H]2O)C[C@@H]2O[C@](O)(C[C@@H](O)C[C@@H](O)[C@H](O)CC[C@@H](O)C[C@@H](O)CC(=O)O[C@H]1C)C[C@H](O)[C@H]2NC(=O)NCCN]

A round bottom flask was charged with amphotericin B (0.5 g, ca. 1.082 mmol, 1 eq) and Fmocsuccinimide (0.28 g, 0.81 mmol, 1.5 eq) which were dissolved in a 2:1 mixture of DMF:MeOH (16.9 mL) at room temperature. Pyridine (0.25 mL, 3.10 mmol, 5.74 eq) was subsequently added and the reaction was stirred for 12 hours at room temperature. The reaction mixture was then poured into diethyl ether (0.5 L). After stirring for 30 minutes, the resulting yellow precipitate was isolated via Büchner filtration using Whatman #50 filter paper to afford a yellow solid. The filter cake was dried on the filter for 10 minutes and then stored under vacuum for one hour.

The resulting powder was dissolved in 1:1 THF:MeOH (18 mL) and cooled to 0° C. To this solution was added camphorsulfonic acid (69 mg, 0.30 mmol, 0.55 eq) and the resulting mixture was stirred for 1 hour at 0° C. The reaction was then quenched at 0° C. with triethylamine (0.07 mL, 0.30 mmol, 0.55 eq). The reaction was concentrated in vacuo removing approximately half of the solvent. The resulting saturated solution was poured into 1:1 hexanes:diethyl ether (0.5 L) and the yellow precipitate was collected via Büchner filtration using Whatman #50 filter paper and washed with diethyl ether (100 mL) to yield a yellow solid.

The resulting solid was dissolved in THF (27 mL, 0.01 M). To this solution was added triethylamine (0.075 mL, 0.54 mmol, 1 eq) and then diphenyl phosphoryl azide (0.35 mL, 1.63 mmol, 3 eq). The reaction was heated to 50° C. and stirred for 12 hours. After 12 hours, ethylene diamine (0.15 mL, 1.67 mmol, 4 eq) was added, and the reaction continued stirring at 50° C. for 3 hours, slowly evolving a yellow precipitate. The reaction mixture was then poured into diethyl ether (0.5 L), and the resulting yellow precipitate was isolated via Büchner filtration using Whatman #50 filter paper to afford a yellow solid which was dissolved in DMSO (~66 mg/mL) and purified by prep-HPLC (C18, 5-µm, 50×250 mm, 75 mL/min, 80:20 to 50:50 0.3% HCO2H (aq):MeCN over 9 minutes). After HPLC purification the solvent was removed in vacuo at 40° C. Upon complete solvent removal, residual formic acid was removed via azeotroping with milliQ water (10 mL) and toluene (50 mL). This process was repeated three times to ensure formic acid removal. During the course of this HPLC purification the methyl ketal was quantitatively converted to a hemiketal, and then get the compound dissolved in DMSO and dried on lyophilizer yielding as a yellow solid.

Exact Mass Calculated 980.5569; HRMS (ESI) Observed [C49H80N4O16+H]$^+$. 981.4964.

mL, 3.10 mmol, 5.74 eq) was subsequently added and the reaction was stirred for 12 hours at room temperature. The reaction mixture was then poured into diethyl ether (0.5 L). After stirring for 30 minutes, the resulting yellow precipitate was isolated via Büchner filtration using Whatman #50 filter paper to afford a yellow solid. The filter cake was dried on the filter for 10 minutes and then stored under vacuum for one hour.

The resulting powder was dissolved in 1:1 THF:MeOH (18 mL) and cooled to 0° C. To this solution was added camphorsulfonic acid (69 mg, 0.30 mmol, 0.55 eq) and the resulting mixture was stirred for 1 hour at 0° C. The reaction was then quenched at 0° C. with triethylamine (0.07 mL, 0.30 mmol, 0.55 eq). The reaction was concentrated in vacuo removing approximately half of the solvent. The resulting saturated solution was poured into 1:1 hexanes:diethyl ether (0.5 L) and the yellow precipitate was collected via Büchner filtration using Whatman #50 filter paper and washed with diethyl ether (100 mL) to yield a yellow solid.

The resulting solid was dissolved in THF (27 mL, 0.01 M). To this solution was added triethylamine (0.075 mL, 0.54 mmol, 1 eq) and then diphenyl phosphoryl azide (0.35 mL, 1.63 mmol, 3 eq). The reaction was heated to 50° C. and stirred for 12 hours. After 12 hours, propane-1,3-diamine (124 mg, 1.67 mmol, 4 eq) was added, and the reaction continued stirring at 50° C. for 3 hours, slowly evolving a yellow precipitate. The reaction mixture was then poured into diethyl ether (0.5 L), and the resulting yellow precipitate was isolated via Büchner filtration using Whatman #50 filter paper to afford a yellow solid which was dissolved in DMSO (~66 mg/mL) and purified by prep-HPLC (C18, 5-µm, 50×250 mm, 75 mL/min, 80:20 to 50:50 0.3% HCO2H (aq):MeCN over 9 minutes). After HPLC purification the solvent was removed in vacuo at 40° C. Upon complete solvent removal, residual formic acid was removed via azeotroping with milliQ water (10 mL) and toluene (50 mL). This process was repeated three times to ensure formic acid removal. During the course of this HPLC purification the methyl ketal was quantitatively converted to

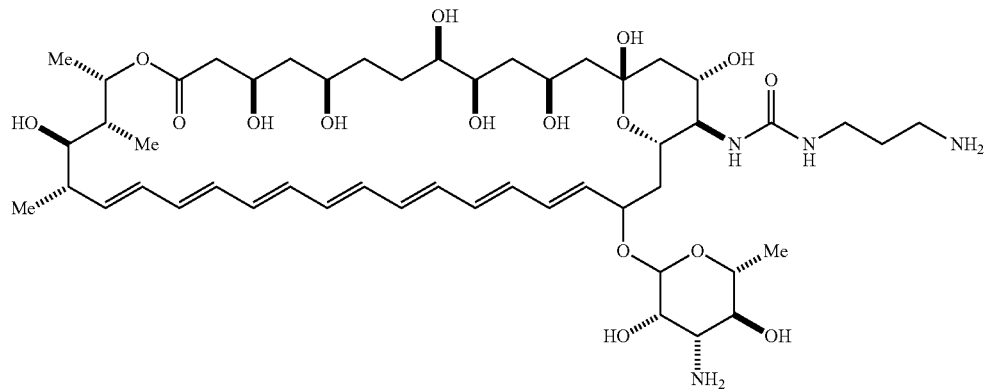 [SMILES: C[C@@H]1[C@H](O)[C@@H](C)/C=C/C=C/C=C/C=C/C=C/C=C/C=C/C(OC2O[C@H](C)[C@@H](O)[C@H](N)[C@@H]2O)C[C@@H]2O[C@](O)(C[C@@H](O)C[C@@H](O)[C@H](O)CC[C@@H](O)C[C@@H](O)CC(=O)O[C@H]1C)C[C@H](O)[C@H]2NC(=O)NCCCN]

A round bottom flask was charged with amphotericin B (0.5 g, ca. 1.082 mmol, 1 eq) and Fmocsuccinimide (0.28 g, 0.81 mmol, 1.5 eq) which were dissolved in a 2:1 mixture of DMF:MeOH (16.9 mL) at room temperature. Pyridine (0.25 a hemiketal, and then get the compound dissolved in DMSO and dried on lyophilizer yielding as a yellow solid.

Exact Mass Calculated 995.5804; HRMS (ESI) Observed [C50H82N4O16+H]$^+$. 995.5757

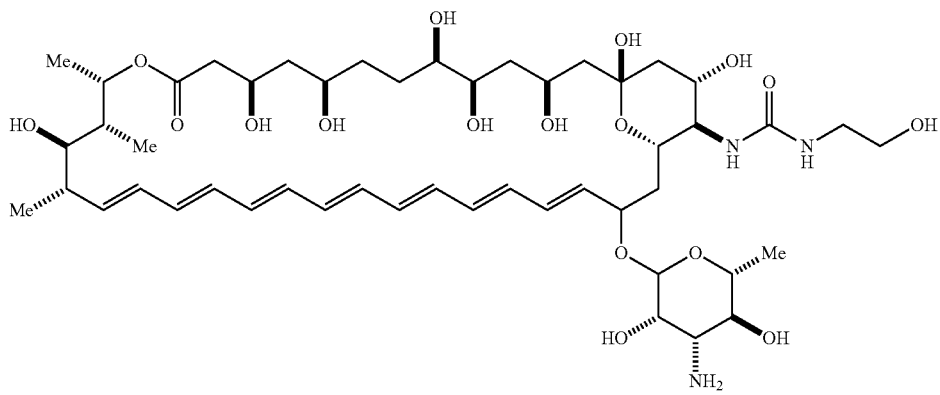 [SMILES: C[C@@H]1[C@H](O)[C@@H](C)/C=C/C=C/C=C/C=C/C=C/C=C/C=C/C(OC2O[C@H](C)[C@@H](O)[C@H](N)[C@@H]2O)C[C@@H]2O[C@](O)(C[C@@H](O)C[C@@H](O)[C@H](O)CC[C@@H](O)C[C@@H](O)CC(=O)O[C@H]1C)C[C@H](O)[C@H]2NC(=O)NCCO]

A round bottom flask was charged with amphotericin B (0.5 g, ca. 1.082 mmol, 1 eq) and Fmocsuccinimide (0.28 g, 0.81 mmol, 1.5 eq) which were dissolved in a 2:1 mixture of DMF:MeOH (16.9 mL) at room temperature. Pyridine (0.25 mL, 3.10 mmol, 5.74 eq) was subsequently added and the reaction was stirred for 12 hours at room temperature. The reaction mixture was then poured into diethyl ether (0.5 L). After stirring for 30 minutes, the resulting yellow precipitate was isolated via Büchner filtration using Whatman #50 filter paper to afford a yellow solid. The filter cake was dried on the filter for 10 minutes and then stored under vacuum for one hour.

The resulting powder was dissolved in 1:1 THF:MeOH (18 mL) and cooled to 0° C. To this solution was added camphorsulfonic acid (69 mg, 0.30 mmol, 0.55 eq) and the resulting mixture was stirred for 1 hour at 0° C. The reaction was then quenched at 0° C. with triethylamine (0.07 mL, 0.30 mmol, 0.55 eq). The reaction was concentrated in vacuo removing approximately half of the solvent. The resulting saturated solution was poured into 1:1 hexanes:diethyl ether (0.5 L) and the yellow precipitate was collected via Büchner filtration using Whatman #50 filter paper and washed with diethyl ether (100 mL) to yield a yellow solid.

The resulting solid was dissolved in THF (27 mL, 0.01 M). To this solution was added triethylamine (0.075 mL, 0.54 mmol, 1 eq) and then diphenyl phosphoryl azide (0.35 mL, 1.63 mmol, 3 eq). The reaction was heated to 50° C. and stirred for 12 hours. After 12 hours, 2-aminpethan-1-ol (102 mg, 1.67 mmol, 4 eq) was added, and the reaction continued stirring at 50° C. for 3 hours, slowly evolving a yellow precipitate. The reaction mixture was then poured into diethyl ether (0.5 L), and the resulting yellow precipitate was isolated via Büchner filtration using Whatman #50 filter paper to afford a yellow solid which was dissolved in DMSO (~66 mg/mL) and purified by prep-HPLC (C18, 5-μm, 50×250 mm, 75 mL/min, 80:20 to 50:50 0.3% HCO2H (aq):MeCN over 9 minutes). After HPLC purification the solvent was removed in vacuo at 40° C. Upon complete solvent removal, residual formic acid was removed via azeotroping with milliQ water (10 mL) and toluene (50 mL). This process was repeated three times to ensure formic acid removal. During the course of this HPLC purification the methyl ketal was quantitatively converted to a hemiketal, and then get the compound dissolved in DMSO and dried on lyophilizer yielding as a yellow solid.

Exact Mass Calculated 982.5488; HRMS (ESI) Observed [C49H79N3O17+H]$^+$. 982.5463.

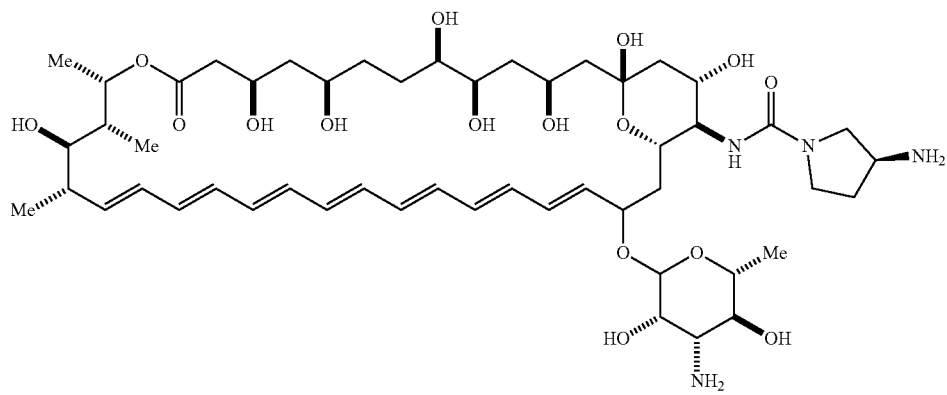 [SMILES: C[C@@H]1[C@H](O)[C@@H](C)/C=C/C=C/C=C/C=C/C=C/C=C/C=C/C(OC2O[C@H](C)[C@@H](O)[C@H](N)[C@@H]2O)C[C@@H]2O[C@](O)(C[C@@H](O)C[C@@H](O)[C@H](O)CC[C@@H](O)C[C@@H](O)CC(=O)O[C@H]1C)C[C@H](O)[C@H]2NC(=O)N1CC[C@H](N)C1]

A round bottom flask was charged with amphotericin B (0.5 g, ca. 1.082 mmol, 1 eq) and Fmocsuccinimide (0.28 g, 0.81 mmol, 1.5 eq) which were dissolved in a 2:1 mixture of DMF:MeOH (16.9 mL) at room temperature. Pyridine (0.25 mL, 3.10 mmol, 5.74 eq) was subsequently added and the reaction was stirred for 12 hours at room temperature. The reaction mixture was then poured into diethyl ether (0.5 L). After stirring for 30 minutes, the resulting yellow precipitate was isolated via Büchner filtration using Whatman #50 filter paper to afford a yellow solid. The filter cake was dried on the filter for 10 minutes and then stored under vacuum for one hour.

The resulting powder was dissolved in 1:1 THF:MeOH (18 mL) and cooled to 0° C. To this solution was added camphorsulfonic acid (69 mg, 0.30 mmol, 0.55 eq) and the resulting mixture was stirred for 1 hour at 0° C. The reaction was then quenched at 0° C. with triethylamine (0.07 mL, 0.30 mmol, 0.55 eq). The reaction was concentrated in vacuo removing approximately half of the solvent. The resulting saturated solution was poured into 1:1 hexanes:diethyl ether (0.5 L) and the yellow precipitate was collected via Büchner filtration using Whatman #50 filter paper and washed with diethyl ether (100 mL) to yield a yellow solid.

The resulting solid was dissolved in THF (27 mL, 0.01 M). To this solution was added triethylamine (0.075 mL, 0.54 mmol, 1 eq) and then diphenyl phosphoryl azide (0.35 mL, 1.63 mmol, 3 eq). The reaction was heated to 50° C. and stirred for 12 hours. After 12 hours, (3S)-pyrrolidin-3-amine (144 mg, 1.67 mmol, 4 eq) was added, and the reaction continued stirring at 50° C. for 3 hours, slowly evolving a yellow precipitate. The reaction mixture was then poured into diethyl ether (0.5 L), and the resulting yellow precipitate was isolated via Büchner filtration using Whatman #50 filter paper to afford a yellow solid which was dissolved in DMSO (~66 mg/mL) and purified by prep-HPLC (C18, 5-µm, 50×250 mm, 75 mL/min, 80:20 to 50:50 0.3% HCO2H (aq):MeCN over 9 minutes). After HPLC purification the solvent was removed in vacuo at 40° C. Upon complete solvent removal, residual formic acid was removed via azeotroping with milliQ water (10 mL) and toluene (50 mL). This process was repeated three times to ensure formic acid removal. During the course of this HPLC purification the methyl ketal was quantitatively converted to a hemiketal, and then get the compound dissolved in DMSO and dried on lyophilizer yielding as a yellow solid.

Exact Mass Calculated: 1006.5726; HRMS (ESI) Observed [C51H82N4O16+H]$^{30}$ . 1007.5057.

reaction was stirred for 12 hours at room temperature. The reaction mixture was then poured into diethyl ether (0.5 L). After stirring for 30 minutes, the resulting yellow precipitate was isolated via Büchner filtration using Whatman #50 filter paper to afford a yellow solid. The filter cake was dried on the filter for 10 minutes and then stored under vacuum for one hour.

The resulting powder was dissolved in 1:1 THF:MeOH (18 mL) and cooled to 0° C. To this solution was added camphorsulfonic acid (69 mg, 0.30 mmol, 0.55 eq) and the resulting mixture was stirred for 1 hour at 0° C. The reaction was then quenched at 0° C. with triethylamine (0.07 mL, 0.30 mmol, 0.55 eq). The reaction was concentrated in vacuo removing approximately half of the solvent. The resulting saturated solution was poured into 1:1 hexanes:diethyl ether (0.5 L) and the yellow precipitate was collected via Büchner filtration using Whatman #50 filter paper and washed with diethyl ether (100 mL) to yield a yellow solid.

The resulting solid was dissolved in THF (27 mL, 0.01 M). To this solution was added triethylamine (0.075 mL, 0.54 mmol, 1 eq) and then diphenyl phosphoryl azide (0.35 mL, 1.63 mmol, 3 eq). The reaction was heated to 50° C. and stirred for 12 hours. After 12 hours, (3R)-pyrrolidin-3-amine (144 mg, 1.67 mmol, 4 eq) was added, and the reaction continued stirring at 50° C. for 3 hours, slowly evolving a yellow precipitate. The reaction mixture was then poured into diethyl ether (0.5 L), and the resulting yellow precipitate was isolated via Büchner filtration using Whatman #50 filter paper to afford a yellow solid which was dissolved in DMSO (~66 mg/mL) and purified by prep-HPLC (C18, 5-µm, 50×250 mm, 75 mL/min, 80:20 to 50:50 0.3% HCO2H (aq):MeCN over 9 minutes). After HPLC purification the solvent was removed in vacuo at 40° C. Upon complete solvent removal, residual formic acid was removed via azeotroping with milliQ water (10 mL) and toluene (50 mL). This process was repeated three times to ensure formic acid removal. During the course of this HPLC

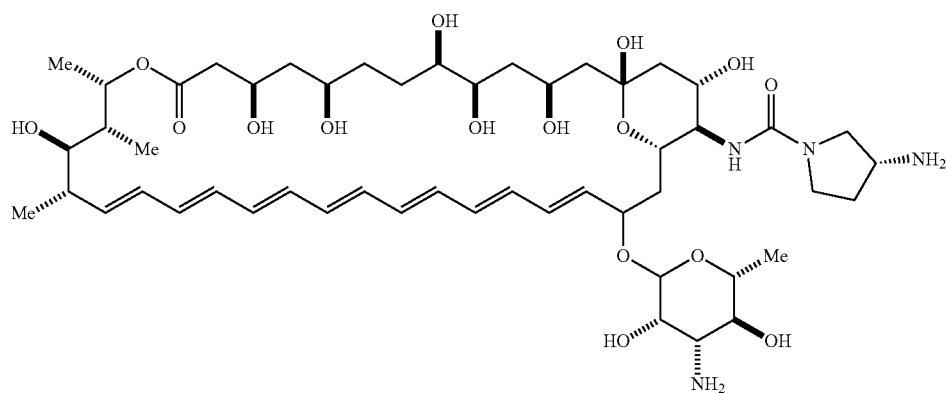 [SMILES: C[C@@H]1[C@H](O)[C@@H](C)/C=C/C=C/C=C/C=C/C=C/C=C/C=C/C(OC2O[C@H](C)[C@@H](O)[C@H](N)[C@@H]2O)C[C@@H]2O[C@](O)(C[C@@H](O)C[C@@H](O)[C@H](O)CC[C@@H](O)C[C@@H](O)CC(=O)O[C@H]1C)C[C@H](O)[C@H]2NC(=O)N1CC[C@@H](N)C1]

A round bottom flask was charged with amphotericin B (0.5 g, ca. 1.082 mmol, 1 eq) and Fmocsuccinimide (0.28 g, 0.81 mmol, 1.5 eq) which were dissolved in a 2:1 mixture of DMF:MeOH (16.9 mL) at room temperature. Pyridine (0.25 mL, 3.10 mmol, 5.74 eq) was subsequently added and the purification the methyl ketal was quantitatively converted to a hemiketal, and then get the compound dissolved in DMSO and dried on lyophilizer yielding as a yellow solid.

Exact Mass Calculated: 1006.5726; HRMS (ESI) Observed [C51H82N4O16+H]$^+$: 1007.5061

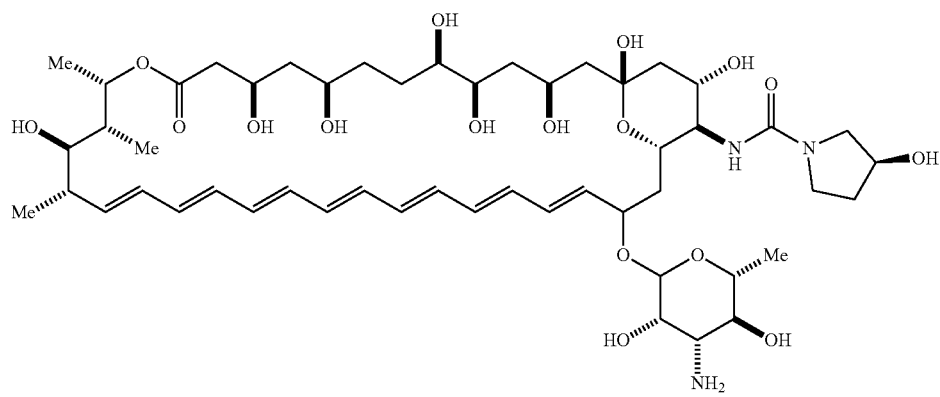 [SMILES: C[C@@H]1[C@H](O)[C@@H](C)/C=C/C=C/C=C/C=C/C=C/C=C/C=C/C(OC2O[C@H](C)[C@@H](O)[C@H](N)[C@@H]2O)C[C@@H]2O[C@](O)(C[C@@H](O)C[C@@H](O)[C@H](O)CC[C@@H](O)C[C@@H](O)CC(=O)O[C@H]1C)C[C@H](O)[C@H]2NC(=O)N1CC[C@H](O)C1]

A round bottom flask was charged with amphotericin B (0.5 g, ca. 1.082 mmol, 1 eq) and Fmocsuccinimide (0.28 g, 0.81 mmol, 1.5 eq) which were dissolved in a 2:1 mixture of DMF:MeOH (16.9 mL) at room temperature. Pyridine (0.25 mL, 3.10 mmol, 5.74 eq) was subsequently added and the reaction was stirred for 12 hours at room temperature. The reaction mixture was then poured into diethyl ether (0.5 L). After stirring for 30 minutes, the resulting yellow precipitate was isolated via Büchner filtration using Whatman #50 filter paper to afford a yellow solid. The filter cake was dried on the filter for 10 minutes and then stored under vacuum for one hour.

The resulting powder was dissolved in 1:1 THF:MeOH (18 mL) and cooled to 0° C. To this solution was added camphorsulfonic acid (69 mg, 0.30 mmol, 0.55 eq) and the resulting mixture was stirred for 1 hour at 0° C. The reaction was then quenched at 0° C. with triethylamine (0.07 mL, 0.30 mmol, 0.55 eq). The reaction was concentrated in vacuo removing approximately half of the solvent. The resulting saturated solution was poured into 1:1 hexanes:diethyl ether (0.5 L) and the yellow precipitate was collected via Büchner filtration using Whatman #50 filter paper and washed with diethyl ether (100 mL) to yield a yellow solid.

The resulting solid was dissolved in THF (27 mL, 0.01 M). To this solution was added triethylamine (0.075 mL, 0.54 mmol, 1 eq) and then diphenyl phosphoryl azide (0.35 mL, 1.63 mmol, 3 eq). The reaction was heated to 50° C. and stirred for 12 hours. After 12 hours, 2-aminpethan-1-ol (102 mg, 1.67 mmol, 4 eq) was added, and the reaction continued stirring at 50° C. for 3 hours, slowly evolving a yellow precipitate. The reaction mixture was then poured into diethyl ether (0.5 L), and the resulting yellow precipitate was isolated via Büchner filtration using Whatman #50 filter paper to afford a yellow solid which was dissolved in DMSO (~66 mg/mL) and purified by prep-HPLC (C18, 5-µm, 50×250 mm, 75 mL/min, 80:20 to 50:50 0.3% HCO2H (aq):MeCN over 9 minutes). After HPLC purification the solvent was removed in vacuo at 40° C. Upon complete solvent removal, residual formic acid was removed via azeotroping with milliQ water (10 mL) and toluene (50 mL). This process was repeated three times to ensure formic acid removal. During the course of this HPLC purification the methyl ketal was quantitatively converted to a hemiketal, and then get the compound dissolved in DMSO and dried on lyophilizer yielding as a yellow solid.

Exact Mass Calculated: 1007.5566; HRMS (ESI) Observed [C51H81N3O17+H]$^+$: 1008.4974.

Incorporation by Reference

All US patents and published US and PCT patent applications mentioned in the description above are incorporated by reference herein in their entirety.

Equivalents

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

We claim:

1. A compound represented by Formula (I) or a pharmaceutically acceptable salt thereof:

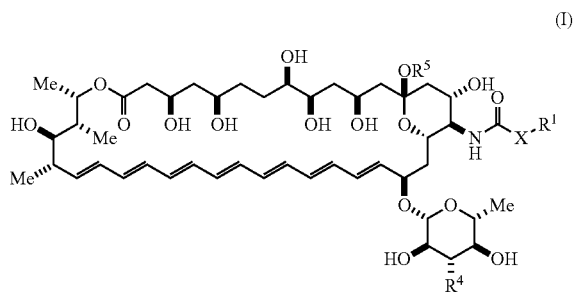

(I)

wherein, independently for each occurrence:

X is —N(R$^2$)—;

R$^1$ is a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, acyl, amino, amido, aminoalkyl, and alkoxyl; or R$^1$ and R$^2$, together with the nitrogen to which they are attached, may form a substituted or unsubstituted 3- to 10-membered heterocyclic ring, wherein said ring is monocyclic, bicyclic, tricyclic, or spirocyclic;

R$^2$ is hydrogen or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, acyl, amino, amido, aminoalkyl, and alkoxyl;

$R^4$ is selected from the group consisting of secondary amino, tertiary amino, amido, azido, isonitrile, nitro, urea, isocyanate, carbamate, and guanidinyl; and $R^5$ is selected from the group consisting of hydrogen, alkyl, and haloalkyl.

2. The compound of claim 1, wherein the compound is represented by Formula (IV) or a pharmaceutically acceptable salt thereof:

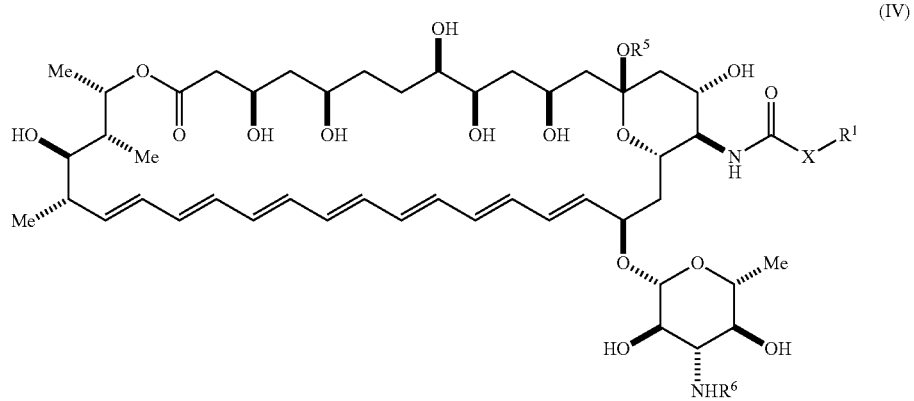

(IV)

wherein:
$R^6$ is C(O)OR$^f$; and
$R^f$ is selected from the group consisting of 2-alken-1-yl, tert-butyl, benzyl and fluorenylmethyl.

3. The compound of claim 1, wherein:
—XR$^1$ is selected from the group consisting of

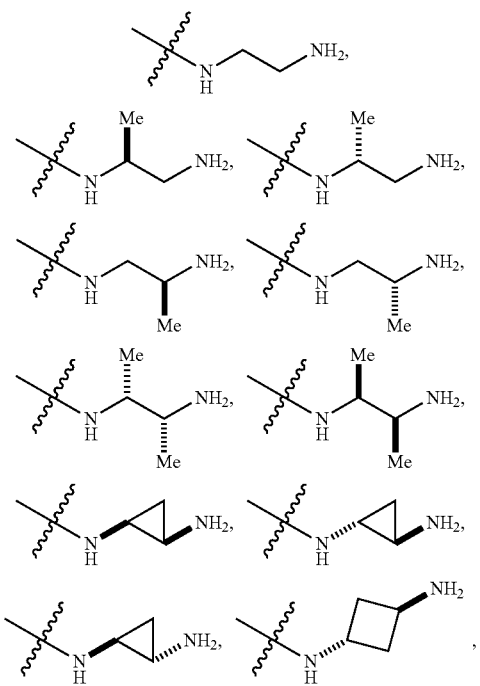

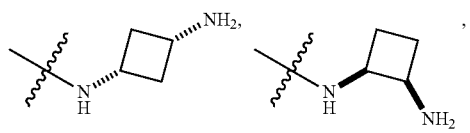

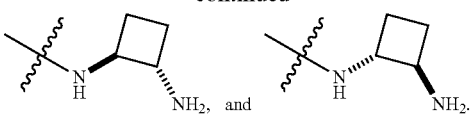

4. The compound of claim 1, wherein $R^5$ is hydrogen.
5. The compound of claim 1, wherein $R^5$ is alkyl.
6. The compound of claim 1, wherein $R^5$ is haloalkyl.
7. The compound of claim 1, wherein —XR$^1$ is

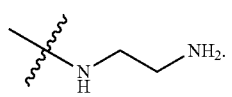

8. The compound of claim 1, wherein $R^5$ is hydrogen; and —XR$^1$ is

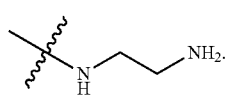

9. A compound represented by Formula (II) or a pharmaceutically acceptable salt thereof:

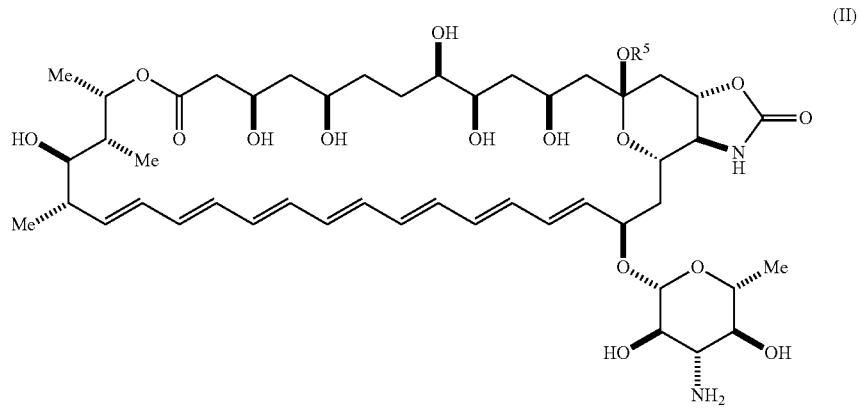

(II)

wherein, independently for each occurrence:
R⁴ is selected from the group consisting of primary amino, secondary amino, tertiary amino, amido, azido, isonitrile, nitro, urea, isocyanate, carbamate, and guanidinyl; and
R⁵ is selected from the group consisting of hydrogen, alkyl, and haloalkyl.

10. The compound of claim 9, wherein the compound is represented by Formula (III) or a pharmaceutically acceptable salt thereof:

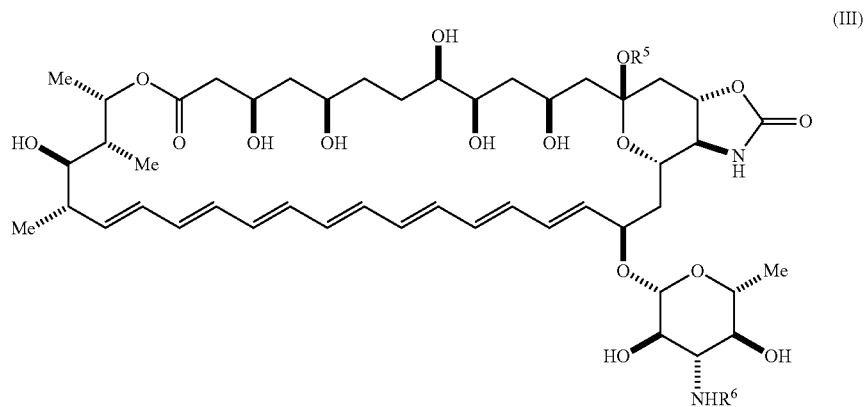

(III)

wherein:
R⁶ is —C(O)OR$^f$; and
R$^f$ is selected from the group consisting of 2-alken-1-yl, tert-butyl, benzyl and fluorenylmethyl.

11. A pharmaceutical composition, comprising a compound of claim 1; and a pharmaceutically acceptable carrier.

12. The pharmaceutical composition of claim 11, wherein the pharmaceutical composition is an intravenous dosage form.

13. The pharmaceutical composition of claim 11, wherein the pharmaceutical composition is an oral dosage form.

14. A method of treating a fungal infection, comprising administering to a subject in need thereof a therapeutically effective amount of a compound of claim 1, thereby treating the fungal infection.

15. The method of claim 14, wherein the compound is administered intravenously.

16. The method of claim 14, wherein the compound is administered orally.

17. A method of making a C16 urea derivative of C2'epi-Amphotericin B according to any one of the four transformations shown in Scheme 1:

81
82
Scheme 1
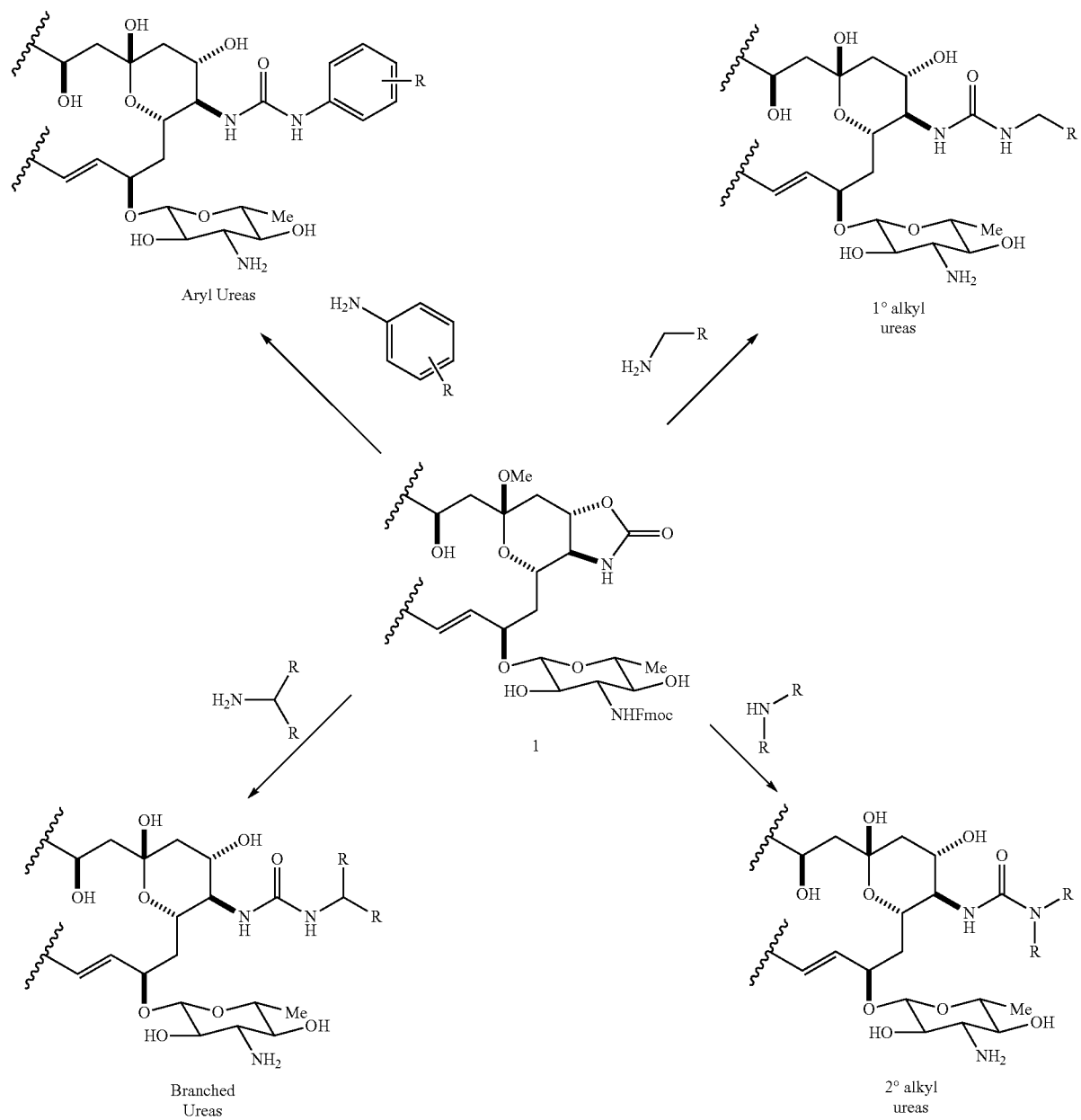
wherein 1 represents
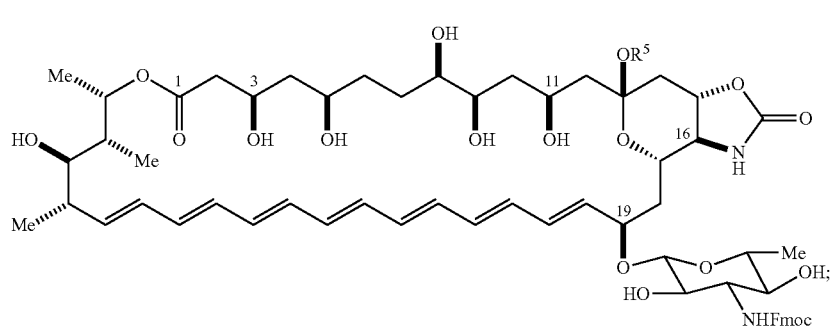

and each instance of R is independently selected from the group consisting of hydrogen, halogen, straight- and branched-chain alkyl, cycloalkyl, cycloalkylalkyl, heterocyclyl, aryl, heteroaryl, aralkyl, heteroaralkyl, hydroxyl, sulfhydryl, carboxyl, amino, amido, azido, nitro, cyano, aminoalkyl, and alkoxyl.

* * * * *